(12) United States Patent
Vafai et al.

(10) Patent No.: US 9,486,441 B2
(45) Date of Patent: Nov. 8, 2016

(54) COMPOUNDS, COMPOSITIONS AND METHODS FOR MAKING THE SAME

(75) Inventors: Scott Vafai, Boston, MA (US); Michael Voronkov, Pennington, NJ (US); Maxwell Stock, Rocky Hill, NJ (US); Jeffry B. Stock, Princeton, NJ (US); Seung-Yub Lee, Palisades Park, NJ (US); Zhu Li, Plainsboro, NJ (US); Haoming Gu, Plainsboro, NJ (US)

(73) Assignee: SIGNUM BIOSCIENCES, INC., Princeton, NJ (US)

( * ) Notice: Subject to any disclaimer, the term of this patent is extended or adjusted under 35 U.S.C. 154(b) by 0 days.

(21) Appl. No.: 12/427,743

(22) Filed: Apr. 21, 2009

(65) Prior Publication Data

US 2009/0264496 A1 Oct. 22, 2009

Related U.S. Application Data

(60) Provisional application No. 61/124,949, filed on Apr. 21, 2008, provisional application No. 61/125,205, filed on Apr. 23, 2008, provisional application No. 61/127,900, filed on May 16, 2008.

(51) Int. Cl.
*A61K 31/405* (2006.01)

(52) U.S. Cl.
CPC .................................. *A61K 31/405* (2013.01)

(58) Field of Classification Search
CPC .......................... A61K 31/404; A61K 31/405
USPC .......................................... 514/419; 548/496
See application file for complete search history.

(56) References Cited

U.S. PATENT DOCUMENTS

| | | |
|---|---|---|
| 2,852,520 A | 9/1958 | Robinson |
| 4,185,118 A | 1/1980 | Kathawala |
| 4,194,002 A | 3/1980 | Kathawala |
| 4,201,785 A | 5/1980 | Kathawala |
| 4,229,463 A | 10/1980 | Kathawala |
| 4,248,893 A | 2/1981 | Kathawala et al. |
| 4,709,094 A | 11/1987 | Weber et al. |
| 4,900,749 A | 2/1990 | Matsumoto et al. |
| 4,906,779 A | 3/1990 | Weber et al. |
| 4,933,324 A | 6/1990 | Shashoua |
| 4,935,422 A | 6/1990 | Patil et al. |
| 4,939,174 A | 7/1990 | Shashoua |
| 4,977,170 A | 12/1990 | Matsumoto et al. |
| 5,093,525 A | 3/1992 | Weber et al. |
| 5,175,183 A | 12/1992 | Brooks et al. |
| 5,189,049 A | 2/1993 | Frehel et al. |
| 5,190,976 A | 3/1993 | Weber et al. |
| 5,284,876 A | 2/1994 | Shashoua et al. |
| 5,322,858 A | 6/1994 | Canfield et al. |
| 5,527,811 A | 6/1996 | Natsugari et al. |
| 5,585,358 A | 12/1996 | Bialer et al. |
| 5,585,513 A | 12/1996 | Matthews et al. |
| 5,668,180 A | 9/1997 | Lesieur et al. |
| 5,670,499 A | 9/1997 | Cho et al. |
| 5,684,033 A | 11/1997 | Cho et al. |
| 5,700,821 A | 12/1997 | Lazo et al. |
| 5,714,094 A | 2/1998 | Bertholet et al. |
| 5,777,162 A | 7/1998 | Matthews et al. |
| 5,795,877 A | 8/1998 | Jackson et al. |
| 5,821,261 A | 10/1998 | Durette et al. |
| 5,824,662 A | 10/1998 | Slusher et al. |
| 5,849,764 A | 12/1998 | Goulet et al. |
| 5,856,506 A | 1/1999 | Lazo et al. |
| 5,863,536 A | 1/1999 | Jackson et al. |
| 5,880,132 A | 3/1999 | Hill |
| 5,902,817 A | 5/1999 | Jackson et al. |
| 5,925,660 A | 7/1999 | Lazo et al. |
| 5,939,563 A | 8/1999 | Matthews |
| 5,962,521 A | 10/1999 | Jackson et al. |
| 5,977,090 A | 11/1999 | Slusher et al. |
| 5,981,526 A | 11/1999 | Hargreaves |
| 5,985,855 A | 11/1999 | Slusher et al. |
| 5,994,392 A | 11/1999 | Shashoua |
| 6,004,946 A | 12/1999 | Slusher et al. |
| 6,013,658 A | 1/2000 | Lau et al. |
| 6,017,903 A | 1/2000 | Slusher et al. |
| 6,025,344 A | 2/2000 | Jackson et al. |
| 6,040,323 A | 3/2000 | Lazo et al. |
| 6,046,180 A | 4/2000 | Jackson et al. |
| 6,048,868 A | 4/2000 | Fourtillan et al. |
| 6,054,444 A | 4/2000 | Jackson et al. |
| 6,071,965 A | 6/2000 | Jackson et al. |
| 6,107,499 A | 8/2000 | Shashoua |

(Continued)

FOREIGN PATENT DOCUMENTS

| | | |
|---|---|---|
| AU | 64586 | 12/1994 |
| AU | 690107 | 12/1994 |

(Continued)

OTHER PUBLICATIONS

Zarkovic, Molecular Aspects of Medicine, 2003, Pergamon, vol. 24, pp. 293-303.*
Katsura et. al., Journal of Medicinal Chemistry, 1994, American Chemical Society, vol. 37, pp. 57-66.*
Wenning et. al., The Lancet:Neurology, 2004, American Academy of Neurology, vol. 3, pp. 93-103.*
Wooten, Neurology, 2003, Lippincott Williams & Wilkins, vol. 60, pp. 360-362.*
Walpole et. al., Journal of Medicinal Chemistry, 1993, American Chemical Society, vol. 36, pp. 2373-2380.*
Folstar et. al., Journal of Agricultural and Food Chemistry, 1979, American Chemical Society, vol. 27, No. 1, pp. 12-15.*
Ross et. al., Journal of the American Medical Association, 2000, American Medical Association, vol. 283, No. 20, pp. 2674-2679.*
Hu et. al., Movement Disorders, 2007, Movement Disorders Society, vol. 22, pp. 2242-2248.*

(Continued)

*Primary Examiner* — Sarah Pihonak
(74) *Attorney, Agent, or Firm* — McCarter & English, LLP; Peter Tu

(57) ABSTRACT

The present invention provides compounds and/or compositions that modulate PP2A methylation and/or activity and methods for preparing the same, which are useful for modulating the demethylation of PP2A, modulating the methylation of PP2A and/or modulating the activity of PP2A.

13 Claims, 14 Drawing Sheets

(56) References Cited

U.S. PATENT DOCUMENTS

| | | | |
|---|---|---|---|
| 6,140,324 A | 10/2000 | Tattersall | |
| 6,180,624 B1 | 1/2001 | Hill | |
| 6,232,110 B1 | 5/2001 | Pallas et al. | |
| 6,271,245 B1 | 8/2001 | Jackson et al. | |
| 6,288,046 B1 | 9/2001 | Jackson et al. | |
| 6,300,363 B1 | 10/2001 | Stevens et al. | |
| 6,303,610 B1 | 10/2001 | Johnson et al. | |
| 6,306,912 B1 | 10/2001 | Mueller et al. | |
| 6,337,344 B1 | 1/2002 | Defossa et al. | |
| 6,350,767 B1 | 2/2002 | Lau et al. | |
| 6,353,015 B1 | 3/2002 | Oxenkrug et al. | |
| 6,372,752 B1 | 4/2002 | Staveski et al. | |
| 6,403,577 B1 | 6/2002 | Cho et al. | |
| 6,465,457 B1 | 10/2002 | Matthews et al. | |
| 6,503,949 B1 | 1/2003 | Lau et al. | |
| 6,528,295 B2 | 3/2003 | Pallas et al. | |
| 6,528,655 B1 | 3/2003 | N'Zemba et al. | |
| 6,551,816 B1 | 4/2003 | Bontoux et al. | |
| 6,562,807 B2 | 5/2003 | Jorgensen et al. | |
| 6,608,196 B2 | 8/2003 | Wang et al. | |
| 6,653,304 B2 | 11/2003 | Leftheris et al. | |
| 6,683,055 B1 | 1/2004 | Hillen et al. | |
| 6,727,255 B1 | 4/2004 | Cho et al. | |
| 6,818,655 B2 | 11/2004 | Dhanak et al. | |
| 6,852,734 B2 | 2/2005 | Yamamoto et al. | |
| 6,869,957 B1 | 3/2005 | Cho et al. | |
| 6,869,975 B2 | 3/2005 | Abe et al. | |
| 6,875,760 B2 | 4/2005 | Lau et al. | |
| 6,953,812 B2 | 10/2005 | Jorgensen et al. | |
| 7,019,008 B2 | 3/2006 | Dhanak et al. | |
| 7,041,702 B1 | 5/2006 | Durant et al. | |
| 7,115,634 B2 | 10/2006 | Thurieau et al. | |
| 7,157,456 B2 | 1/2007 | Straub et al. | |
| 7,166,637 B2 | 1/2007 | Hofgen et al. | |
| 7,173,027 B2 | 2/2007 | Makriyannis et al. | |
| 7,241,923 B2 | 7/2007 | Fagerhad et al. | |
| 7,358,248 B2 | 4/2008 | Whitehouse et al. | |
| 7,393,861 B2 | 7/2008 | Thurieau et al. | |
| 7,459,472 B2 | 12/2008 | Mjalli et al. | |
| 7,476,399 B2 | 1/2009 | Tachdjian et al. | |
| 2001/0014695 A1* | 8/2001 | Behl et al. | 514/419 |
| 2001/0044459 A1 | 11/2001 | Jackson et al. | |
| 2001/0056116 A1 | 12/2001 | Shashoua | |
| 2002/0034524 A1 | 3/2002 | Poret | |
| 2002/0107374 A1 | 8/2002 | Pallas et al. | |
| 2002/0119972 A1 | 8/2002 | Leftheris et al. | |
| 2002/0143186 A1 | 10/2002 | Jorgensen et al. | |
| 2003/0013846 A1 | 1/2003 | Wang et al. | |
| 2003/0036070 A1 | 2/2003 | Chakravarti | |
| 2003/0050226 A1 | 3/2003 | Shashoua | |
| 2003/0100750 A1 | 5/2003 | Wang et al. | |
| 2003/0149108 A1 | 8/2003 | Abe et al. | |
| 2003/0153610 A1 | 8/2003 | Straub et al. | |
| 2003/0171411 A1 | 9/2003 | Kodra et al. | |
| 2003/0186416 A1 | 10/2003 | Pallas et al. | |
| 2003/0215456 A1 | 11/2003 | Yao et al. | |
| 2003/0220350 A1 | 11/2003 | Lau et al. | |
| 2004/0006089 A1 | 1/2004 | Thurieau et al. | |
| 2004/0022822 A1 | 2/2004 | Poret | |
| 2004/0024045 A1 | 2/2004 | Jorgensen et al. | |
| 2004/0053963 A1 | 3/2004 | Dhanak et al. | |
| 2004/0058963 A1 | 3/2004 | Yamamoto et al. | |
| 2004/0063757 A1 | 4/2004 | Dhanak et al. | |
| 2004/0077851 A1 | 4/2004 | Makriyannis et al. | |
| 2004/0138224 A1 | 7/2004 | Dhanak et al. | |
| 2004/0138238 A1 | 7/2004 | Dhanoa et al. | |
| 2004/0147759 A1 | 7/2004 | Hofgen et al. | |
| 2004/0152692 A1 | 8/2004 | Dhanak et al. | |
| 2004/0176444 A1 | 9/2004 | Fagerhad et al. | |
| 2004/0209934 A1 | 10/2004 | McCluskey et al. | |
| 2004/0242655 A1 | 12/2004 | Anziano | |
| 2004/0266789 A1 | 12/2004 | Whitehouse et al. | |
| 2004/0266822 A1 | 12/2004 | Wang et al. | |
| 2005/0043292 A1 | 2/2005 | Parker et al. | |
| 2005/0043388 A1 | 2/2005 | Bombrun et al. | |
| 2005/0049310 A1 | 3/2005 | Mjalli et al. | |
| 2005/0059713 A1 | 3/2005 | Mjalli et al. | |
| 2005/0084506 A1 | 4/2005 | Tachdjian et al. | |
| 2005/0181041 A1 | 8/2005 | Goldman | |
| 2005/0197345 A1 | 9/2005 | Dhanak et al. | |
| 2005/0203108 A1 | 9/2005 | Lau et al. | |
| 2005/0239796 A1 | 10/2005 | Thurieau et al. | |
| 2005/0245547 A1 | 11/2005 | Kim et al. | |
| 2005/0250819 A1 | 11/2005 | Li et al. | |
| 2005/0250839 A1 | 11/2005 | Marnett et al. | |
| 2005/0261332 A1 | 11/2005 | Distefano et al. | |
| 2006/0045953 A1 | 3/2006 | Tachdjian et al. | |
| 2006/0063789 A1 | 3/2006 | Freyne et al. | |
| 2006/0160109 A1 | 7/2006 | MacDonald et al. | |
| 2006/0171938 A1 | 8/2006 | Stock et al. | |
| 2006/0178378 A1 | 8/2006 | Dai et al. | |
| 2006/0223842 A1 | 10/2006 | Moriconi et al. | |
| 2006/0258724 A1 | 11/2006 | Straub et al. | |
| 2006/0270741 A1 | 11/2006 | Durant et al. | |
| 2006/0293362 A1 | 12/2006 | Norbert et al. | |
| 2007/0031909 A1 | 2/2007 | Stock et al. | |
| 2007/0082907 A1 | 4/2007 | Canada et al. | |
| 2007/0088072 A1 | 4/2007 | Di Marzo et al. | |
| 2007/0093531 A1 | 4/2007 | Hofgen et al. | |
| 2007/0105940 A1 | 5/2007 | Di Marzo et al. | |
| 2007/0129424 A1 | 6/2007 | Di Marzo et al. | |
| 2007/0149514 A1 | 6/2007 | Woltering et al. | |
| 2007/0161644 A1 | 7/2007 | Stockwell | |
| 2007/0191357 A1 | 8/2007 | Antel et al. | |
| 2007/0197629 A1 | 8/2007 | Somei et al. | |
| 2007/0203209 A1 | 8/2007 | Bartolini et al. | |
| 2007/0212677 A1 | 9/2007 | MacDonald et al. | |
| 2007/0225283 A1 | 9/2007 | Hammock et al. | |
| 2007/0238775 A1 | 10/2007 | Ruah et al. | |
| 2007/0243134 A1 | 10/2007 | Makriyannis et al. | |
| 2007/0259945 A1 | 11/2007 | De Petrocellis et al. | |
| 2007/0280918 A1 | 12/2007 | Schwartz et al. | |
| 2008/0021198 A1 | 1/2008 | Shi et al. | |
| 2008/0027099 A1 | 1/2008 | Govek et al. | |
| 2008/0027112 A1 | 1/2008 | Govek et al. | |
| 2008/0039442 A1 | 2/2008 | Blom et al. | |
| 2008/0090815 A1 | 4/2008 | Straub et al. | |
| 2008/0161341 A1 | 7/2008 | Calderwood et al. | |
| 2008/0161351 A1 | 7/2008 | Abe et al. | |
| 2008/0176846 A1 | 7/2008 | Chianelli et al. | |
| 2008/0176854 A1 | 7/2008 | Quintana-Ruiz | |
| 2008/0200473 A1 | 8/2008 | Falco et al. | |
| 2008/0200674 A1 | 8/2008 | Straub et al. | |
| 2008/0213406 A1 | 9/2008 | Stock et al. | |
| 2008/0221197 A1 | 9/2008 | Lam et al. | |
| 2008/0287516 A1 | 11/2008 | Wu et al. | |
| 2009/0005430 A1 | 1/2009 | Somei et al. | |

FOREIGN PATENT DOCUMENTS

| | | |
|---|---|---|
| AU | 2006230674 | 11/2006 |
| CA | 2125236 | 12/1994 |
| CN | 1205175 | 1/1999 |
| CN | 1304396 | 7/2001 |
| CN | 1415596 | 5/2003 |
| CN | 1687072 | 10/2005 |
| DE | 3105850 | 8/1982 |
| EP | 714968 | 6/1996 |
| FR | 2879601 | 6/2006 |
| JP | 3268073 | 11/1991 |
| JP | 4156825 | 5/1992 |
| JP | 06025276 | 2/1994 |
| JP | 07052542 | 2/1995 |
| JP | 3795093 | 6/1996 |
| JP | 08151366 | 6/1996 |
| JP | 09301954 | 11/1997 |
| JP | 10077229 | 3/1998 |
| JP | 10077267 | 3/1998 |
| JP | 2001247539 | 9/2001 |
| JP | 2002193923 | 7/2002 |
| JP | 2003137780 | 5/2003 |
| JP | 2004292383 | 10/2004 |
| JP | 2007145763 | 6/2007 |
| JP | 2008207466 | 9/2008 |

(56) References Cited

FOREIGN PATENT DOCUMENTS

| | | |
|---|---|---|
| JP | 2009001564 | 1/2009 |
| KR | 2003038383 | 10/2002 |
| SU | 357508 | 8/1970 |
| WO | WO-9206955 | 4/1992 |
| WO | WO-9222559 | 12/1992 |
| WO | WO-9707117 | 2/1997 |
| WO | WO-9806695 | 2/1998 |
| WO | WO-9901103 | 1/1999 |
| WO | WO-9945926 | 9/1999 |
| WO | WO-0121606 | 3/2001 |
| WO | WO-01020995 | 3/2001 |
| WO | WO-03008632 | 1/2003 |
| WO | WO 03/014321 | 2/2003 |
| WO | WO-2004031177 | 4/2004 |
| WO | WO-2004063147 | 7/2004 |
| WO | WO-2005037839 | 4/2005 |
| WO | WO-2005071101 | 8/2005 |
| WO | WO-2005089502 | 9/2005 |
| WO | WO-2006028226 | 3/2006 |
| WO | WO 2006084033 A1 * | 8/2006 |
| WO | WO-2006094235 | 9/2006 |
| WO | WO-2006101456 | 9/2006 |
| WO | WO-2006104826 | 10/2006 |
| WO | WO-2007008514 | 1/2007 |
| WO | WO-2007015866 | 2/2007 |
| WO | WO-2007079930 | 7/2007 |
| WO | WO-2007140551 | 12/2007 |
| WO | WO-2008007123 | 1/2008 |
| WO | WO-2008019357 | 2/2008 |
| WO | WO-2008031509 | 3/2008 |
| WO | WO-2008061781 | 5/2008 |
| WO | WO-2008110196 | 9/2008 |
| WO | WO-2008112525 | 9/2008 |
| WO | WO-2008113760 | 9/2008 |
| WO | WO-2008141013 | 11/2008 |
| WO | WO-2008155666 | 12/2008 |
| WO | WO-2008155668 | 12/2008 |
| WO | WO-2009020596 | 2/2009 |

OTHER PUBLICATIONS

Ghosh et. al., Proceedings of the National Academy of Sciences of the USA, 2007, The National Academy of Sciences of the USA, vol. 104, No. 47, pp. 18754-18759.*
Wenning et. al., The Lancet Neurology, 2004, Elsevier, vol. 3, pp. 93-103.*
Folstar et al., "New Tryptamine Derivatives Isolated from Wax of Green Coffee Beans", J. Agric. Food Chem., 1980, vol. 28(4), pp. 872-874.
International Search Report for International Application No. PCT/US09/41321, mailed Jun. 1, 2009.
Written Opinion of the International Searching Authority for International Patent Application No. PCT/US09/41321, mailed Jun. 1, 2009.
Abolhassani et al., "Hyperosmolarity Causes Inflammation through the Methylation of Protein Phosphatase 2A," Inflammation Research, 2008, 57(9), pp. 419-429, ISSN: 1023-3830.
Aggen et al., "The Design, Synthesis, and Biological Evaluation of Analogues of the Serine-threonine Protein Phosphatase 1 and 2A Selective Inhibitor Microcystin LA: Rational Modifications Imparting PP1 Selectivity," Bioorganic & Medicinal Chemistry, 1999, 7(3), pp. 543-564, ISSN: 0968-0896.
Battini et al., "Determination of N-Alkanoyl-5-Hydroxytryptamines (C-5-HT) in Coffee Beans by Means of HPLC and TLC," Annali di Chimica, 1989, 79(7-8), pp. 369-377.
Bialy et al., "Synthesis and Biological Evaluation of Cytostatin Analogues," Chemical Communications, 2003, 15, pp. 1872-1873, ISSN: 1359-7345.
Bialy et al., "Synthesis of the Protein Phosphatase 2A Inhibitor (4S,5S,6S,10S,11S,12S)—cytostatin," Angewandte Chemie, International Edition, 2002, 41(10), pp. 1748-1751, ISSN: 1433-7851.

Boger et al., "Total Synthesis of Fostriecin (CI-920)," Journal of the American Chemical Society, 2001, 123(18), pp. 4161-4167, ISSN: 0002-7863.
Bryant et al., "Methylated C-terminal Leucine Residue of PP2A Catalytic Subunit is Important for Binding of Regulatory BαSubunit," Biochemical Journal, 1999, 339(2), pp. 241-246, ISSN: 0264-6021.
Chan et al., "Folate Deprivation Increases Tau Phosphorylation by Homocysteine-induced Calcium Influx and by Inhibition of Phosphatase Activity: Alleviation by S-adenosyl Methionine," Brain Research, 2008, 1199, pp. 133-137, ISSN: 0006-8993.
Chen et al., "Comparison of Protein Phosphatase Inhibition Activities and Mouse Toxicities of Microcystins," Toxicon, 2006, 47(7), pp. 742-746, ISSN: 0041-0101.
Chen et al., "Improved Synthesis and Characterization of L-histidine Norcantharimide, a Novel Potent Protein Phosphatase 2A Inhibitor," Journal of Chinese Pharmaceutical Sciences, 2008, 17(2), pp. 134-137, ISSN: 1003-1057.
Chen et al., "Lithium Inhibits Ceramide- and Etoposide-induced Protein Phosphatase 2A Methylation, Bcl-2 Dephosphorylation, Caspase-2 Activation, and Apoptosis," Molecular Pharmacology, 2006, 70(2), pp. 510-517, ISSN: 0026-985X.
Christen et al., "Inhibition of Alpha Interferon Signaling by Hepatitis B Virus," Journal of Virology, 2007, 81(1), pp. 159-165, ISSN: 0022-538X.
Da Baere et al., "Purification of Porcine Brain Protein Phosphatase 2A Leucine Carboxyl Methyltransferase and Cloning of the Human Homologue," Biochemistry, 1999, 38(50), pp. 16539-16547, ISSN: 0006-2960.
Deshmukh et al., "Acute Modulation of PP2A and Troponin I Phosphorylation in Ventricular Myocytes: Studies with a Novel PP2A Peptide Inhibitor," American Journal of Physiology, 2007, 292(2, Pt. 2), pp. H792-H799, ISSN: 0002-9513.
Du, "Sml2 Mediated Aryl Radical Cyclization/Sequential Anionic Capture on Solid Support and Computational Studies on Hapalosin and its Analogs and on Inhibitors of Protein Phosphatases PP1 and PP2A," University of California, Los Angeles, 1998, 142 pp. Avail.: UMI, Order No. DA9818006, From: Diss. Abstract Int., B 1998, 58(12), pp. 6581.
Duong et al., "Hepatitis C Virus Inhibits Interferon Signaling through Up-regulation of Protein Phosphatase 2A," Gastroenterology, 2004, 126(1), pp. 263-277, ISSN: 0016-5085.
Duong et al., "S-adenosylmethionine and Betaine Correct Hepatitis C Virus Induced Inhibition of Interferon Signaling in Vitro," Hepatology, 2006, 43(4), pp. 796-806, ISSN: 0270-9139.
Duong et al., "Upregulation of Protein Phosphatase 2Ac by Hepatitics C Virus Modulates NS3 Helicase Activity throught Inhibition of Protein Arginine Methyltransferase 1," Journal of Virology, 2005, 79(24), pp. 15342-15350, ISSN: 0022-538X.
English language abstract for C36: Harms et al., "Carboxylic Acid 5-Hydroxytryptamides in Coffee Beans," Zeitschrift fuer Lebensmittel-Untersuchung und-Forschung, 1968, 138(2), pp. 75-80.
English language abstract for C42: Hunziker et al., "High-pressure Liquid Chromatographie Determination of 5-Hydroxytryptamide in Coffee," Mitteilungen aus dem Gebiete der Lebensmitteluntersuchung und Hygiene, 1979, 70(1), pp. 142-152.
English language abstract for C43: Hunziker, "Determination of 5-Hydroxytryptamide in Coffee Using High-Pressure Liquid Chromatography," Mitteilungen aus dem Gebiete der Lebensmitteluntersuchung und Hygiene, 1977, 68(2), pp. 267-274.
English language abstract for C53: Koenig et al., "Gas Chromatography and Mass Spectrometry as Aids in Studying High-Boiling Coffee Compounds," Institut fur Organische Chemie and Biochemie, pp. 271-278; and Colloque Scientifique International sur le Cafe (1983), vol. Date 1982, 10th.
Evans et al., "Functional Expression of Human PP2Ac in Yeast Permits the Identification of Novel C-terminal and Dominant-negative Mutant Forms," Journal of Biological Chemistry, 1999, 274(34), pp. 24038-24046, ISSN: 0021-9258.
Evans et al., "Mutation of the C-terminal Leucine Residue of PP2Ac Inhibits PR55/B Subunit Binding and Confers Supersensitivity to

(56) References Cited

OTHER PUBLICATIONS

Microtubule Destabilization in *Saccharomyces cerevisiae*," Molecular and General Genetics, 2000, pp. 264(4), pp. 425-432, ISSN: 00268925.

Favre et al., "Differential Inhibition and Posttranslational Modification of Protein Phosphatase 1 and 2A in MCF7 Cells Treated with Calyculin-A, Okadaic Acid, and Tautomycin," Journal of Biological Chemistry, 1997, 272(21), pp. 13856-13863, ISSN: 0021-9258.

Favre et al., "The Catalytic Subunit of Protein Phosphatase 2A is Carboxyl-Methylated In Vivo," Journal of Biological Chemistry, 1994, 269(23), pp. 16311-16317, ISSN:0021-9258.

Floer et al., "Carboxyl Methylation of Protein Phosphatase 2A from Xenopus Eggs is Stimulated by cAMP and Inhibited by Okadaic Acid," Biochemical and Biophysical Research Communications, 1994, 198(1), pp. 372-379, ISSN: 0006-291X.

Folstar et al., "Liquid Chromatographie Analysis of N-b)-Alkanoyl-5-Hydroxytryptamine (CF-HT) in Green Coffee Beans," Journal of Agricultural and Food Chemistry, 1979, 27(1), pp. 12-15.

Gentry et al., "A Novel Assay for Protein Phosphatase 2A (PP2A) Complexes in Vivo Reveals Differential Effects of Covalent Modifications on Different Saccharomyces cerevisiae PP2A Heterotrimers," Eukaryotic Cell, 2005, 4(6), pp. 1029-1040, ISSN: 1535-9778.

George et al., "Chaperonin Assisted Overexpression, Purification, and Characterisation of Human PP2A Methyltransferase," Protein Expression and Purification, 2002, 26(2), pp. 266-274, ISSN: 1046-5928.

Gonzalez et al., "Total Synthesis of Thyrsiferyl 23-Acetate, a Specific Inhibitor of Protein Phosphatase 2A and an Anti-Leukemic Inducer of Apoptosis," Journal of the American Chemical Society, 2000, 122(38), pp. 9099-9108, ISSN: 0002-7863.

Guenin et al., "PP2A Activity is Controlled by Methylation and Regulates Oncoprotein Expression in Melanoma Cells: A Mechanism which Participates in Growth Inhibition Induced by Chloroethylnitrosourea Treatment," International Journal of Oncology, 2008, 32(1), pp. 49-57, ISSN: 1019-6439.

Gulledge et al., "Linearized and Truncated Microcystin Analogues as Inhibitors of Protein Phosphatases 1 and 2A," Bioorganic & Medicinal Chemistry Letters, 2003, 13(17), pp. 2903-2906, ISSN: 0960-840X.

Gulledge et al., "Microcystin Analogues Comprised Only of Adda and a Single Additional Amino Acid Retain Moderate Activity as PP1/PP2A Inhibitors," Bioorganic & Medicinal Chemistry Letters, 2003, 13(17), pp. 2907-2911, ISSN: 0960-894X.

Guo et al., "ATM-dependent Dissociation of B55 Regulatory Subunit from Nuclear PP2A in Response to Ionizing Radiation," Journal of Biological Chemistry, 2002, 277(7), pp. 4839-4844, ISSN: 0021-9258.

Harms et al., "Carboxylic Acid 5-Hydroxytryptamides in Coffee Beans," Zeitschrift fuer Lebensmittel-Untersuchung und-Forschung, 1968, 138(2), pp. 75-80. (English language abstract provided as C19).

Hart et al., "Modified Norcantharidins Synthesis, Protein Phosphatases 1 and 2A Inhibition, and Anticancer Activity," Bioorganic & Medicinal Chemistry Letters, 2004, 14(8), pp. 1969-1973, ISSN: 0960-894X.

Hill et al, "Heterocyclic Substituted Cantharidin and Norcantharidin Analogues-synthesis, Protein Phosphatase (1 and 2A) Inhibition, and Anti-cancer Activity," Bioorganic & Medicinal Chemistry Letters, 2007, 17(12), pp. 3392-3397, ISSN: 0960-894X.

Hombauer et al., "Generation of Active Protein Phosphatase 2A is Coupled to Holoenzyme Assembly," PLoS Biology, 2007, 5(6), pp. 1355-1365, ISSN: 1545-7885.

Hornstein et al., "Protein Phosphatase and Trail Receptor Genes as New Candidate Tumor Genes on Chromosome 8p in Prostate Cancer," Cancer Genomics & Proteomics, 2008, 5(2), pp. 123-136, ISSN: 1109-6535.

Hubert et al., "Analysis of Carboxylic Acid Hydroxytryptamides in Coffee," Fresenius' Zeitschrift fuer Analytische Chemie, 1977, 285(3), pp. 242-250.

Hunziker et al., "High-pressure Liquid Chromatographie Determination of 5- Hydroxytryptamide in Coffee," Mitteilungen aus dem Gebiete der Lebensmitteluntersuchung und Hygiene, 1979, 70(1), pp. 142-152. (English language abstract provided as C20).

Hunziker, "Determination of 5-Hydroxytryptamide in Coffee Using High-Pressure Liquid Chromatography," Mitteilungen aus dem Gebiete der Lebensmitteluntersuchung und Hygiene, 1977, 68(2), pp. 267-274. (English language abstract provided as C21).

Ikehara et al., "Baculovirus Expression, Purification, and Characterization of Human Protein Phosphatase 2A Catalytic Subunits αand β," Protein Expression and Purification, 2006, 45(1), pp. 150-156, ISSN: 1046-5928.

Ikehara et al., "Methylation of the C-terminal Leucine Residue of the PP2A Catalytic Subunit is Unncecessary for the Catalytic Activity and the Binding of Regulatory Subunit (PR55/B)," Biochemical and Biophysical Research Communications, 2007, 354(4), pp. 1052-1057, ISSN: 0006-291X.

Janssens et al., "Protein Phosphatase 2A: A Highly Regulated Family of Serine/Threonine Phosphatases Implicated in Cell Growth and Signaling," Biochemical Journal, 2001, 353(3), pp. 417-439, ISSN: 0264-6021.

Kalhor et al., "Protein Phosphatase Methyltransferase 1 (Ppm1p) is the Sole Activity Responsible for Modification of the Major Forms of Protein Phosphatase 2A in Yeast," Archives of Biochemistry and Biophysics, 2001, 395(2), pp. 239-245, ISSN: 0003-9861.

Keen et al., "Epigenetic Regulation of Protein Phosphatase 2A (PP2A), Lymphotactin (XCL1) and Estrogen Receptor Alpha (ER) Expression in Human Breast Cancer Cells," Cancer Biology & Therapy, 2004, 3(12), pp. 1304-1312, ISSN: 1538-4047.

Khil et al., "Hydrogen Peroxide Mediates Brazilin-induced Glucose Transport in Adipocytes," Journal of Applied Pharmacology, 2004, 12(4), pp. 228-234, ISSN: 1225-6110.

Kita et al., "Structure-activity Relationship of Okadaic Acid, a Potent Protein Phosphatases PP1 and PP2A Inhibitor: 24-Epi-Okadaic Acid and a 18-membered Lactone Analog," Heterocycles, 2008, 76(2), pp. 1033-1042, ISSN: 0385-5414.

Kloeker et al., "Carboxymethylation of Nuclear Protein Serine/Threonine Phosphatase X," Biochemical Journal, 1997, 327(2), pp. 481-486, ISSN: 0264-6021.

Kobayashi et al., "Process Formation of Podocytes: Morphogenetic Activity of Microtubules and Regulation by Protein Serine/Threonine Phosphatase PP2A," Histochemistry and Cell Biology, 2001, 115(3), pp. 255-266, ISSN: 0948-6143.

Koenig et al., "Gas Chromatography and Mass Spectrometry as Aids in Studying High-Boiling Coffee Compounds," Institut fur Organische Chemie und Biochemie, pp. 271-278; and Colloque Scientifique International sur le Cafe (1983), vol. Date 1982, 10th. (English language abstract provided as C22).

Konoki et al., "Direct Observation of Binding Between Biotinylated Okadaic Acids and Protein Phosphatase 2A Monitored by Surface Plasmon Resonance," Tetrahedron Letters, 1999, 40(5), pp. 887-890, ISSN: 0040-4039.

Koren et al., "The Scaffolding A/Tpd3 Subunit and High Phosphatase Activity are Dispensable for Cdc55 Function in the *Saccharomyces cerevisiae* Spindle Checkpoint and in Cytokinesis," Journal of Biological Chemistry, 2004, 279(47), pp. 48598-48606, ISSN: 00219258.

Kowluru et al., "Carboxylmethylation of the Catalytic Subunit of Protein Phosphatase 2A in Insulin-secreting Cells: Evidence for Functional Consequences on Enzyme Activity and Insulin Secretion," Endocrinology, 1996, 137(6), pp. 2315-2323, ISSN: 0013-7227.

Kowluru et al., "Ceramide-activated Protein Phosphatase-2A Activity in Insulin-secreting Cells," FEBS Letters, 1997, 418(1, 2), pp. 179-182, ISSN: 0014-5793.

Kowluru et al., "Purine Nucleotide- and Sugar Phosphate-induced Inhibition of the Carboxyl Methylation and Catalysis of Protein Phosphatase-2A in Insulin-secreting Cells: Protection by Divalent Cations," Bioscience Reports, 1998, 18(4), pp. 171-186, ISSN: 0144-8463.

Kowluru, "Bridging the Gap Between Protein Carboxyl Methylation and Phospholipid Methylation to Understand Glucose-

(56) References Cited

OTHER PUBLICATIONS stimulated Insulin Secretion from the Pancreatic β Cell," Biochemical Pharmacology, 2008, 75(2), pp. 335-345, ISSN: 0006-2952.
Kurzrock et al., "Chromatography of Carbonic Acid-5-Hydroxyltryptamides," Institute of Food Chemistry, pp. 305-308; and Colloque Scientifique International sur le Cafe (2005), vol. Date 2004, 20th.
Lang et al., "A Versatile Method for the Quantitative Determination of bN-Alkanoyl-5- Hydroxytryptamides in Roasted Coffee," European Food Research and Technology, 2005, 220(5-6), pp. 638-643.
Laub et al., "[ADMAdda5]-microcysins in *Planktothrix agardhii* Strain Ph-123 (Cyanobacteria)—Importance of Monitoring of Microcystins in the Environment," Environmental Toxicology, 2002, 17(4), pp. 351-357, ISSN: 1520-4081.
Lawhorn et al, "Total Synthesis of Cytostatin," Heterocycles, 2006, 70, pp. 65-70, ISSN: 0385-5414.
Lawhorn et al., "Total Synthesis and Evaluation of Cytostatin, Its C10-C11 Diastereomers, and Additional Key Analogues: Impact on PP2A Inhibition," Journal of the American Chemical Society, 2006, 128(51), pp. 16720-16732, ISSN: 0002-7863.
Lechward et al., "Protein Phosphatase 2A: Variety of Forms and Diversity of Functions," Acta Biochimica Polonica, 2001, 48(4), pp. 921-933, ISSN: 0001-527X.
Lee et al., "A Specific Protein Carboxyl Methylesterase that Demethylates Phosphoprotein Phosphatase 2A in Bovine Brain," Proceedings of the National Academy of Sciences of the United States of America, 1996, 93(12), pp. 6043-6047, ISSN: 0027-8424.
Lee et al., "Leucine Carboxyl Methyltransferase-1 is Necessary for Normal Progression through Mitosis in Mammalian Cells," Journal of Biological Chemistry, 2007, 282(42), pp. 30974-30984, ISSN: 0021-9258.
Leulliot et al., "Structure of Protein Phosphatase Methyltransferase 1 (PPM1), A Leucine Carboxyl Methyltransferase Involved in the Regulation of Protein Phosphatase 2A Activity," Journal of Biological Chemistry, 2004, 279(9), pp. 8351-8358, ISSN: 0021-9258.
Li et al., "Okadaic Acid and Microcystin-LR Directly Inhibit the Methylation of Protein Phosphatase 2A by its Specific Methyltransferase," Biochemical and Biophysical Research Communcations, 1994, 202(2), pp. 1023-1030, ISSN: 0006-291X.
Liu et al., "Antiadrenergic Effects of Adenosine Al Receptor-mediated Protein Phosphatase 2a Activation in the Heart," American Journal of Physiology. Heart and Circulatory Physiology, 2002, 283, (4, Pt. 2), H1314-H1321, ISSN: 0002-9513.
Longin et al., "Selection of Protein Phosphatase 2A Regulatory Subunits is Mediated by the C Terminus of the Catalytic Subunit," Journal of Biological Chemistry, 2007, 282(37), pp. 26971-26980, ISSN: 0021-9258.
Maki et al., "Catalyst-controlled Asymmetric Synthesis of Fostriecin and 8-epi-Fostriecin," Journal of the American Chemical Society, 2005, 127(48), 17111-17117, ISSN:0002-7863.
Mancini et al., "Synthesis and Bioactivity of Linear Oligomers Related to Polymeric Alkylpyridinium Metabolites from the Mediterranean Sponge Reniera sarai," Organic & Biomolecular Chemistry, 2004, 2(9), pp. 1368-1375, ISSN: 1477-0520.
Martin De La Vega et al., "Cerebral Postischemic Reperfusion-induced Demethylation of the Protein Phosphatase 2A Catalytic Subunit," Journal of Neuroscience Research, 2002, 69(4), pp. 540-549, ISSN: 0360-4012.
Maude et al., "Design and Preparation of Serine-Threonine Protein Phosphatase Inhibitors Based Upon the Nodularin and Microcystin Toxin Structures: Part 2. Synthesis of a Functionalized Nodularin Macrocycle and a Stripped-down Microcystin Macrocycle," Journal of the Chemical Society, Perkin Transactions 1: Organic and Bio-Organic Chemistry, 1997, 17, pp. 2513-2526, ISSN: 0300-922X.
McCluskey et al., "Anhydride Modified Cantharidin Analogues. Is Ring Opening Important in the Inhibition of Protein Phosphatase 2A?," European Journal of Medicinal Chemistry, 2000, 35(10), pp. 957-964, ISSN: 0223-5234.
McCluskey et al., "Anhydride Modified Cantharidin Analogues: Synthesis, Inhibition of Protein Phosphatases 1 and 2A and Anti-cancer Activity," Bioorganic & Medicinal Chemistry Letters, 2000, 10(15), pp. 1687-1690, ISSN: 0960-0894X.
McCluskey et al., "The First Two Cantharidin Analogues Displaying PP1 Selectivity," Bioorganic & Medicinal Chemistry Letters, 2002, 12(3), pp. 391-393, ISSN: 0960-894X.
Mehrotra et al., "Design and Preparation of Serine-Threonine Protein Phosphatase-inhibitors Based Upon the Nodularin and Microcystin Toxin Structures. Part 1. Evaluation of Key Inhibitory Features and Synthesis of a Rationally Stripped-down Nodularin Macrocycle," Journal of the Chemical Society, Perkin Transactions 1: Organic and Bio-Organic Chemistry, 1997, 17, pp. 2495-2511, ISSN: 0300-922X.
Miyashita et al, "Synthetic Studies on Fostriecin and Related Natural Products," Yuki Gosei Kagaku Kyokaishi, 2007, 65(9), pp. 874-887, ISSN: 0037-9980. (English language abstract included on first page of document).
Moller et al., "Okadaic Acid-induced, Naringin-sensitive Phosphorylation of Glycine N-methyltransferase in Isolated Rat Hepatocytes," Biochemical Journal, 2003, 373(2), pp. 505-513, ISSN: 0264-6021.
Mumby, "The 3D Structure of Protein Phosphatase 2A: New Insights into a Ubiquitous Regulator of Cell Signaling," ACS Chemical Biology, 2007, 2(2), pp. 99-103, ISSN: 1554-8929.
Nebesny et al., "Effect of the Roasting Method on the Content of 5-Hydroxytryptamides of Carboxylic Acids in Roasted Coffee Beans," Nahrung, 2002, 46(4), pp. 279-282.
Nien et al., "Overexpression of the mTOR Alpha4 Phosphoprotein Activates Protein Phosphatase 2A and Increases Statα Binding to PIAS1," Molecular and Cellular Endocrinology, 2007, 263(1-2), pp. 10-17, ISSN: 0303-7207.
Nunbhakdi-Craig et al., "Expression of Protein Phosphatase 2A Mutants and Silencing of the Regulatory Bα Subunit Induce a Selective Loss of Acetylated and Detyrosinated Microtubules," Journal of Neurochemistry, 2007, 101(4), pp. 959-971, ISSN: 0022-3042.
O'Donnell et al., "Serine-threonine Protein Phosphatase Inhibitors Derived from Nodularin: Role of the 2-methyl and 3-diene Groups in the Adda Residue and the Effect of Macrocyclic Conformational Restraint," Journal of the Chemical Society, Perkin Transactions 1, 2001, 14, 1696-1708, ISSN: 1472-7781.
Ogawa et al., "Asymmetric Synthesis of Calyculin C. 2. Synthesis of the C26-C37 Fragment and Model Wittig Couplings," Journal of Organic Chemistry, 1996, 61(18), pp. 6153-6161, ISSN: 0022-3263.
Ogawa et al., "Total Synthesis of Calyculin C," Journal of the American Chemical Society, 1998, 120(48), pp. 12435-12442, ISSN: 0002-7863.
Ogris et al., "A Protein Phosphatase Methylesterase (PME-1) is One of Several Novel Proteins Stably Associating with Two Inactive Mutants of Protein Phosphatase 2A," Journal of Biological Chemistry, 1999, 274(20), pp. 14382-14391, ISSN: 0021-9258.
Oikawa et al., "Synthetic Study of Tautomycetin and Biological Activity of Tautomycin Derivatives," Tennen Yuki Kagobutsu Toronkai Koen Yoshishu, 1997, 39th, pp. 433-438. (English language abstract included on first page of document).
Oikawa, "Synthesis of Specific Protein Phosphatase Inhibitors, Tautomycin and Tautomycetin Toward Structure-activity Relationship Study," Current Medicinal Chemistry, 2002, 9(22), pp. 2033-2054, ISSN: 0929-8673.
Ortega-Gutierrez et al., "Targeted Disruption of the PME-1 Gene Causes Loss of Demethylated PP2A and Perinatal Lethality in Mice," PLoS One, 2008, 3(7), e2486, pp. 1-9, ISSN: 1932-6203.
Paterson et al, "Total Synthesis of Spirastrellolide a Methyl Ester-part 1: Synthesis of an Advanced C17-C40 Bis-spiroacetal Subunit," Angewandte Chemie, International Edition, 2008, 47(16), pp. 3016-3020, ISSN: 1433-7851.
Peng et al., "Induction of Apoptosis by Norcantharidin in Human Colorectal Carcinoma Cell Lines: Involvement of the CD95 Receptor/Ligand," Journal of Cancer Research and Clinical Oncology, 2002, 128(4), pp. 223-230, ISSN: 0171-5216.
Pihko et al., "Synthesis of the C26-C32 Oxazole Fragment of Calyculin C: A Test Case for Oxazole Syntheses," Journal of Organic Chemistry, 1998, 63(1), pp. 92-98, ISSN: 0022-3263.

(56) References Cited

OTHER PUBLICATIONS

Rajagopalan et al., "Molecular Biology of C4 Phosphoenolpyruvate Carboxylase: Structure, Regulation and Genetic Engineering," Photosynthesis Research, 1994, 39(2), pp. 115-135, ISSN: 0166-8595.

Sakoff et al., "Anticancer Activity and Protein Phosphatase 1 and 2A Inhibition of a New Generation of Cantharidin Analogues," Investigational New Drugs, 2002, 20(1), pp. 1-11, ISSN: 0167-6997.

Salit et al, "Synthetic Studies Toward Cytostatin, a Natural Product Inhibitor of Protein Phosphatase 2A," Tetrahedron, 2008, 64(28), pp. 6684-6697, ISSN: 0040-4020.

Scarlato et al., "Asymmetric Synthesis of Calyculin C. 1. Synthesis of the C1-C25 Fragment," Journal of Organic Chemistry, 1996, 61(18), pp. 6139-6152, ISSN: 0022-3263.

Schwartz et al., "Hyperosmotic Stress Contributes to Mouse Colonic Inflammation through the Methylation of Protein Phosphatase 2A," American Journal of Physiology, 2008, 295(5, Pt. 1), pp. G934-G941, ISSN: 0002-9513.

Shibasaki et al, "Synthetic Strategies of Fostriecin," Heterocycles, 2005, 66(1), pp. 727-741, ISSN: 0385-5414.

Sontag et al., "Downregulation of Protein Phosphatase 2A Carboxyl Methylation and Methyltransferase May Contribute to Alzheimer Disease Pathogenesis," Journal of Neuropathology and Experimental Neurology, 2004, 63(10), pp. 1081-1091, ISSN: 0022-3069.

Sontag et al., "Protein Phosphatase 2A Methyltransferase Links Homocysteine Metabolism with Tau and Amyloid Precursor Protein Regualtion," Journal of Neuroscience, 2007, 27(11), pp. 2751-2759, ISSN: 0270-6474.

Studer et al., "Quantitative HPTLC Determination of Carbon-5-Hydroxytryptamides and -Tryptamines in Food Products," Journal of High Resolution Chromatography & Chromatography Communications, Oct. 1982, vol. 5(No. 10358), pp. 581-582.

Sunahori et al., "Methylation Status of CpG Islands Flanking a cAMP Response Element Motif on the Protein Phosphatase 2Acα Promoter Determines CREB Binding and Activity," Journal of Immunology, 2009, 182(3), pp. 1500-1508, ISSN: 0022-1767.

Swiatek et al., "Biochemical Characterization of Recombinant Subunits of Type 2A Protein Phosphatase Overexpressed in *Pichia pastoris*," European Journal of Biochemistry, 2000, 267(16), pp. 5209-5216, ISSN: 0014-2956.

Taylor et al., "Potent Non-peptidyl Inhibitors of Protein Tyrosine Phosphatase 1B," Bioorganic & Medicinal Chemistry, 1998, 6(9), pp. 1457-1468, ISSN: 0968-0896.

Taylor et al., "Potent Non-peptidyl Inhibitors of Protein Tyrosine Phosphatase 1 B. [Erratum to document cited in CA130:3892]," Bioorganic & Medicinal Chemistry, 1998, 6(11), pp. 2235, ISSN: 0968-0896.

Tolstykh et al., "Carboxyl Methylation Regulates Phosphoprotein Phosphatase 2A by Controlling the Association of Regulatory B Subunits," EMBO Journal, 2000, 19(21), pp. 5682-5691, ISSN: 0261-4189.

Travesa et al., "Distinct Phosphatases Mediate the Deactivation of the DNA Damage Checkpoint Kinase Rad53," Journal of Biological Chemistry, 2008, 283(25), pp. 17123-17130, ISSN: 0021-9258.

Turowski et al., "Differential Methylation and Altered Conformation of Cytoplasmic and Nuclear Forms of Protein Phosphatase 2A During Cell Cycle Progression," Journal of Cell Biology, 1995, 129(2), pp. 397-410, ISSN: 0021-9525.

Webster et al., "Design and Preparation of Serine-Threonine Protein Phosphatase Inhibitors Based Upon the Nodularin and Microcystin Toxin Structures. Part 3," Journal of the Chemical Society, Perkin Transactions 1, 2001, 14, pp. 1673-1695, ISSN: 1472-7781.

Wei et al., "Carboxymethylation of the PP2A Catalytic Subunit in *Saccharomyces cerevisia* is Required for Efficient Interaction with the B-type Subunits Cdc55p and Rts1p," Journal of Biological Chemistry, 2001, 276(2), pp. 1570-1577, ISSN: 0021-9258.

Wiart et al., "Sesquiterpenes and Alkaloids from Scorodocarpus Borneensis," Phytochemistry, 2001, 58(4), pp. 653-656.

Williams et al., "Spirastrellolide a: a Revised Structure, Progress Toward the Relative Configuration, and Inhibition of Protein Phosphatase 2A," Organic Letters, 2004, 6(15), pp. 2607-2610, ISSN: 1523-7060.

Wurziger at al., "Hydroxytrypatamides of Green and Roasted Coffee Beans," Presented at Association Scientifique Internationale du Cafe, 4th International Colloquium on the Chemistry of Coffee, 1969, pp. 85-91. (English language title included on Appendix A).

Wurziger et al., "Chemistry of Cocoa. Carboxylic Acid-5-Hydroxytryptamide in Cocoa Beans," Hyg. Inst., Gordian, 1970, 70(1643), Part 1: pp. 376, 378. (English language abstract inlcuded on first page of document).

Wurziger et al., "Chemistry of Cocoa. Carboxylic Acid-5-Hydroxytryptamide in Cocoa Beans," Hyg. Inst., Gordian, 1970, 70(1644), Part 2: pp. 438-440. (English language abstract included on first page of reference C117).

Wurziger et al., "Chemistry of Cocoa. Carboxylic Acid-5-Hydroxytryptamide in Cocoa Beans," Hyg. Inst., Gordian, 1970, 70(1645), Part 3: pp. 470, 473. (English language abstract included on first page of reference C117).

Xie et al., "An Enzymic Activity in Bovine Brain that Catalyzes the Reversal of the C-terminal Methyl Esterification of Protein Phosphatase 2A," Biochemical and Biphysical Research Communications, 1994, 203(3), pp. 1710-1715, ISSN: 0006-291X.

Xie et al., "Protein Phosphatase 2A is Reversibly Modified by Methyl Esterification at its C-terminal Leucine Residue in Bovine Brain," Journal of Biological Chemistry, 1994, 269(3), pp. 1981-1984, ISSN: 0021-9258.

Xing et al., "Structural Mechanism of Demethylation and Inactivation of Protein Phosphatase 2A," Cell, 2008, 133(1), pp. 154-163, ISSN: 0092-8674.

Yang et al., "S-adenosylemthionine and its Metabolite Induce Apoptosis in HepG2 Cells: Role of Protein Phosphatase 1 and Bcl-xS," Hepatology, 2004, 40(1), pp. 221-231, ISSN: 0270-9139.

Yoo et al., "The α4-containing Form of Protein Phosphatase 2A in Liver and Hepatic Cells," Journal of Cellular Biochemistry, 2008, 105(1), pp. 290-300, ISSN: 0730-2312.

Yoon et al., "Methotrexate Decreases PP2A Methylation and Increases Tau Phosphorylation in Neuron," Biochemical and Biophysical Research Communications, 2007, 363(3), pp. 811-816, ISSN: 0006-291X.

Yu et al., "Methylation of the Protein Phosphatase 2A Catalytic Subunit is Essential for Association of Bα Regulatory Subunit but not SG2NA, Striatin, or Polyomavirus Middle Tumor Antigen," Molecular Biology of the Cell, 2001, 12(1), pp. 185-199, ISSN: 1059-1524.

Zhang et al., "Homocysteine Induces Tau Phosphorylation by Inactivating Protein Phosphatase 2A in Rat Hippocampus," Neurobiology of Aging, 2008, 29(11), pp. 1654-1665, ISSN: 0197-4580.

Zhou et al., "Tau Hyperphosphorylation Correlates with Reduced Methylation of Protein Phosphatase 2A," Neurobiology of Disease, 2008, 31(3), pp. 386-394, ISSN: 0969-9961.

Peter Folstar et al. (1980) "New Tryptamine Derivatives Isolated from Wax of Green Coffee Beans." Journal of Agricultural and Food Chemistry, vol. 28, No. 4, 872-874.

Roman Lang et al. (2005) "A Versatile Method for the Quantitative Determination of beta-N-alkanoyl-5-hydroxytryptamides in Roasted Coffee." European Food Research Technology, vol. 220, 638-643.

G. Webster Ross et al. (2000) "Association of Coffee and Caffeine Intake With the Risk of Parkinson Disase ." Journal of the American Medical Association, vol. 283, No. 20, 2674-2679.

Galpern, W. R. et al., "Interface between tauopathies and synucleopathies: A tale of two proteins", Annals of Neurology, 2006, 59 (3): 449-458.

Avila, J. S. et al., "Role of Tau protein in both physiological and pathological conditions", Physiol. Rev., 2004, 84: 361-384.

Clark, L. N. et al., "Pathogenic implications of mutations in the tau gene in pallido-ponto-nigral degeneration and related neurodegenerative disorders linked to chromosome 17", Proc. Natl. Acad. Sci. USA, 1998, 95: 13103-13107.

(56) References Cited

OTHER PUBLICATIONS

Schmidt, M. et al., "Tau isoform profile and phosphorylation state in dementia pugilistica recapitulate Alzheimer's disease",. Acta Neuropathologica, 2001, 101(5):518-524.

Lippa, C. F. et al., "Antibodies to alpha-synuclein detect Lewy bodies in many Down's syndrome brains with Alzheimer's disease",. Annals of Neurology, 1999, 45(3): 353-357.

Hanger, D. P. et al., "Tau in Alzheimer's disease and Down's syndrome is insoluble and abnormally phosphorylated",. Biochem. J., 1991, 275(Pt. 1): 99-104.

Piao, Y. S. et al., "Co-localization of alpha-synuclein and phosphorylated tau in neuronal and glial cytoplasmic inclusions in a patient with multiple system atrophy of long duration",. Acta Neuropathol., 2001, 101(3): 285-293.

Mukaetova-Ladinska, E. B. et al., "Alpha-synuclein inclusions in Alzheimer and Lewy body diseases",. J. Neuropathol., 2000, 59(5): 408-417.

Iseki, E. et al., "Dementia with Lewy bodies from the perspective of tauopathy",. Acta Neuropathol., 2003, 105(3): 265-270.

Hashimoto, M. et al., "The Role of alpha-synuclein assembly and metabolism in the pathogenesis of Lewy body disease",. J. Mol. Neurosci., 2004, 24(3): 343-352.

Fujiwara H, et al. "Alpha-Synuclein is phosphorylated in synucleinopathy lesions" Nat Cell Biol. 2002, 4:160-164.

Vafai, S., and Stock, J.B."Protein phosphatase 2A methylation: a link between elevated plasma homocysteine and Alzheimer's Disease", 2002, FEBS Lett. 518: 1-4.

* cited by examiner

Figure 1

| Example Number | Base | | | | Coupling Agent | | | | Solvent | Yield (%) | Purity |
|---|---|---|---|---|---|---|---|---|---|---|---|
| | Pyridine | TEA | TEA/ Pyridine | NaHCO₃ (aq.) | DIEA | HATU | SOCl₂ | PyBOP | | | |
| 1 | x | | | | | x | | | Pyridine | 50 | >95% |
| 2 | x | | | | | x | | | Pyridine | 50 | >95% |
| 3 | x | | | | | | - | | Pyridine | 67 | >95% |
| 4 | x | | | | | | - | | Pyridine | 53 | >95% |
| 6 | x | | | | | | - | | Pyridine | 75 | >95% |
| 7 | x | | | | | | | | Pyridine | 81 | >95% |
| 9 | | x | | | | x | | | DCM | 65 | 80% |
| 10 | | x | | | | x | | | DCM | 71 | >95% |
| 11 | | x | | | | x | | | DCM | 54 | >95% |
| 12 | | x | | | | x | | | DCM | 75 | 90% |
| 14 | | x | | | | x | | | DCM | 74 | >95% |

Figure 2
Experimental Data: Process for Making Compound I-63

| Experiment I.D. | Base | | | | | Coupling Agent | | | Solvent | | | | | Yield (%) | Purity |
|---|---|---|---|---|---|---|---|---|---|---|---|---|---|---|---|
| | Pyridine | TEA | TEA/Pyridine | NaHCO$_3$ (aq.) | DIEA | HATU | SOCl$_2$ | PyBOP | DCM | DMF | THF | DCM+DMF | DMF+THF | | |
| A | x | | | | | | x | | x | | | | | 83 | 50 |
| B | x | | | | | | | x | x | | | | | 81 | 75 |
| C | x | | | | | x | | | x | | | | | 73 | 80 |
| D | | | | x | | | x | | x | | | | | 65 | 50 |
| E | | | x | | | x | | | | x | | | | 88 | >95 |
| F | x | | | | | | x | | | | | x | | 79 | 85 |
| G | | | | | x | | x | | | | x | | | 75 | 80 |
| H | | | | | x | x | | | | | | | x | 92 | >95 |
| I | | | | | x | | | x | | | | | x | 87 | >95 |
| J | | x | | | | | | x | | | | | x | 85 | >95 |

COMPOUNDS, COMPOSITIONS AND METHODS FOR MAKING THE SAME

RELATED APPLICATIONS

This application claims priority to U.S. provisional patent application Ser. No. 61/124,949, filed Apr. 21, 2008; U.S. provisional patent application Ser. No. 61/125,205, filed Apr. 23, 2008; and U.S. provisional patent application Ser. No. 61/127,900, filed May 16, 2008, the entire disclosure of each of which is incorporated herein by reference.

BACKGROUND

Protein phosphatase 2A ("PP2A") is a ubiquitous and conserved serine/threonine phosphatase with broad substrate specificity and diverse cellular functions. PP2A typically exists as heterotrimers comprising of catalytic C—, structural or scaffold A- and regulatory B-type subunits, belonging to the B, B', B" and B'" families. In vivo, a major proportion of the A- and C-subunits form a stable heterodimer, which is also referred to as the core enzyme. (see Price, N. E., and Mumby, M. C. *Biochemistry* 39, 11312-11318 (2000)). The B-type subunits direct substrate-specificity and sub-cellular localization. The heterotrimeric holoenzyme assembly with specific B-type subunits results in PP2A specificity, in the modulation of kinetic properties of PP2A to different substrates (see Price, N. E., and Mumby, M. C. *Biochemistry* 39, 11312-11318 (2000)) and therefore is likely to affect PP2A enzyme activity towards those substrates.

The alpha-carboxyl of the C-terminal leucine residue of the catalytic subunit of PP2A is subject to reversible methyl esterification and methyl-ester hydrolysis, and the methylation state of PP2A regulates heterotrimer assembly. [see Tokstykh, T. et al., *EMBO J.* 19 (21): 5682-91 (2000); Wu, J. et al., *EMBO J.* 19 (21): 5672-81 (2000); Wei, H. et al. *J. Biol. Chem.* 276 (2): 1570-77 (2001); and Yu, X. X. et al., *Mol. Biol. Cell* 12 (1): 185-99 (2001)]. The carboxyl methylation requires an S-adenosyl-methionine (SAM) dependent methyltransferase (MT, MTase, LCMT or PPMT) (see Lee, J., and Stock, J. *J. Biol. Chem.* 268, 19192-19195 (1993)), which recognizes SAM and the AC heterodimer or the heterotrimeric holoenzyme (but not C subunit alone) as substrates. Methylated PP2A is demethylated by a specific methylesterase (ME, MEase, PME1 or PPME) (see Lee, J., Chen, Y., Tolstykh, T., and Stock, J. *P.N.A.S. U.S.A.* 93, 6043-6047. (1996)).

As a universal regulator of cellular functions, PP2A is essential for normal biological activities. Malfunction of PP2A is associated with a wide variety of disease conditions. Alterations in PP2A methylation and/or activity are associated with various disorders, diseases, and conditions, including, among others, neurological disorders, neurodegenerative diseases, diabetes, insulin resistance, and metabolic syndrome.

Isolated and purified with anamides and with anolides are described in U.S. Pat. No. 7,282,593. United States Patent Publication No. 2007/0197629 describes melatonin analogs which act suppressively on both osteoblasts and osteoclasts. U.S. Pat. No. 5,714,094 describes an antioxidant composition and a process of recovering the same from a gelatinous retentate of spent ground coffee oil. U.S. Pat. No. 4,939,174 describes the formation of a prodrug from a fatty acid carrier and a neuroactive drug.

SUMMARY OF THE INVENTION

The present invention provides compounds and/or compositions that modulate PP2A activity. Certain compounds of interest can be isolated from naturally-occurring sources (see, for example, U.S. Provisional patent application Ser. Nos. 61/124,949; 61/125,205; and 61/125,169; United States Patent Publication number 2006/0171938; and United States Patent Publication number 2008/0213406; and Application number PCT/US06/003686); and/or certain compounds can be synthesized (see for example, U.S. Provisional patent application Ser. No. 61/127,900, each of which is incorporated herein by reference.

It has been discovered that certain compounds of the formulae described herein (e.g., formula I, Ia, Ib, Ic, Id, Ie, If, Ig and/or Ih), and its classes and subclasses as described herein modulate the activity of PP2A. Compounds that modulate the activity of PP2A may be useful for treating various diseases and/or disorders, e.g., neurodegenerative disorders, diabetes and metabolic disorders. In some embodiments, such compounds modulate PP2A activity directly; in some embodiments, such compounds modulate PP2A activity indirectly. In some embodiments, such compounds modulate PP2A methylation status. In some embodiments, such compounds modulate activity of PP2A methyltransferase; in some embodiments, such compounds modulate activity of PP2A methylesterase.

The present invention additionally provides synthetic technologies that allow preparation of compounds of interest. Synthetic technologies may be used to prepare compounds that also occur in nature, but importantly also provide access to other compounds of related chemical structures (see, for example, U.S. Provisional patent application Ser. No. 61/127,900), which is incorporated herein by reference.

The present invention thus provides compounds, compositions, and/or methods of their preparation or use in the treatment of any of a variety of disorders, diseases, or conditions. In some embodiments, the present invention provides compounds, compositions, and/or methods of their preparation or use in the treatment of one or more diseases, disorders, or conditions associated with abnormal levels of PP2A methylation and/or abnormal PP2A phosphatase activity.

In some embodiments the present invention provides compounds, compositions, and/or methods of their preparation or use in the treatment of, for example certain neurological disorders, neurodegenerative diseases, diabetes, insulin resistance, and/or metabolic syndrome.

Provided compounds and compositions, whether synthetic or natural, that modulate PP2A activity (e.g., compounds that modulate the methylation of PP2A, compounds that modulate the demethylation of PP2A, compounds that modulate the interaction of PP2A substrates with PP2A, compounds that modulate the interaction of auxiliary proteins with PP2A and/or compounds that directly interact with PP2A, etc.) are also contemplated. In certain embodiments, such compounds and compositions maximize the inhibition of methylesterase while minimizing the inhibition of methyltransferase and/or hinder methyltransferase and/or PP2A.

Compounds useful in accordance with the present invention include those of formula I and its various classes and subclasses depicted

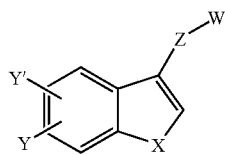

I or a pharmaceutically acceptable salt thereof, wherein:
Z is selected from the group consisting of:

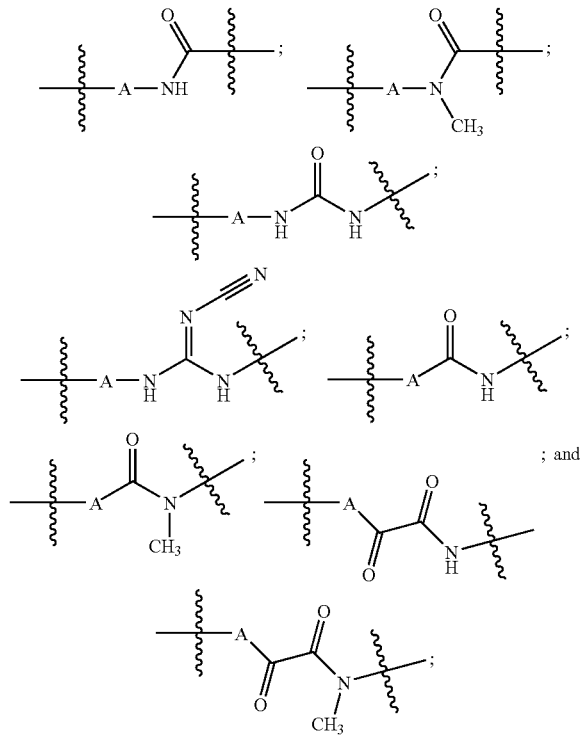

A is —$(CH_2)_n$— wherein n is 0, 1 or 2;
X is NH, NR', O, or S;
W is a linear or branched, saturated or unsaturated alkyl having between 10 and 25 carbons, optionally containing 1 or 2 heteroatoms selected from NH, NR' or O, and optionally substituted with one or more —OR groups or halogen;
Y is selected from H, —OH, —R, —OR, —$NH_2$, —NHR', —NR'R', —C(O)NHR', —C(O)NR'R', halogen, or a saccharide;
Y' is selected from H, —OH, —R, —OR, —$NH_2$, —NHR', —NR'R', —C(O)NHR', —C(O)NR'R', halogen, or a saccharide;
R is H, an optionally substituted —$C_{1-6}$ alkyl which may be linear, cyclic, or branched, an optionally substituted —$C_6$ aromatic, an optionally substituted 5- or 6-membered heteroaromatic ring, —C(O)R', —C(O)H, —C(O)OR', —C(O)OH, —C(N)NH, or —C(N)NR'; and
R' is an optionally substituted $C_1$-$C_6$ alkyl or alkenyl group which may be linear, cyclic, or branched;
or R and R' may be taken together to form a saturated 5-6 membered heterocyclic ring having 1-2 heteroatoms selected from oxygen or nitrogen.

In some embodiments, a compound provided herein is not naturally occurring.

In some embodiments, when Z is

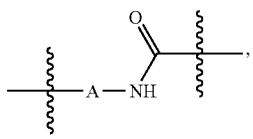

then n is not 0.

In some embodiments, a compound provided herein is characterized by an ability to modulate PP2A methylation, such that at least one of the following conditions is met:
(i) when the compound is incubated with purified PP2A and purified MT, the compound modulates methylation of PP2A with an $IC_{50}$ below 100 μM;
(ii) when the compound is incubated with purified PP2A and purified ME, the compound modulates demethylation of PP2A with an $IC_{50}$ below 100 μM;
(iii) when the compound is separately incubated with purified PP2A and purified MT; and
    purified PP2A and purified ME;
    the compound shows selective activity towards MTase as compared with MEase.
(iv) when the compound is separately incubated with purified PP2A and purified MT; and
    purified PP2A and purified ME;
    the compound shows selective activity towards MEase as compared with MTase; and/or
(v) when the compound is incubated with purified PP2A, purified ME, and purified MT, methylation of PP2A is observed at a different level than is observed under comparable conditions without the compound;

In some embodiments, at least one of the following conditions is met with respect to a provided compound:
(i) the compound is further characterized in that, when the compound is incubated with isolated PP2A and an isolated non-protein PP2A target in the absence of MT and ME, observed phosphorylation of the isolated non-protein target to that observed without the compound; and/or
(ii) the compound is further characterized in that, when the compound is incubated with isolated PP2A and an isolated protein PP2A target in the absence of MT and ME, observed phosphorylation of the isolated protein target compares to that observed without the compound;

In some embodiments, a compound provided herein is provided in the form of a pharmaceutically acceptable salt of a compound of formula I and/or its various classes and subclasses depicted herein.

Compounds useful in accordance with the present invention include those of formula I and its various classes and subclasses depicted herein.

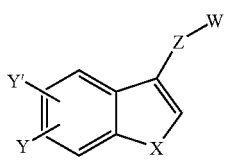

I or a pharmaceutically acceptable salt thereof, wherein:
Z is selected from the group consisting of:

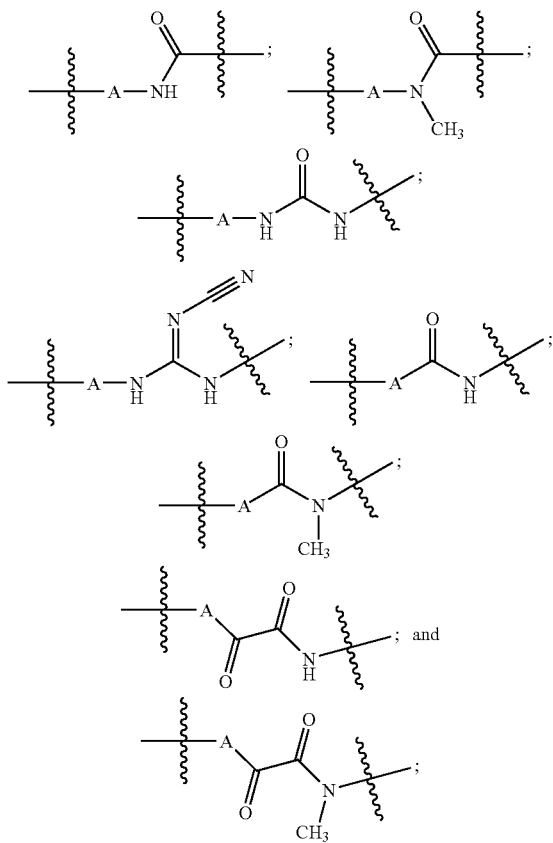

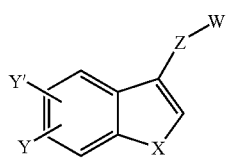

A is —(CH$_2$)$_n$, or —(CB$_2$)$_n$, wherein n is 0, 1 or 2;
B is H, —NHC(=O)OR, or —C(=O)OR;
X is NH, NR', O, or S;
W is a linear or branched, saturated or unsaturated alkyl having between 10 and 25 carbons, optionally containing 1 or 2 heteroatoms selected from NH, NR' or O, and optionally substituted with one or more —OR groups or halogen;
Y and Y' are independently selected from H, —OH, —R, —OR, —NH$_2$, —NHR', —NR'R', —NHR", —C(O)NHR', —C(O)NR'R', halogen, or a saccharide;
—R is H, —C$_{1-6}$ alkyl which may be linear, cyclic, or branched, —C$_6$ aromatic, a 5- or 6-membered heteroaromatic ring, —C(O)R', —C(O)H, —C(O)OR', —C(O)OH, —C(N)NH, —C(N)NR'; and
—R' is a C$_1$-C$_6$ alkyl or alkenyl group which may be linear, cyclic, or branched;
—R" is a —C$_{1-2}$ alkyl optionally substituted with —OH.
Compounds useful in accordance with the present invention include those of formula I and its various classes and subclasses depicted.

I

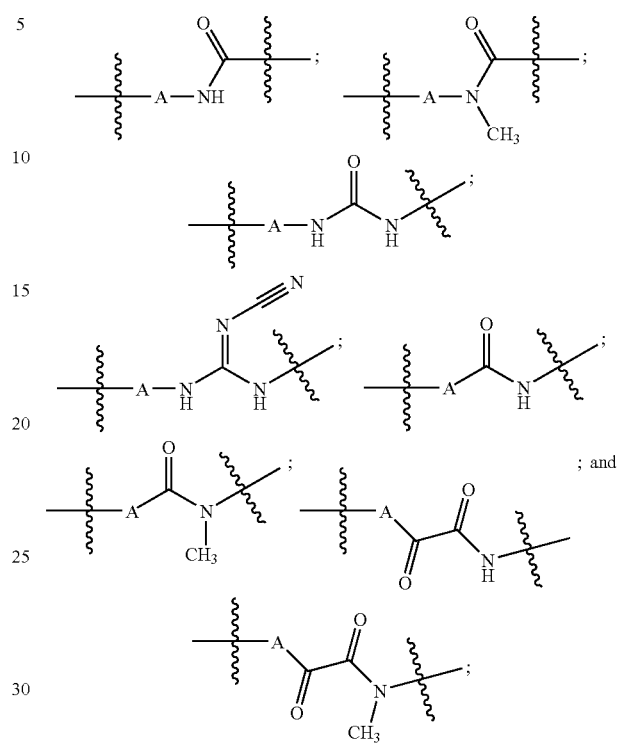

or a pharmaceutically acceptable salt thereof, wherein:
Z is selected from the group consisting of:

A is —(CH$_2$)$_n$, or —(CB$_2$)$_n$, wherein n is 0, 1 or 2;
B is H, —NHC(=O)OR, or —C(=O)OR;
X is NH, NR', O, or S;
W is a linear or branched, saturated or unsaturated alkyl having between 10 and 25 carbons, optionally containing 1 or 2 heteroatoms selected from NH, NR' or O, and optionally substituted with one or more —OR groups or halogen;
Y and Y' are independently selected from H, —OH, —R, —OR, —NH$_2$, —NHR', —NR'R', —NHR", —C(O)NHR', —C(O)NR'R', halogen, or a saccharide;
—R is H, —C$_{1-6}$ alkyl which may be linear, cyclic, or branched, —C$_6$ aromatic, a 5- or 6-membered heteroaromatic ring, —C(O)R', —C(O)H, —C(O)OR', —C(O)OH, —C(N)NH, —C(N)NR'; and
—R' is a C$_1$-C$_6$ alkyl or alkenyl group which may be linear, cyclic, or branched;
—R" is a —C$_{1-2}$ alkyl optionally substituted with —OH.
In some embodiments, (a) the compound is not naturally occurring and/or (b) the compound is characterized by an ability to modulate PP2A methylation, such that at least one of the following conditions is met:
(i) when the compound is incubated with purified PP2A and purified MT, the compound modulates methylation of PP2A with an IC$_{50}$ below 100 μM;
(ii) when the compound is incubated with purified PP2A and purified ME, the compound modulates demethylation of PP2A with an IC$_{50}$ below 100 μM;
(iii) when the compound is separately incubated with purified PP2A and purified MT; and
purified PP2A and purified ME;
the compound shows selective activity towards MTase as compared with MEase.

(iv) when the compound is separately incubated with
purified PP2A and purified MT; and
purified PP2A and purified ME;
the compound shows selective activity towards MEase as compared with MTase; and/or
(v) when the compound is incubated with purified PP2A, purified ME, and purified MT, methylation of PP2A is observed at a different level than is observed under comparable conditions without the compound;
and/or (c) the compound is further characterized in that, when the compound is incubated
with isolated PP2A and an isolated non-protein PP2A target in the absence of MT and ME, observed phosphorylation of the isolated non-protein target compares to that observed without the compound; and/or (d) wherein the compound is further characterized in that, when the compound is incubated with isolated PP2A and an isolated protein PP2A target in the absence of MT and ME, observed phosphorylation of the isolated protein target compares to that observed without the compound;
or a pharmaceutically acceptable salt thereof.

Isolated compounds useful in accordance with the present invention include those of formula I and its various classes and subclasses depicted herein

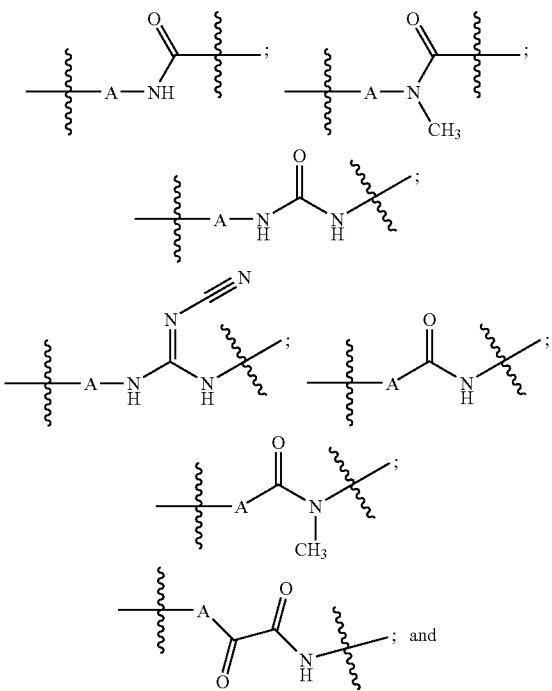

or a pharmaceutically acceptable salt thereof, wherein:
Z is selected from the group consisting of:

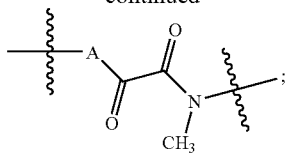

A is —(CH$_2$)$_n$, wherein n is 0, 1 or 2;
X is NH, NR', O, or S;
W is a linear or branched, saturated or unsaturated alkyl having between 10 and 25 carbons, optionally containing 1 or 2 heteroatoms selected from NH, NR' or O, and optionally substituted with one or more —OR groups or halogen;
Y and Y' are independently selected from H, —OH, —R, —OR, —NH$_2$, —NHR', —NR'R', —C(O)NHR', —C(O)NR'R', halogen, or a saccharide;
R is H, —C$_{1-6}$ alkyl which may be linear, cyclic, or branched, —C$_6$ aromatic, a 5- or 6-membered heteroaromatic ring, —C(O)R', —C(O)H, —C(O)OR', —C(O)OH, —C(N)NH, —C(N)NR'; and
R' is a C$_1$-C$_6$ alkyl or alkenyl group which may be linear, cyclic, or branched; and
(a) when Z is

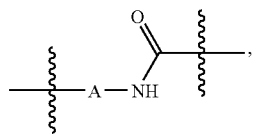

then n is not 0.

In some embodiments, (b) the compound is characterized by an ability to modulate PP2A methylation, such that at least one of the following conditions is met:
(i) when the compound is incubated with purified PP2A and purified MT, the compound modulates methylation of PP2A with an IC$_{50}$ below 100 μM;
(ii) when the compound is incubated with purified PP2A and purified ME, the compound modulates demethylation of PP2A with an IC$_{50}$ below 100 μM;
(iii) when the compound is separately incubated with
purified PP2A and purified MT; and
purified PP2A and purified ME;
the compound shows selective activity towards MTase as compared with MEase.
(iv) when the compound is separately incubated with
purified PP2A and purified MT; and
purified PP2A and purified ME;
the compound shows selective activity towards MEase as compared with MTase; and/or
(v) when the compound is incubated with purified PP2A, purified ME, and purified MT, methylation of PP2A is observed at a different level than is observed under comparable conditions without the compound; and/or
(c) the compound is characterized in that, when the compound is incubated
with isolated PP2A and an isolated non-protein PP2A target in the absence of MT and ME, observed phosphorylation of the isolated non-protein target compares to that observed without the compound; and/or (d) the compound is characterized in that, when the compound is incubated with isolated PP2A and an isolated protein PP2A target in the absence of MT and ME, observed phosphorylation of the isolated protein target compares to that observed without the compound;
or a pharmaceutically acceptable salt thereof.

Compositions useful in accordance with the present invention include those of formula I and its various classes and subclasses depicted herein

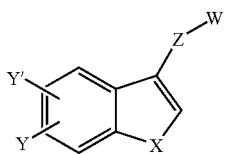

I or a pharmaceutically acceptable salt thereof, wherein:
Z is selected from the group consisting of:

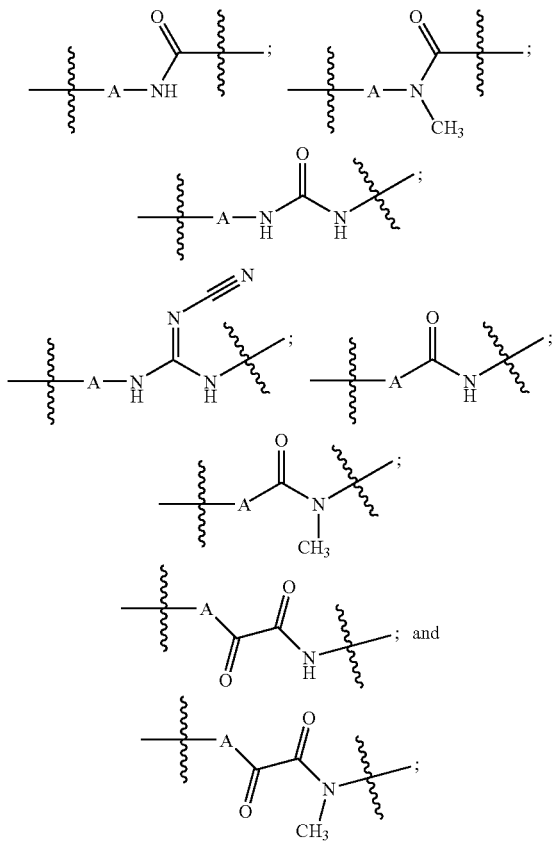

A is —(CH$_2$)$_n$, or —(CB$_2$)$_n$ wherein n is 0, 1 or 2;
B is H, —NHC(=O)OR', or —C(=O)OR;
X is NH, NR', O, or S;
W is a linear or branched, saturated or unsaturated alkyl having between 10 and 25 carbons, optionally containing 1 or 2 heteroatoms selected from NH, NR' or O, and optionally substituted with one or more —OR groups or halogen;
Y and Y' are independently selected from H, —OH, —R, —OR, —NH$_2$, —NHR', —NR'R', —NHR", —C(O)NHR', —C(O)NR'R', halogen, or a saccharide;
—R is H, —C$_{1-6}$ alkyl which may be linear, cyclic, or branched, —C$_6$ aromatic, a 5- or 6-membered heteroaromatic ring, —C(O)R', —C(O)H, —C(O)OR', —C(O)OH, —C(N)NH, —C(N)NR'; and —R' is a C$_1$-C$_6$ alkyl or alkenyl group which may be linear, cyclic, or branched;
—R" is a —C$_{1-2}$ alkyl optionally substituted with —OH;
In some embodiments (a) the compound is not naturally occurring; and/or (b) when Z is

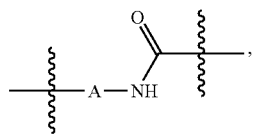

then n is not 0; and/or (c) the compound is characterized by an ability to modulate PP2A methylation, such that at least one of the following conditions is met:
(i) when the compound is incubated with purified PP2A and purified MT, the compound modulates methylation of PP2A with an IC$_{50}$ below 100 μM;
(ii) when the compound is incubated with purified PP2A and purified ME, the compound modulates demethylation of PP2A with an IC$_{50}$ below 100 μM;
(iii) when the compound is separately incubated with
purified PP2A and purified MT; and
purified PP2A and purified ME;
the compound shows selective activity towards MTase as compared with MEase.
(iv) when the compound is separately incubated with
purified PP2A and purified MT; and
purified PP2A and purified ME;
the compound shows selective activity towards MEase as compared with MTase; and/or
(v) when the compound is incubated with purified PP2A, purified ME, and purified MT, methylation of PP2A is observed at a different level than is observed under comparable conditions without the compound;
and/or (d) the compound is further characterized in that, when the compound is incubated
with isolated PP2A and an isolated non-protein PP2A target in the absence of MT and ME, observed phosphorylation of the isolated non-protein target compares to that observed without the compound; and/or (e) wherein compound is further characterized in that, when the compound is incubated with isolated PP2A and an isolated protein PP2A target in the absence of MT and ME, observed phosphorylation of the isolated protein target compares to that observed without the compound;
or a pharmaceutically acceptable salt thereof.

In some embodiments, the present provides methods for preparing a compound of the structure:

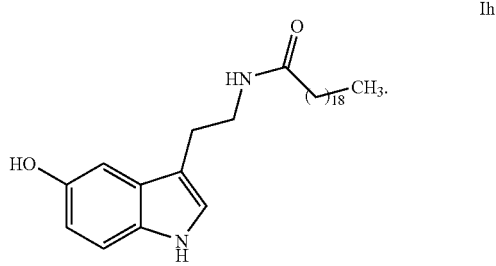

Ih

BRIEF DESCRIPTION OF THE DRAWING

FIG. 1 presents a table summarizing the different reaction conditions utilized to prepare compounds of formula I as set forth in Examples 1-14.

FIG. 2 presents a table summarizing different synthetic conditions that were tested in the preparation of various compounds of the formulae described herein.

DEFINITIONS

Figure 3:
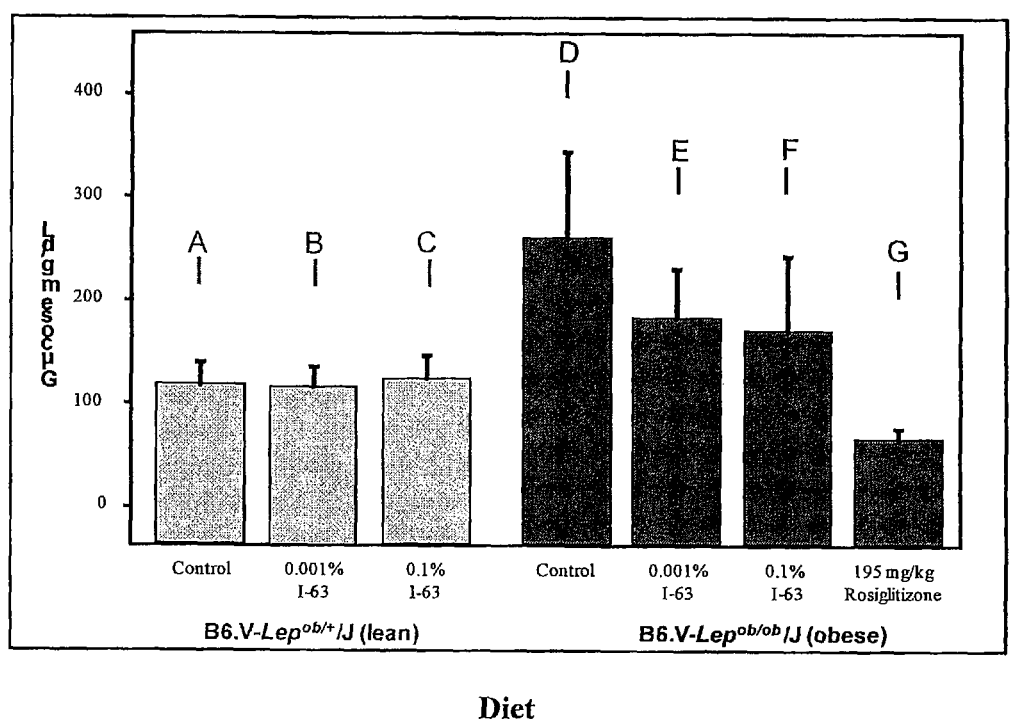
FIG. 3 depicts a bar graph demonstrating that daily administration, over a two week period, of Compound I-63 results in 26-30% reduction in non-fasted blood glucose levels in homozygous obese mice while the anti-diabetic control drug, Rosiglitizone results in 66% reduction in non-fasted glucose levels in homozygous obese mice.

Definitions of specific functional groups and chemical terms are described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Additives: The term "additives" as used herein refers to pharmaceutically acceptable organic or inorganic substances or substances safe to consume which do not deleteriously react with the compositions, are non-toxic, are well-tolerated upon ingestion, and act as carrier materials suitable for administration of the compositions.

Aliphatic: The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched, or unbranched) having 1-6 carbon atoms.

Alkyl, alkenyl, and alkynyl: In certain embodiments, the alkyl, alkenyl, and alkynyl groups employed in the invention contain 10-25 aliphatic carbon atoms. In certain other embodiments, the alkyl, alkenyl, and alkynyl groups employed in the invention contain 12-21 aliphatic carbon atoms. In yet other embodiments, the alkyl, alkenyl, and alkynyl groups employed in the invention contain 15-21 aliphatic carbon atoms. In yet other embodiments, the alkyl, alkenyl, and alkynyl groups employed in the invention contain 15 carbon atoms. In certain embodiments, the alkyl, alkenyl, and alkynyl groups employed in the invention contain 16 carbon atoms. In certain embodiments, the alkyl, alkenyl, and alkynyl groups employed in the invention contain 17 carbon atoms. In certain embodiments, the alkyl, alkenyl, and alkynyl groups employed in the invention contain 18 carbon atoms. In certain embodiments, the alkyl, alkenyl, and alkynyl groups employed in the invention contain 19 carbon atoms. In certain embodiments, the alkyl, alkenyl, and alkynyl groups employed in the invention contain 20 carbon atoms. In certain embodiments, the alkyl, alkenyl, and alkynyl groups employed in the invention contain 21 carbon atoms. In certain embodiments, the alkyl, alkenyl, and alkynyl groups employed in the invention contain 22 carbon atoms In certain embodiments, the alkyl, alkenyl, and alkynyl groups employed in the invention contain 23 carbon atoms In certain embodiments, the alkyl, alkenyl, and alkynyl groups employed in the invention contain 24 carbon atoms In certain embodiments, the alkyl, alkenyl, and alkynyl groups employed in the invention contain 25 carbon atoms Illustrative aliphatic groups thus include, but are not limited to, for example, pentadecyl, hexadecyl, heptadecyl, oxtadecyl, noadecyl, eicosyl, heneicosyl, docosyl, tricosyl, tetracosyl, and pentacosyl.

Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

Alkoxy and alkylthio: The term "alkoxy", or "alkylthio" as used herein refers to an alkyl group, as previously defined, attached to the parent molecule through an oxygen atom or through a sulfur atom. In certain embodiments, the alkyl, alkenyl, and alkynyl groups contain 1-20 aliphatic carbon atoms. In certain other embodiments, the alkyl, alkenyl, and alkynyl groups contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of alkylthio include, but are not limited to, methylthio, ethylthio, propylthio, isopropylthio, n-butylthio, and the like.

Alkylamino: The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contains 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

Some examples of substituents of the aliphatic (and other) moieties of compounds of the invention as described herein include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x$(CO)$R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

Animal: The term "animal", as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). A non-human animal may be a transgenic animal.

Aryl and heteroaryl: In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2 R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

Combination therapy: The term "combination therapy", as used herein, refers to those situations in which two or more different pharmaceutical agents are administered in overlapping regimens so that the subject is simultaneously exposed to both agents. In some embodiments, two or more different pharmaceutical agents administered in combination are administered together in a single composition or unit dosage form. In many embodiments, however, two or more different pharmaceutical agents are administered in combination through administration of separate compositions via overlapping regimens.

Comestible: As used herein, the term "comestible" refers to a material that is suitable for human consumption, including a material that can be ingested by oral and by a non-oral means, e.g., an inhalant or snuff. For purposes of the present invention, the term also includes foods (e.g., beverages) and dietary supplements that are supplemented or enhanced with the compounds of formula I.

Dialkylamino: The term "dialkylamino" refers to a group having the structure —NRR', wherein R and R' are each an aliphatic group, as defined herein. R and R' may be the same or different in a dialkyamino moiety. In certain embodiments, the aliphatic groups contain 1-20 aliphatic carbon atoms. In certain other embodiments, the aliphatic groups contain 1-10 aliphatic carbon atoms. In yet other embodiments, the aliphatic groups employed in the invention contain 1-8 aliphatic carbon atoms. In still other embodiments, the aliphatic groups contain 1-6 aliphatic carbon atoms. In yet other embodiments, the aliphatic groups contain 1-4 aliphatic carbon atoms. Examples of dialkylamino groups include, but are not limited to, dimethylamino, methyl ethylamino, diethylamino, methylpropylamino, di(n-propyl) amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

Extract: The term "extract" refers to a composition prepared from a natural source. Typically, extracts are prepared by contacting the natural source with one or more solvents, such that a portion of the natural material partitions into the solvent and a portion is removed. Serial partition or other separation steps may be performed in the preparation of an extract. As will be appreciated with reference to the present specification, certain compounds described herein are naturally occurring and can be obtained by extraction of a natural source. Naturally occurring compounds described herein may alternatively be prepared by chemical synthesis. Chemically synthesized compounds described herein, whether naturally-occurring or not, may be added to prepared extracts and/or treated together with an extract. In some embodiments, compounds present in extracts are compounds of formulae I, II, III, IV, V, VI, VII, VIII, and/or IX. In some embodiments, compounds present in extracts are compounds of formulae Ia, Ib, Ic, Id, Ie, If, Ig and/or Ib. In some embodiments, compounds present in extracts according to the present invention are naturally occurring compounds. In some such embodiments, the naturally-occurring compounds are of formulae Ia, Ib, Ic, Id, Ie, If, Ig and/or Ih.

Heteroaliphatic: The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments described herein.

Heterocycloalkyl and Heterocycle: The term "heterocycloalkyl" or "heterocycle", as used herein, refers to a non-aromatic 5-, 6-, or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments described herein.

Halo and Halogen: The terms "halo" and "halogen" as used herein refer to an atom selected from fluorine, chlorine, bromine, and iodine.

Haloalkyl: The term "haloalkyl" denotes an alkyl group, as defined above, having one, two, or three halogen atoms attached thereto and is exemplified by such groups as chloromethyl, bromoethyl, trifluoromethyl, and the like.

Independently selected: The term "independently selected" is used herein to indicate that the R groups can be identical or different.

Isolated: The term "isolated", as used herein, means that the isolated entity has been: (i) separated from at least one component with which it was previously associated; and/or (ii) manipulated by the hand of man. In some embodiments, the isolated entity is separated from at least one component with which it was associated when initially produced. When most other components have been removed, the isolated entity is "purified" or "concentrated". Isolation and/or purification and/or concentration may be performed using any techniques known in the art including, for example, distillation, fractionation, gas stripping, extraction, precipitation, or other separation.

Modulate: As used herein, the term "modulate" is used in the following contexts. In certain embodiments, the term "modulate" refers to affecting PP2A activity by the direct interaction with PP2A. In certain embodiments, the term "modulate" refers to affecting PP2A activity indirectly, by: modulating levels of PP2A methylation (which typically includes a combination PP2A methylation and PP2A demethylation), binding of auxiliary proteins, and/or binding of a substrate to PP2A, thereby affecting PP2A activity towards that substrate. Exemplary auxiliary proteins include, but are not limited to, ME, MT, PP2A regulatory B-subunits that belong to the B, B', B" and B'" families, and a PP2A activator, e.g., PTPA. Exemplary substrates include but are not limited to tau, alpha-synuclein, Akt, p38 kinase, PI3 kinase, ERK1/2, IRS1, IRS2, JNK2/3, I-kappa-B (IκB), p70S6K, mTORC1, GSK3β and cdk5. In certain embodiments, the term "modulate" refers to MT activity, wherein such activity results in PP2A methylation and such modulation of MT activity results in a change in PP2A methylation status. For example, change in methylation status results in modulation of PP2A heterotrimeric holoenzyme assembly and/or in modulation of PP2A activity. In certain embodiments, the term "modulate" refers to MT activity by interfering with interaction of PP2A and MT. In certain embodiments, the term "modulate" refers to ME activity, wherein such activity results in PP2A demethylation and such modulation of ME activity results in a change in PP2A methylation status. For example, change in methylation status results in modulation of PP2A heterotrimeric holoenzyme assembly and/or in modulation of PP2A activity. In certain embodiments, the term "modulate" refers to ME activity by interfering with interaction of PP2A and ME.

Nutraceuticals: As used herein, "nutraceuticals" are products that supplement the diet to help promote the maintenance of good health.

Neurodegenerative Disease As used herein, "neurodegenerative disease" means any condition in which cells of the brain and/or spinal cord are lost or degraded. Neurodegenerative diseases include a subset of neurological disorders containing neuron pathologies and/or any disease caused by a malformed protein, e.g., proteinopathies.

PP2A: As used herein, "PP2A" means a PP2A C subunit alone, an AC dimer, or a PP2A holoenzyme. PP2A dimer formation typically includes the assembly of an A subunit and a C subunit. PP2A heterotrimeric holoenzyme formation typically includes the assembly of an A subunit, a C subunit, and a regulatory subunit, selected from any of the B, B', B" and/or B'" families. PP2A activity.

PP2A activity: As used herein, "PP2A activity" means any phosphatase activity resulting from the catalytic C-subunit ($PP2A_C$), the AC dimer ($PP2A_{AC}$), as well as the PP2A holoenzyme, assembled from A, C and any one of the regulatory subunits belonging to the B, B', B" and B'" families. In certain embodiments, to provide but a few examples, PP2A activity can be modulated by compounds and/or compositions that modulate the methylation of PP2A, modulate the demethylation of PP2A, modulate the interaction of PP2A substrates with PP2A, modulate the interaction of auxiliary proteins with PP2A and/or directly interact with PP2A, etc.

Pharmaceuticals: As used herein, "pharmaceuticals", like nutraceuticals, are drugs or medicines that are prepared and used for the treatment of diseases and/or disorders.

Pharmaceutically acceptable prodrugs: The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

Pharmaceutically acceptable salt: The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 66: 1-19, 1977; incorporated herein by reference. The salts can be prepared in situ during the final isolation and purification of the compounds of the invention, or separately by reacting the free base functionality with a suitable organic or inorganic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

Protecting group: One of ordinary skill in the art will appreciate that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS) 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), $N^2$-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N—[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein. However, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

Substituted: It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders.

Stable: The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

Synthetic tryptamide derivatives: As used herein, the terms "synthetic tryptamide derivatives" and "synthetic tryptamide analogs", used interchangeably, mean compounds of Formula I which are not naturally occurring, i.e. are not found in plants or plant extracts. Representative examples of naturally occurring compounds are found in copending applications 61/124,949, 61/125,169, and 61/125,205, and are depicted herein as Compounds I-63 through I-72, and Compounds I-81 through I-86.

Tautomers: As used herein, the term "tautomers" are particular isomers of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridone-hydroxypyridine forms.

Therapeutically effective amount: As used herein, the term "therapeutically effective amount" means an amount of a substance (e.g., a therapeutic agent, composition, and/or formulation) that elicits a desired biological response. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a composition and/or formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition.

Treat or treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

Unit dosage form: The expression "unit dosage form" as used herein refers to a physically discrete unit of a provided formulation appropriate for the subject to be treated. It will be understood, however, that the total daily usage of provided formulation will be decided by the attending physician within the scope of sound medical judgment. The specific effective dose level for any particular subject or organism will depend upon a variety of factors including the disorder being treated and the severity of the disorder; activity of specific active agent employed; specific formulation employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

DETAILED DESCRIPTION OF CERTAIN EMBODIMENTS

I. Description of Exemplary Compounds

As noted above, compounds useful in accordance with the present invention include those of formula I.

According to one aspect, the present invention provides compounds of formula I,

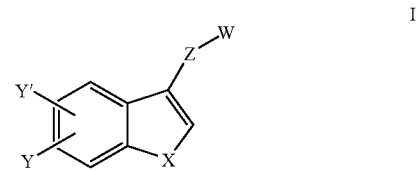

or a pharmaceutically acceptable salt thereof, wherein:
Z is selected from the group consisting of:

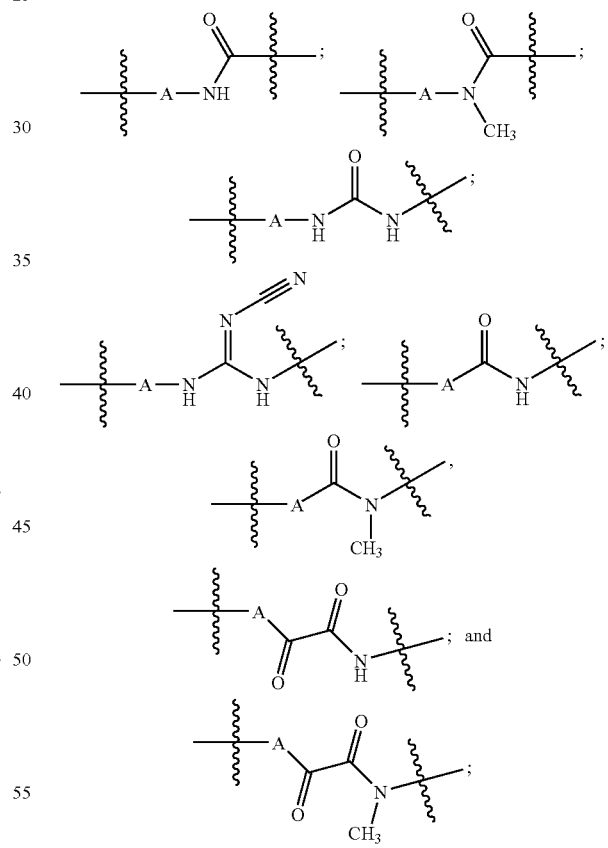

A is $-(CH_2)_n$, wherein n is 0, 1 or 2;
X is NH, NR', O, or S;
W is a linear or branched, saturated or unsaturated alkyl having between 10 and 25 carbons, optionally containing 1 or 2 heteroatoms selected from NH, NR' or O, and optionally substituted with one or more —OR groups or halogen;
Y is selected from H, —OH, —R, —OR, —NH$_2$, —NR'R', —NR'R', —C(O)NHR', —C(O)NR'R', halogen, or a saccharide;

Y' is selected from H, —OH, —R, —OR, —NH$_2$, —NHR', —NR'R', —C(O)NHR', —C(O)NR'R', halogen, or a saccharide;

R is H, an optionally substituted —C$_{1-6}$ alkyl which may be linear, cyclic, or branched, an optionally substituted —C$_6$ aromatic, an optionally substituted 5- or 6-membered heteroaromatic ring, —C(O)R', —C(O)H, —C(O)OR', —C(O)OH, —C(N)NH, or —C(N)NR'; and R' is an optionally substituted C$_1$-C$_6$ alkyl or alkenyl group which may be linear, cyclic, or branched;

or R and R' may be taken together to form a saturated 5-6 membered heterocyclic ring having 1-2 heteroatoms selected from oxygen or nitrogen.

According to one aspect, the present invention provides compounds of formula I,

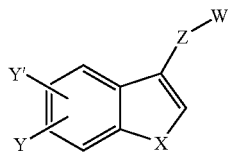

or a pharmaceutically acceptable salt thereof, wherein:
Z is selected from the group consisting of:

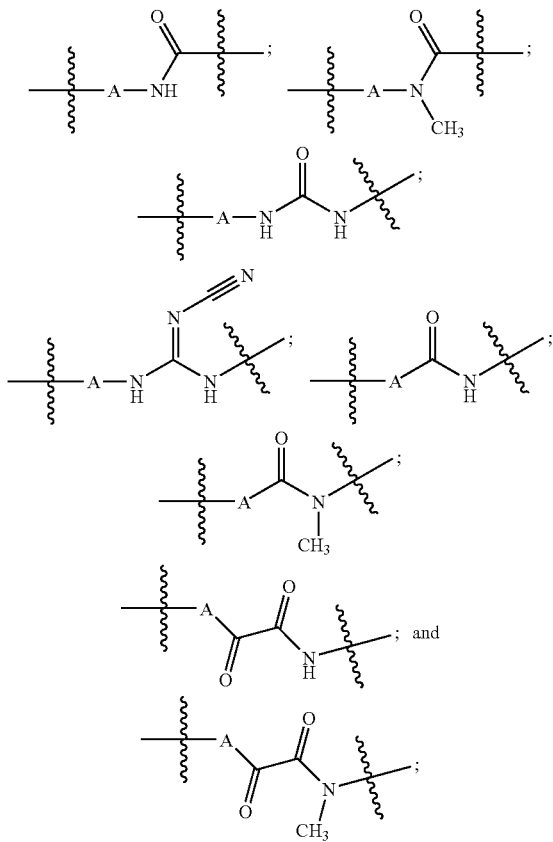

A is —(CH$_2$)$_n$, or —(CB$_2$)$_n$, wherein n is 0, 1 or 2;
B is H, —NHC(═O)OR', or —(═O)OR;
X is NH, NR', O, or S;
W is a linear or branched, saturated or unsaturated alkyl having between 10 and 25 carbons, optionally containing 1 or 2 heteroatoms selected from NH, NR' or O, and optionally substituted with one or more —OR groups or halogen;

Y and Y' are independently selected from H, —OH, —R, —OR, —NH$_2$, —NHR', —NR'R', —NHR", —C(O)NHR', —C(O)NR'R', halogen, or a saccharide;

—R is H, —C$_{1-6}$ alkyl which may be linear, cyclic, or branched, —C$_6$ aromatic, a 5- or 6-membered heteroaromatic ring, —C(O)R', —C(O)H, —C(O)OR', —C(O)OH, —C(N)NH, —C(N)NR'; and —R' is a C$_1$-C$_6$ alkyl or alkenyl group which may be linear, cyclic, or branched;

—R" is a C$_{1-2}$ alkyl optionally substituted with —OH;

(a) wherein the compound is not naturally occurring;
(b) when Z is

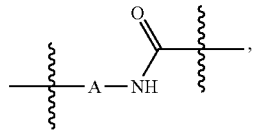

then n is not 0;
(c) which compound is characterized by an ability to modulate PP2A methylation, such that at least one of the following conditions is met:
  (i) when the compound is incubated with purified PP2A and purified MT, the compound modulates methylation of PP2A with an IC$_{50}$ below 100 μM;
  (ii) when the compound is incubated with purified PP2A and purified ME, the compound modulates demethylation of PP2A with an IC$_{50}$ below 100 μM;
  (iii) when the compound is separately incubated with
    purified PP2A and purified MT; and
    purified PP2A and purified ME;
    the compound shows selective activity towards MTase as compared with MEase.
  (iv) when the compound is separately incubated with
    purified PP2A and purified MT; and
    purified PP2A and purified ME;
    the compound shows selective activity towards MEase as compared with MTase; and/or
  (v) when the compound is incubated with purified PP2A, purified ME, and purified MT, methylation of PP2A is observed at a different level than is observed under comparable conditions without the compound;
and wherein one of the following conditions is met:
(d) wherein the compound is further characterized in that, when the compound is incubated with isolated PP2A and an isolated non-protein PP2A target in the absence of MT and ME, observed phosphorylation of the isolated non-protein target compares to that observed without the compound; and
(e) wherein the compound is further characterized in that, when the compound is incubated with isolated PP2A and an isolated protein PP2A target in the absence of MT and ME, observed phosphorylation of the isolated protein target compares to that observed without the compound;
or a pharmaceutically acceptable salt thereof.

In certain embodiments, the compound is not a compound selected from the group consisting of:
N-(1,4-dimethylpentyl)-5,6-dimethyl-3-benzofuranacetamide;
N-[2-(6-methoxy-1H-indol-3-yl)ethyl]-dodecanamide;
N-(1,4-dimethylpentyl)-1H-indole-3-propanamide;
N-(1,1-diethyl-2-propyn-1-yl)-1H-indole-3-propanamide;

N-(1-methylhexyl)-1H-Indole-3-propanamide;
N-(1,1-diethyl-2-propyn-1-yl)-1H-indole-3-acetamide;
N-(2-ethylhexyl)-1H-Indole-3-carboxamide;
N-(1,1-diethyl-2-propyn-1-yl)-6-ethyl-3-benzofuranacetamide;
N-[2-(5-chloro-1H-indol-3-yl)ethyl]-2-ethyl-hexanamide;
N-[2-(5-hydroxy-1H-indol-3-yl)ethyl]-5,8,11,14-eicosatetraenamide;
2-ethyl-N-[2-(5-methyl-1H-indol-3-yl)ethyl]-hexanamide;
1-methyl-N-(5-methylhexan-2-yl)-1H-indole-2-carboxamide;
N-(1,5-dimethylhexyl)-6-methoxy-3-benzofuranacetamide;
N-(1,5-dimethylhexyl)-1H-indole-3-propanamide;
2-ethyl-N-[2-(5-methoxy-1H-indol-3-yl)ethyl]-hexanamide;
N-(1,4-dimethylpentyl)-1H-Indole-3-acetamide;
N-[2-(6-methoxy-1H-indol-3-yl)ethyl]-2-propyl-pentanamide;
N-(1,5-dimethylhexyl)-1H-Indole-3-acetamide;
N-[2-(5-chloro-1H-indol-3-yl)ethyl]-2-propyl-pentanamide;
6-methoxy-N-[(1S)-1-methylhexyl]-3-benzofuranacetamide;
N-[2-(5-methyl-1H-indol-3-yl)ethyl]-2-propyl-pentanamide;
N-(1,1-diethyl-2-propyn-1-yl)-6-methoxy-3-benzofuranacetamide;
N-dodecyl-α-oxo-1H-indole-3-acetamide;
N-(1,4-dimethylpentyl)-6-methoxy-3-benzofuranacetamide;
5-bromo-N-octadecyl-α-oxo-1H-indole-3-acetamide;
N-[3-ethyl-2-(4-morpholinyl)pentyl]-N'-[2-(1H-indol-3-yl)ethyl]-urea;
N-4-hydroxy-N1-[2-(1H-indol-3-yl)ethyl]-2-(2-methylpropyl)-butanediamide;
3-[2-[[2-(1H-indol-3-ylethyl]amino]-2-oxoethyl]-methyl-ester 4-Hexenoic acid;
7-[[[6-(aminoiminomethyl)-1H-indol-3-yl]carbonyl]amino]-1,1-dimethylethyl ester heptanoic acid;
7-[[[6-(aminothioxomethyl)-1H-indol-3-yl]carbonyl]amino]-1,1-dimethylethyl ester heptanoic acid;
2-[[2-(1H-indol-3-yl)acetyl]amino]-(2S)-heptanoic acid;
N-[3-ethyl-2-(4-morpholinyl)pentyl]-1H-indole-3-propanamide;
N4-hydroxy-N1-[2-(1H-indol-3-yl)ethyl]-N1-methyl-2-(2-methylpropyl)-(2R)-butanediamide;
7-[[[5-(aminoiminomethyl)-1H-indol-3-yl]carbonyl]amino]-1,1-dimethylethyl ester heptanoic acid; and

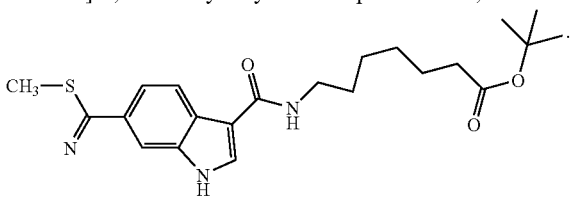

According to one aspect, the present invention provides compounds of formula I,

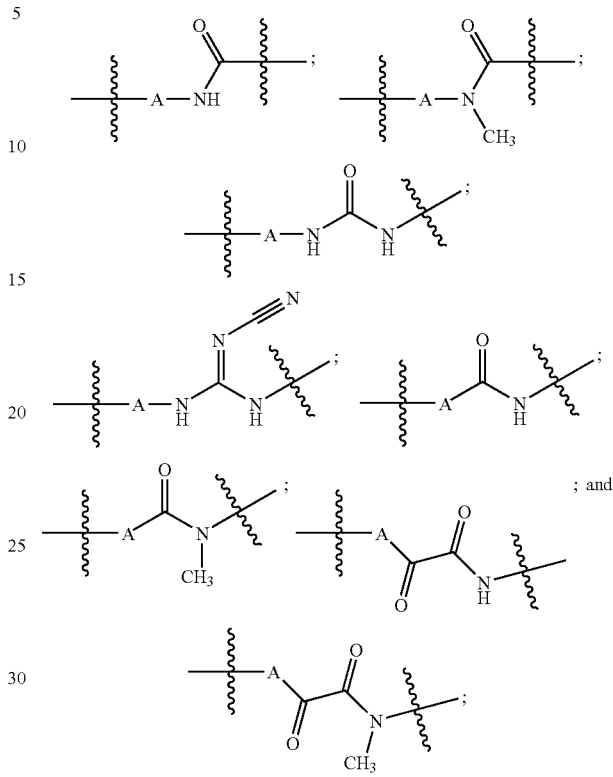

or a pharmaceutically acceptable salt thereof, wherein:

Z is selected from the group consisting of:

A is —$(CH_2)_n$, or —$(CB_2)_n$, wherein n is 0, 1 or 2;

B is H, —NHC(=O)OR, or —C(=O)OR;

X is NH, NR', O, or S;

W is a linear or branched, saturated or unsaturated alkyl having between 10 and 25 carbons, optionally containing 1 or 2 heteroatoms selected from NH, NR' or O, and optionally substituted with one or more —OR groups or halogen;

Y and Y' are independently selected from H, —OH, —R, —OR, —$NH_2$, —NHR', —NR'R', —NHR", —C(O)NHR', —C(O)NR'R', halogen, or a saccharide;

—R is H, —$C_{1-6}$ alkyl which may be linear, cyclic, or branched, —$C_6$ aromatic, a 5- or 6-membered heteroaromatic ring, —C(O)R', —C(O)H, —C(O)OR', —C(O)OH, —C(N)NH, —C(N)NR; and —R' is a $C_1$-$C_6$ alkyl or alkenyl group which may be linear, cyclic, or branched;

—R" is a —$C_{1-2}$ alkyl optionally substituted with —OH;

wherein the compound is not naturally occurring; and which compound is characterized by an activity selected from the group consisting of:

(a) wherein the compound is not naturally occurring;

(b) which compound is characterized by an ability to modulate PP2A methylation, such that at least one of the following conditions is met:

(i) when the compound is incubated with purified PP2A and purified MT, the compound modulates methylation of PP2A with an $IC_{50}$ below 100 μM;

(ii) when the compound is incubated with purified PP2A and purified ME, the compound modulates demethylation of PP2A with an IC$_{50}$ below 100 μM;
(iii) when the compound is separately incubated with
   purified PP2A and purified MT; and
   purified PP2A and purified ME;
   the compound shows selective activity towards MTase as compared with MEase.
(iv) when the compound is separately incubated with
   purified PP2A and purified MT; and
   purified PP2A and purified ME;
   the compound shows selective activity towards MEase as compared with MTase; and/or
(v) when the compound is incubated with purified PP2A, purified ME, and purified MT, methylation of PP2A is observed at a different level than is observed under comparable conditions without the compound;
and wherein one of the following conditions is met:
(c) wherein the compound is further characterized in that, when the compound is incubated with isolated PP2A and an isolated non-protein PP2A target in the absence of MT and ME, observed phosphorylation of the isolated non-protein target compares to that observed without the compound; and
(d) wherein the compound is further characterized in that, when the compound is incubated with isolated PP2A and an isolated protein PP2A target in the absence of MT and ME, observed phosphorylation of the isolated protein target compares to that observed without the compound; or a pharmaceutically acceptable salt thereof.

According to one aspect, the present invention provides isolated compounds of formula I,

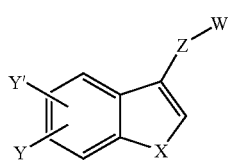

I or a pharmaceutically acceptable salt thereof, wherein:
Z is selected from the group consisting of:

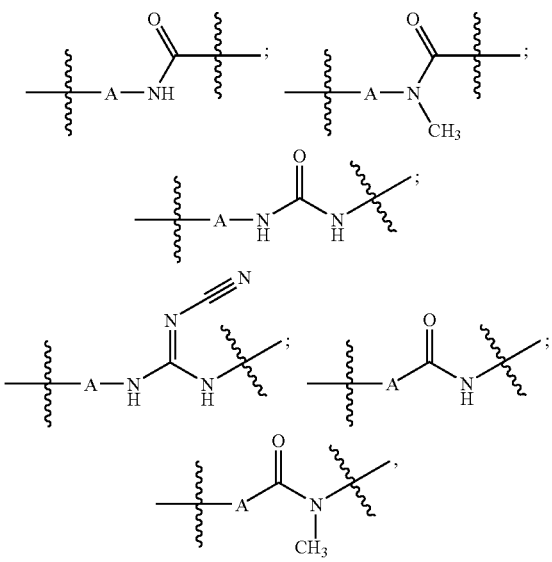

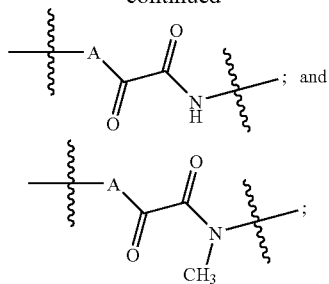

A is —(CH$_2$)$_n$—, wherein n is 0, 1 or 2;
X is NH, NR', O, or S;
W is a linear or branched, saturated or unsaturated alkyl having between 10 and 25 carbons, optionally containing 1 or 2 heteroatoms selected from NH, NR' or O, and optionally substituted with one or more —OR groups or halogen;
Y and Y' are independently selected from H, —OH, —R, —OR, —NH$_2$, —NHR', —NR'R', —C(O)NHR', —C(O)NR'R', halogen, or a saccharide;
R is H, —C$_{1-6}$ alkyl which may be linear, cyclic, or branched, —C$_6$ aromatic, a 5- or 6-membered heteroaromatic ring, —C(O)R', —C(O)H, —C(O)OR', —C(O)OH, —C(N)NH, —C(N)NR'; and
R' is a C$_1$-C$_6$ alkyl or alkenyl group which may be linear, cyclic, or branched; and
(a) when Z is

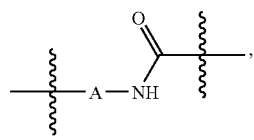

then n is not 0;
(b) which compound is characterized by an ability to modulate PP2A methylation, such that at least one of the following conditions is met:
(i) when the compound is incubated with purified PP2A and purified MT, the compound modulates methylation of PP2A with an IC$_{50}$ below 100 μM;
(ii) when the compound is incubated with purified PP2A and purified ME, the compound modulates demethylation of PP2A with an IC$_{50}$ below 100 μM;
(iii) when the compound is separately incubated with
   purified PP2A and purified MT; and
   purified PP2A and purified ME;
   the compound shows selective activity towards MTase as compared with MEase.
(iv) when the compound is separately incubated with
   purified PP2A and purified MT; and
   purified PP2A and purified ME;
   the compound shows selective activity towards MEase as compared with MTase; and/or
(v) when the compound is incubated with purified PP2A, purified ME, and purified MT, methylation of PP2A is observed at a different level than is observed under comparable conditions without the compound;

and wherein one of the following conditions is met:
(c) wherein the compound is further characterized in that, when the compound is incubated with isolated PP2A and an isolated non-protein PP2A target in the absence of MT and ME, observed phosphorylation of the isolated non-protein target compares to that observed without the compound; and
(d) wherein the compound is further characterized in that, when the compound is incubated with isolated PP2A and an isolated protein PP2A target in the absence of MT and ME, observed phosphorylation of the isolated protein target compares to that observed without the compound;
or a pharmaceutically acceptable salt thereof.

In certain embodiments, the present invention provides a compound of formula II,

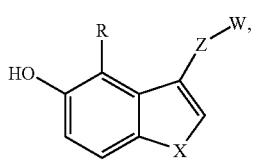

II or a pharmaceutically acceptable salt thereof, wherein each of Z, X, W and R as defined above for formula I and described in embodiments herein. An exemplary compound of formula II is compound I-43, and other applicable exemplary compounds depicted in Table 1.

In certain embodiments, the present invention provides a compound of formula III,

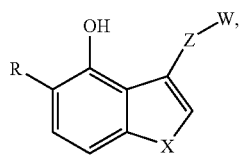

III or a pharmaceutically acceptable salt thereof, wherein each of Z, X, W and R as defined above for formula I and described in embodiments herein. An exemplary compound of formula III is compound I-44, and other applicable exemplary compounds depicted in Table 1. In certain embodiments, the present invention provides a compound of formula IV,

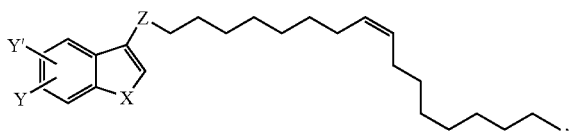

IV or a pharmaceutically acceptable salt thereof, wherein each of Z, X, Y and Y' as defined above for formula I and described in embodiments herein. An exemplary compound of formula IV is compound I-40, and other applicable exemplary compounds depicted in Table 1.

In certain embodiments, the present invention provides a compound of formula V,

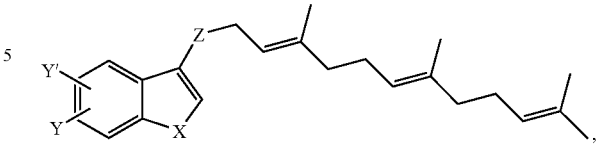

V or a pharmaceutically acceptable salt thereof, wherein each of Z, X, Y and Y' as defined above for formula I and described in embodiments herein. An exemplary compound of formula V is compound I-41, and other applicable exemplary compounds depicted in Table 1.

In certain embodiments, the present invention provides a compound of formula VI,

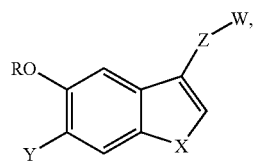

VI or a pharmaceutically acceptable salt thereof, wherein each of Z, X, W and R and Y are as defined above for formula I and described in embodiments herein. Exemplary compounds of formula VI include compound I-45 and compound I-46, and other applicable exemplary compounds depicted in Table 1.

In certain embodiments, the present invention provides a compound of formula VII,

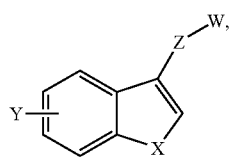

VII or a pharmaceutically acceptable salt thereof, wherein each of Z, X, W and Y are as defined above for formula I and described in embodiments herein. Exemplary compounds of formula VII include compound I-47 and compound I-48, and other applicable exemplary compounds depicted in Table 1.

In certain embodiments, the present invention provides a compound of formula VIII,

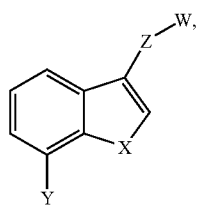

VIII or a pharmaceutically acceptable salt thereof, wherein each of Z, X, W and Y are as defined above for formula I and described in embodiments herein. Exemplary compounds of formula VIII include compounds I-21, I-22, I-26, I-40, and I-52, and other applicable exemplary compounds depicted in Table 1.

In certain embodiments, the present invention provides a compound of formula IX,

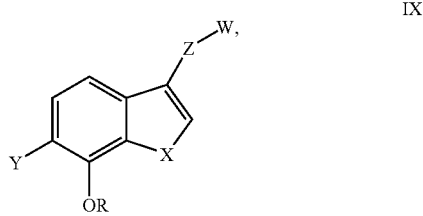

or a pharmaceutically acceptable salt thereof, wherein each of Z, X, W and Y are as defined above for formula I and described in embodiments herein. An exemplary compound of formula IX is compound I-27, and other applicable exemplary compounds depicted in Table 1.

According to one aspect, the present invention provides fatty-acid conjugated compounds of formula Ia:

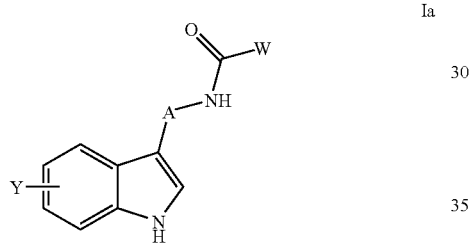

wherein,

A is —(CH$_2$)$_n$, wherein n is 0, 1 or 2;

W is a linear or branched, saturated or unsaturated alkyl having between 10 and 25 carbons, optionally containing 1 or 2 heteroatoms selected from NH, NR' or O, and optionally substituted with one or more —OR groups or halogen;

Y is independently selected from H, —OH, or a saccharide, and having an activity in the inhibition of methylesterase on PP2A (IC$_{50}$) of less than about 50 μM characterized by a free-fatty acid content lower than about 20%.

In certain embodiments, W is a linear or branched, saturated or unsaturated alkyl having between 15 and 21 carbons, optionally containing 1 or 2 heteroatoms selected from NH, NR' or O, and optionally substituted with one or more —OR groups or halogen.

In certain embodiments, W is a linear, saturated alkyl having between 15 and 21 carbons.

As generally defined above, X is NH, NR', O, or S. In certain embodiments, X is NH. In certain embodiments, X is O. In certain embodiments, X is S. In certain embodiments, X is NR'. In certain embodiments, R' is an optionally substituted C$_1$-C$_6$ alkyl. In certain embodiments, X is —NHCH$_3$ when R' is —CH$_3$. In certain embodiments X is —NHCH$_2$CH$_3$, when R' is —CH$_2$CH$_3$. In certain embodiments X is —NHCH(CH$_3$)$_2$, when R' is —CH$_2$CH$_3$.

In certain embodiments, the present invention provides naturally occurring fatty-acid conjugated compounds, which may be added to or combined with pharmaceuticals, nutraceuticals, or other comestibles for example to treat, prevent, control or ameliorate diabetes, insulin resistance, and metabolic syndrome.

In some embodiments, the present invention provides naturally occurring and/or synthetic fatty-acid conjugated compounds which may themselves be added to or combined with pharmaceuticals, nutraceuticals, or other comestibles to treat, prevent, control or ameliorate neurodegenerative diseases such as proteinopathies. Exemplary proteinopathies include tauopathies and synucleopathies. In certain embodiments, tauopathies include Alzheimer's Disease, neurodegeneration in adult cases of Down's syndrome, Dementia pugilistica, Pick's Disease, Guam parkinsonism dementia complex, Fronto-temporal dementia, Cortico-basal degeneration, Pallido-pontal-nigral degeneration, and Progressive supranuclear palsy. In certain embodiments, synucleinopathies (e.g., alpha-synucleinopathies), include Parkinson's Disease, Dementia with Lewy bodies (DLB), and multiple system atrophy (MSA).

In certain embodiments, compounds which may themselves be added to or combined with pharmaceuticals, nutraceuticals, or other comestibles to treat, prevent, control or ameliorate neurological disorders, diabetes and/or metabolic syndrome as further described herein.

In certain embodiments, the present invention provides fatty-acid conjugated compounds of Formula Ib,

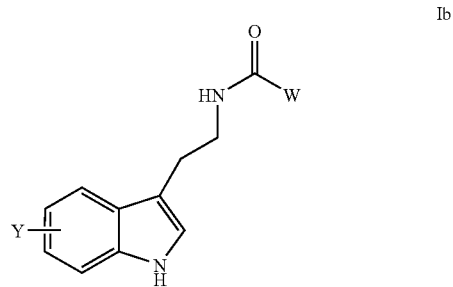

or a pharmaceutically acceptable salt thereof, wherein:

W is a linear or branched, saturated or unsaturated alkyl having between 15 and 21 carbons; and Y is independently hydrogen, a hydroxyl or a saccharide; and wherein the compound has an activity in the inhibition of methylesterase on PP2A (IC$_{50}$) of less than about 50 μM (micromolar), and is characterized by a free-fatty acid content of less than about 20% by weight of the compound. In some embodiments, W ranges from 16 to 20 carbons. In other embodiments, W ranges from 18 to 20 carbons. Exemplary compounds of formula I-b include compounds I-63 through I-72 and I-81 through I-86. All compounds I-63 through I-72 and I-81 through I-86 are naturally occurring compounds and are notated with an asterisk ("*") in Table 1 below.

In certain embodiments of the present invention, the compound is characterized as having a free fatty-acid content of less than about 20% by weight of the compound. In yet other embodiments, the compound contains less than about 20% by weight of compounds of Formula Ib where W has less than 14 carbons or more than 20 carbons.

The indole portion of the compounds of Formula Ia may be substituted with one or more hydroxyl groups as in formula Ic:

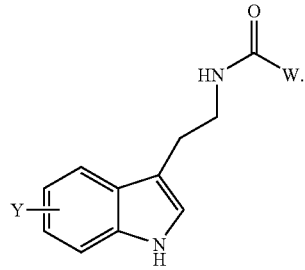
Ic

In some embodiments, the indole portion is substituted with one hydroxyl group at any indole ring position. In other embodiments, the indole portion is substituted with two hydroxyl groups at any ring position. In yet other embodiments, the indole portion is substituted at the 4 and/or 5 positions with one or more hydroxyl groups, as in formulae Id and Ie:

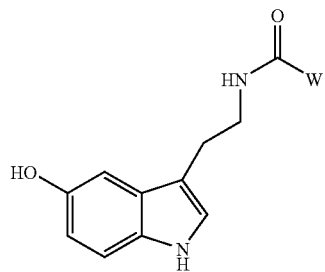
Id

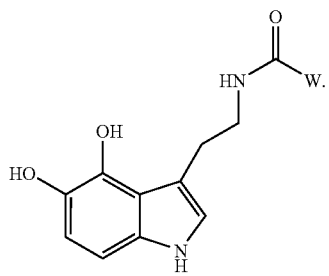
Ie

In other embodiments, the indole portion is substituted with one or more saccharides as in formula If:

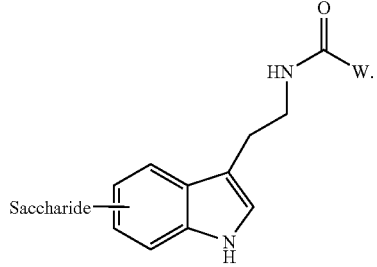
If

The saccharide may be a monosaccharide, a disaccharide, or a trisaccharide. In some embodiments, the saccharide is substituted at the 5-position, as in formula Ig:

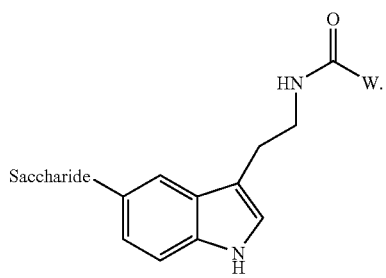
Ig

Exemplary compounds of formula I-g include compounds and I-81 through I-86, and other applicable exemplary compounds depicted in Table 1.

In certain embodiments, the present invention provides fatty-acid conjugated compounds of formula Ih,

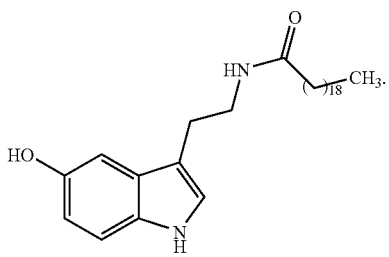
Ih

The aliphatic portion ("fatty acid") of the compounds of Formula Ia, represented by the —C(O)—(CH$_2$)$_n$—CH$_3$ group, may be branched or normal and may be substituted with one or more hydroxyl groups. In some embodiments, the aliphatic portion is substituted with one hydroxyl group.

In some embodiments, the aliphatic portion contains one or more double bonds. In other embodiments, the aliphatic portion contains one double bond.

As generally defined above, the Z group of the above described formulae is selected from the group consisting of:

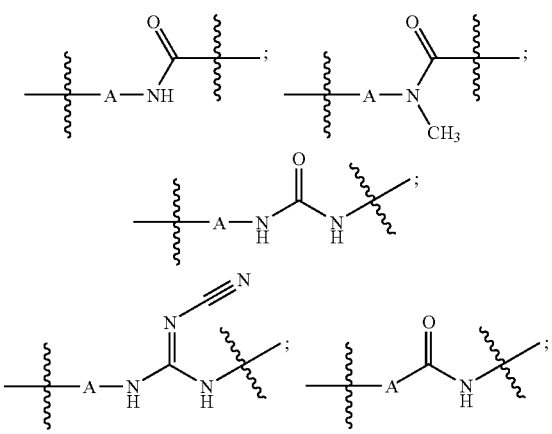

-continued

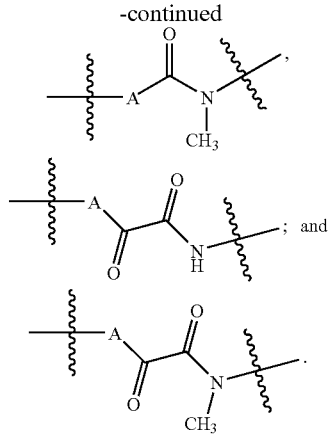

In certain embodiments, the Z group is

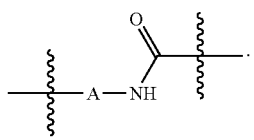

In certain embodiments the Z group is

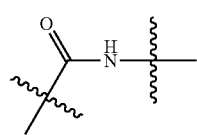 [SMILES: *NC(*)=O]

when A is a bond. In certain embodiments the Z group is

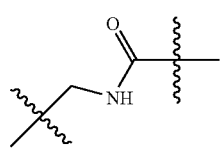 [SMILES: *CNC(*)=O]

when A is —CH$_2$—. In certain embodiments the Z group is

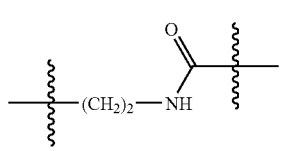

when A is —(CH$_2$)$_2$—. In certain embodiments, the Z group is

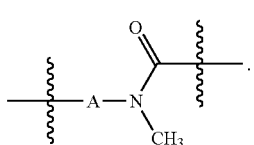

In certain embodiments the Z group is

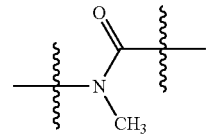 [SMILES: *C(=O)N(*)C]

when A is a bond. In certain embodiments the Z group is

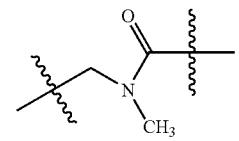 [SMILES: *CN(C)C(*)=O]

when A is —CH$_2$—. In certain embodiments the Z group is

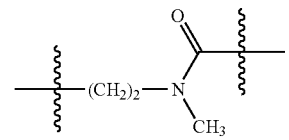

when A is —(CH$_2$)$_2$—. In certain embodiments, the Z group is

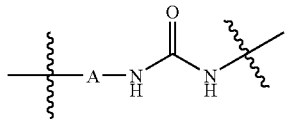

In certain embodiments the Z group is

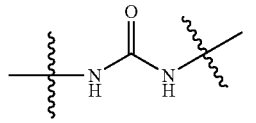 [SMILES: *NC(=O)N*]

when A is a bond. In certain embodiments the Z group is

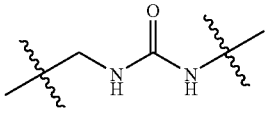 [SMILES: *CNC(=O)N*]

when A is —CH$_2$—. In certain embodiments the Z group is

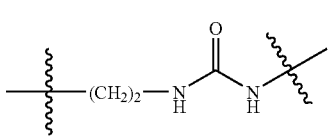

when A is —(CH$_2$)$_2$—. In certain embodiments, the Z group is

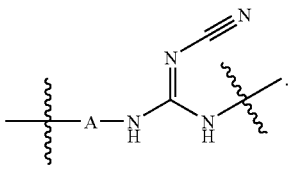

In certain embodiments the Z group is

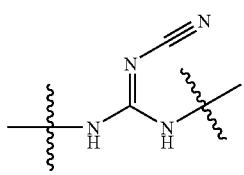 [SMILES: *NC(=NC#N)N*]

when A is a bond. In certain embodiments the Z group is

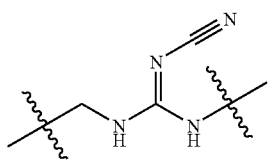 [SMILES: *CN/C(=N/C#N)N*]

when A is —CH$_2$—. In certain embodiments the Z group is

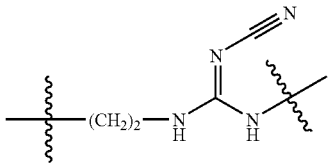

when A is —(CH$_2$)$_2$—. In certain embodiments, the Z group is

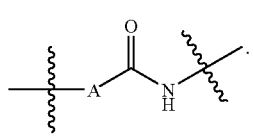

In certain embodiments the Z group is

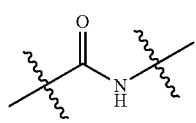 [SMILES: *NC(*)=O]

when A is a bond. In certain embodiments the Z group is

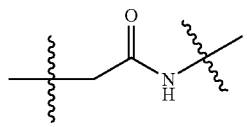 [SMILES: *CC(=O)N*]

when A is —CH$_2$—. In certain embodiments the Z group is

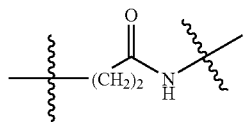

when A is —(CH$_2$)$_2$—. In certain embodiments, the Z group is

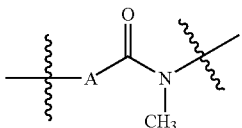

In certain embodiments the Z group is

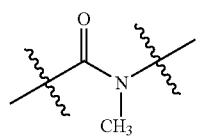

when A is a bond. In certain embodiments the Z group is

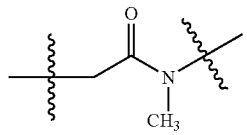 [SMILES: *CC(=O)N(*)C]

when A is —CH$_2$—. In certain embodiments the Z group is

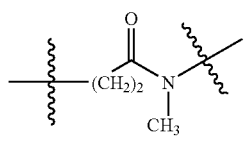

when A is —(CH$_2$)$_2$—. In certain embodiments, the Z group is

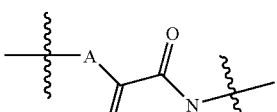

In certain embodiments the Z group is

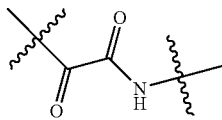

when A is a bond. In certain embodiments the Z group is

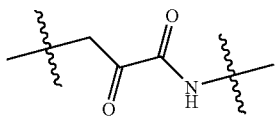 [SMILES: *CC(=O)C(=O)N*]

when A is —CH$_2$—. In certain embodiments the Z group is

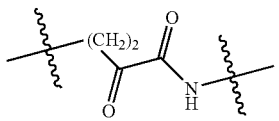

when A is —(CH$_2$)$_2$—. In certain embodiments, the Z group is

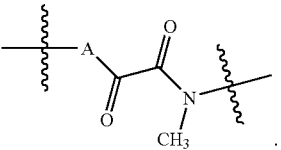

In certain embodiments the Z group is

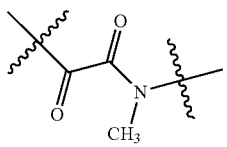 [SMILES: *C(=O)C(=O)N(*)C]

when A is a bond. In certain embodiments the Z group is

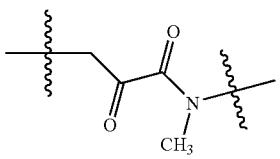 [SMILES: *CC(=O)C(=O)N(*)C]

when A is —CH$_2$—. In certain embodiments the Z group is

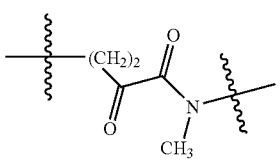

when A is —(CH$_2$)$_2$—.

As generally defined above, the A group is —(CH$_2$)$_n$—. In certain embodiments A is a bond when n is 0. In certain embodiments, A is —CH$_2$— when n is 1. In certain embodiments, A is —(CH$_2$)$_2$— when n is 2.

As generally defined above, n is 0, 1 or 2. In certain embodiments, n is 0. In certain embodiments, n is 1.

As generally defined above, the W group of formulae I, II, III, VI, and VII, is a linear or branched, saturated or unsaturated alkyl having between 10 and 25 carbons, optionally containing 1 or 2 heteroatoms selected from NH, NR' or O, and optionally substituted with one or more —OR groups or halogen. In some embodiments, W ranges from 16 to 20 carbons. In other embodiments, W ranges from 18 to 20 carbons.

In some embodiments, the aliphatic portion, W, may be substituted with one or more hydroxyl groups. In other embodiments, the aliphatic portion is substituted with one hydroxyl group. Compounds of formula I having a hydroxyl group substituted at the 4- or 5-position and an additional R group at the other of the 5- or 4-position, are represented by formulas II and III, respectively.

In certain embodiments, W is a linear, saturated alkyl. In certain embodiments, W is a linear, saturated alkyl having 10 carbons. In certain embodiments, W is —(CH$_2$)$_9$CH$_3$. In certain embodiments, W is linear. In certain embodiments, W is a linear, saturated alkyl having 11 carbons. In certain embodiments, W is —(CH$_2$)$_{10}$CH$_3$. In certain embodiments, W is a linear, saturated alkyl having 12 carbons. In certain embodiments, W is —(CH$_2$)$_{11}$CH$_3$. In certain embodiments, W is a linear, saturated alkyl having 13 carbons. In certain embodiments, W is —(CH$_2$)$_{12}$CH$_3$. In certain embodiments, W is a linear, saturated alkyl having 14 carbons. In certain embodiments, W is —(CH$_2$)$_{13}$CH$_3$. In certain embodiments, W is a linear, saturated alkyl having 15 carbons. In certain embodiments, W is —(CH$_2$)$_{14}$CH$_3$. In certain embodiments, W is —(CH$_2$)$_{14}$CH$_3$ optionally substituted with one or more —OR groups or halogen. In certain embodiments, W is substituted with an —OR group. In certain embodiments, R is —H. In certain embodiments W is —(CH$_2$)$_{12}$CH$_2$(OH)CH$_2$CH$_3$. In certain embodiments W is —(CH$_2$)$_{13}$CH$_2$(OH)CH$_3$. In certain embodiments, W is a linear, saturated alkyl having 16 carbons. In certain embodiments, W is —(CH$_2$)$_{15}$CH$_3$. In certain embodiments, W is a linear, saturated alkyl having 17 carbons. In certain embodiments, W is —(CH$_2$)$_{16}$CH$_3$. In certain embodiments, W is —(CH$_2$)$_{16}$CH$_3$ optionally substituted with one or more —OR groups or halogen. In certain embodiments, W is substituted with an —OR group. In certain embodiments, R is —H. In certain embodiments W is —(CH$_2$)$_{10}$CH$_2$(OH)—(CH$_2$)$_5$CH$_3$. In certain embodiments W is —(CH$_2$)$_{14}$CH$_2$(OH)CH$_2$CH$_3$. In certain embodiments W is —(CH$_2$)$_{15}$CH$_2$(OH)CH$_3$. In certain embodiments, W is a linear, saturated alkyl having 18 carbons. In certain embodiments, W is —(CH$_2$)$_{17}$CH$_3$. In certain embodiments, W is a linear, saturated alkyl having 19 carbons. In certain embodiments, W is —(CH$_2$)$_{18}$CH$_3$. In certain embodiments, W is —(CH$_2$)$_{18}$CH$_3$ optionally substituted with one or more —OR groups or halogen. In certain embodiments, the R group is H. In certain embodiments W is —(CH$_2$)$_{19}$OH. In certain embodiments, W is a linear, saturated alkyl having 20 carbons. In certain embodiments, W is —(CH$_2$)$_{19}$CH$_3$. In certain embodiments, W is a linear, saturated alkyl having 21 carbons. In certain embodiments, W is —(CH$_2$)$_{20}$CH$_3$. In certain embodiments, W is —(CH$_2$)$_{20}$CH$_3$ optionally substituted with one or more —OR groups or halogen. In certain embodiments, W is substituted with an —OR group. In certain embodiments, R is —H. In certain embodiments W is —(CH$_2$)$_{21}$OH. In certain embodiments, W is a linear, saturated alkyl having 22 carbons. In certain embodiments, W is —(CH$_2$)$_{21}$CH$_3$. In certain embodiments, W is a linear, saturated alkyl having 23 carbons. In certain embodiments, W is —(CH$_2$)$_{22}$CH$_3$. In certain embodiments, W is a linear, saturated alkyl having 24 carbons. In certain embodiments, W is —(CH$_2$)$_{23}$CH$_3$. In certain embodiments, W is a linear, saturated alkyl having 25 carbons. In certain embodiments, W is —(CH$_2$)$_{24}$—CH$_3$.

In certain embodiments, W is branched, saturated alkyl. In certain embodiments, W is branched, saturated alkyl having 15 carbons. In certain embodiments, W is —(CH$_2$)$_{14}$CH$_3$. In certain embodiments, W is —(CH$_2$)$_2$CH(CH$_3$)—(CH$_2$)$_3$CH(CH$_3$)—(CH$_2$)$_3$CH(CH$_3$)$_2$.

In certain embodiments, W is a linear, saturated alkyl containing 1 or 2 heteroatoms selected from NH, NR' or O, optionally substituted with one or more —OR groups or halogen. In certain embodiments, W is a linear, saturated alkyl containing an O heteroatom. In certain embodiments, W is —(CH$_2$)$_7$O(CH$_2$)$_{10}$CH$_3$. In certain embodiments, W is a linear, saturated alkyl containing an N heteroatom. In certain embodiments, W is —(CH$_2$)$_8$NH(CH$_2$)$_8$CH$_3$. In certain embodiments, W is a linear, saturated alkyl containing an NR' heteroatom. In certain embodiments, R' is methyl. In certain embodiments, W is —(CH$_2$)$_8$—N(CH$_3$)—(CH$_2$)$_8$CH$_3$. In certain embodiments, W is —(CH$_2$)$_7$—N(CH$_3$)—(CH$_2$)$_{10}$CH$_3$. In certain embodiments, W is —(CH$_2$)$_7$—N(CH$_3$)—(CH$_2$)$_{12}$CH$_3$. In certain embodiments, W is —(CH$_2$)$_7$—N(CH$_3$)—(CH$_2$)$_{12}$CH$_3$. An exemplary compound of formula I wherein W contains one or more heteroatoms is compound I-47.

In some embodiments, the aliphatic portion, W, contains one or more double bonds. In other embodiments, the aliphatic portion contains one double bond. Compounds of Formula I having one or more double bonds are represented by formulae IV and V.

In certain embodiments, W is a linear alkenyl. In certain embodiments, W is a linear, alkenyl having 17 carbons. In certain embodiments, W is —(CH$_2$)$_7$CH=CH(CH$_2$)$_7$CH$_3$.

In certain embodiments, W is branched alkenyl. In certain embodiments, W is a branched alkenyl having 15 carbons. In certain embodiments, W is —CH$_2$CH=C(CH$_3$)(CH$_2$)$_2$CH=C(CH$_3$)(CH$_2$)$_2$CH=C(CH$_3$)$_2$. In certain embodiments, W is a branched, alkenyl having 20 carbons. In certain embodiments, W is —CH$_2$CH=C(CH$_3$)(CH$_2$)$_3$CH(CH$_3$)(CH$_2$)$_3$CH(CH$_3$)(CH$_2$)$_3$CH(CH$_3$)$_2$.

In certain embodiments, W is a linear alkenyl, substituted with one or more —OR groups or halogen. In certain embodiments, W is a linear alkenyl, substituted with one or more —OR groups, wherein the R group is H to form an —OH group. In certain embodiments, W is a linear alkenyl having 15 carbons substituted with an —OH group. In certain embodiments, W is —(CH$_2$)$_7$CH=CH(CH$_2$)$_4$CH(OH)CH$_3$. In certain embodiments, W is —(CH$_2$)$_7$CH=CH(CH$_2$)$_3$CH(OH)CH$_2$CH$_3$. In certain embodiments, W is a linear alkenyl having 17 carbons substituted with an —OH group. In certain embodiments, W is —(CH$_2$)$_7$CH=CHCH$_2$CH(OH)(CH$_5$)CH$_3$.

As generally defined above, the Y' group of formulae I, IV, V, VI, and VII is selected from H, —OH, —R, —OR, —NH$_2$, —NHR', —NR'R', —C(O)NHR', —C(O)NR'R', halogen, or a saccharide.

In certain embodiments, Y' is H. In certain embodiments, Y' is —OH.

In certain embodiments, Y' is R, wherein R is an optionally substituted —C$_{1-6}$ alkyl which may be linear, cyclic, or branched. In certain embodiments, Y' is a —CH$_3$.

In certain embodiments, Y' is —OR, wherein R is —C$_{1-6}$ alkyl. In certain embodiments, Y' is OCH$_3$ when R is CH$_3$. In certain embodiments, Y' is —OCH$_2$CH$_3$ when R is —CH$_2$CH$_3$. In certain embodiments, Y' is —OR, wherein R is a branched —C$_{1-6}$ alkyl. In certain embodiments, Y' is —OR, wherein R is a branched —C$_3$ alkyl. In certain embodiments, Y' is —OCH(CH$_3$)$_2$. In certain embodiments, Y' is —OR, wherein R is —C(O)R' and wherein R' is C$_1$ alkyl. In certain embodiments, Y' is —OC(O)CH$_3$. In certain embodiments, Y' is —OR, wherein R is —C(O)R'. In certain embodiments R' is an optionally substituted C$_1$-C$_6$ alkyl group. Exemplary substituents include a —C(O)OH group. In certain embodiments, Y' is —OC(O)—(CH$_2$)$_2$C(O)OH. In certain embodiments, Y' is —OR, wherein R is an imidazolyl. In certain embodiments, the imidazolyl is 2-imidazolyl. In certain embodiments, the imidazolyl is 4-imidazolyl.

In certain embodiments, Y' is —NHR', wherein R' is a cyclic C$_1$-C$_6$ alkyl group. In certain embodiments R' is a cyclopentyl group. In certain embodiments, R' is an optionally substituted —C$_{1-6}$ alkyl. In certain embodiments, R' is an optionally substituted —C$_2$ alkyl group. In certain embodiments, Y' is —NH(CH$_2$)$_2$OH.

In certain embodiments, Y' is —NR'R', wherein or R and R' may be taken together to form a saturated 5-6 membered heterocyclic ring having 1-2 heteroatoms selected from oxygen or nitrogen. In certain embodiments, Y' is a morpholino group.

In certain embodiments, Y' is a halogen. In certain embodiments, Y' is Cl. In certain embodiments, Y' is F. In certain embodiments, Y' is Br.

As generally defined above, the Y group of formulae I, IV, V, VI, and VII is selected from H, —OH, —R, —OR, —NH$_2$, —NHR', —NR'R', —C(O)NHR', —C(O)NR'R', halogen, or a saccharide.

In certain embodiments, Y is H. In certain embodiments, Y is —OH.

In certain embodiments, Y is R, wherein R is an optionally substituted —C$_{1-6}$ alkyl which may be linear, cyclic, or branched. In certain embodiments, Y is a —CH$_3$.

In certain embodiments, Y is —OR, as in the compounds of formula VI. Exemplary compounds of formula VI include compound In some embodiments, the aliphatic portion contains one or more double bonds. In other embodiments, the aliphatic portion contains one double bond. Compounds of Formula (I) having one or more double bonds are represented in Formulas (IV) and (V) below. In certain embodiments, Y is —O, wherein R is —C$_{1-6}$ alkyl. In certain embodiments, Y is —OCH$_3$ when R is —CH$_3$. In certain embodiments, Y is —OCH$_2$CH$_3$ when R is —CH$_2$CH$_3$. In certain embodiments, Y is —OR', wherein R is a branched —C$_{1-6}$ alkyl. In certain embodiments, Y is —OR, wherein R is a branched —C$_3$ alkyl. In certain embodiments, Y is —OCH(CH$_3$)$_2$. In certain embodiments, Y is —OR, wherein R is —C(O)R' and wherein R' is C$_1$ alkyl. In certain embodiments, Y is —OC(O)CH$_3$. In certain embodiments, Y is —OR, wherein R is —C(O)R'. In certain embodiments R' is an optionally substituted C$_1$-C$_6$ alkyl group. Exemplary substituents include a —C(O)OH group. In certain embodiments, Y is —OC(O)—(CH$_2$)$_2$C(O)OH. In certain embodiments, Y is —OR, wherein R is an imidazolyl.

In certain embodiments, Y is —NHR', wherein R' is a cyclic C$_1$-C$_6$ alkyl group. In certain embodiments R' is a cyclopentyl group. In certain embodiments, R' is an optionally substituted —C$_{1-6}$ alkyl. In certain embodiments, R' is an optionally substituted —C$_2$ alkyl group. In certain embodiments, Y is —NH(CH$_2$)$_2$OH.

In certain embodiments, Y is —NR'R', wherein or R and R' may be taken together to form a saturated 5-6 membered heterocyclic ring having 1-2 heteroatoms selected from oxygen or nitrogen. In certain embodiments, Y is a morpholino group.

In certain embodiments, Y is a halogen. In certain embodiments, Y is Cl. In certain embodiments, Y is F. In certain embodiments, Y is Br.

In certain embodiments, Y is a saccharide. In certain embodiments, Y is a monosaccharide. In certain embodiments, Y is a disaccharide. In certain embodiments, Y is a trisaccharide. In certain embodiments, Y is

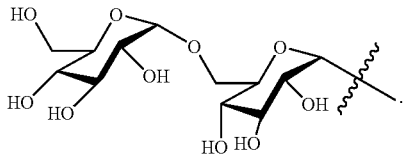

In certain embodiments, Y is

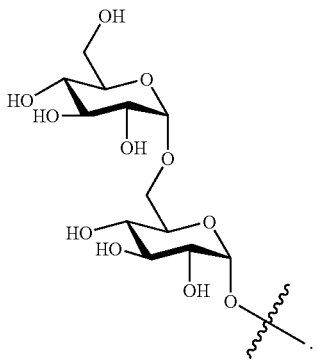

As generally defined above, R is H, optionally substituted —$C_{1-6}$ alkyl which may be linear, cyclic, or branched, an optionally substituted —$C_6$ aromatic, an optionally substituted 5- or 6-membered heteroaromatic ring, —C(O)R', —C(O)H, —C(O)OR', —C(O)OH, —C(N)NH, or —C(N)NR'.

In certain embodiments, R is an optionally substituted 5- or 6-membered heteroaromatic ring. In certain embodiments, R may be selected from pyran, pyridine, diazoles (e.g., imidazole, thiazole, pyrimidine, furan, thiophene, pyrazine, pyridazine, thiazine, oxazole, triazole and tetrazole. In certain embodiments, R is pyran. In certain embodiments, R is pyridine. In certain embodiments, R is a diazole. In certain embodiments, R is imidazole. In certain embodiments, R is thiazole. In certain embodiments, R is pyrimidine. In certain embodiments, R is furan. In certain embodiments, R is thiophene. In certain embodiments, R is pyrazine. In certain embodiments, R is pyridazine. In certain embodiments, R is thiazine. In certain embodiments, R is oxazole. In certain embodiments, R is triazole. In certain embodiments, R is tetrazole.

As generally defined above, R' is an optionally substituted $C_1$-$C_6$ alkyl or alkenyl group which may be linear, cyclic, or branched.

Exemplary compounds of the present invention are set forth in Table 1 below.

TABLE 1

Exemplary Compounds

| Compound Number | Compound Structure | Compound Name |
|---|---|---|
| I-1 | 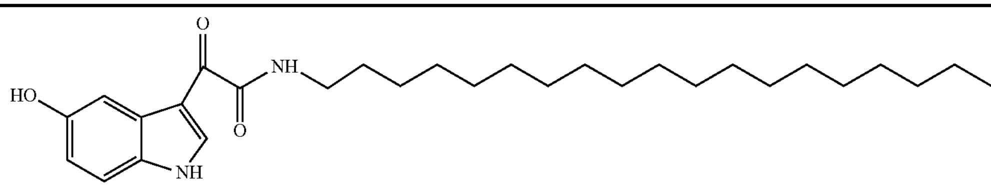 | 4-(5-hydroxy-1H-indol-3-yl)-N-nonadecyl-2-oxobutanamide |
| I-2 | 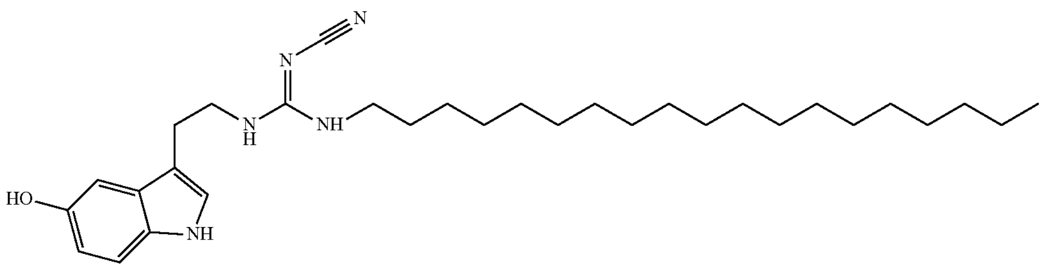 [SMILES: CCCCCCCCCCCCCCCCCCCN/C(=N\C#N)NCCc1c[nH]c2ccc(O)cc12] | 2-Cyano-3-[2-(5-hydroxy-1H-indol-3-yl)ethyl]-1-nonadecylguanidine |
| I-3 | 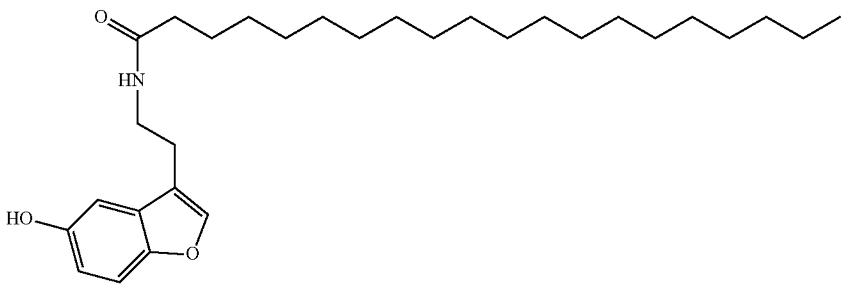 [SMILES: CCCCCCCCCCCCCCCCCCCC(=O)NCCc1coc2ccc(O)cc12] | N-[2-(5-hydroxy-1-benzofuran-3-yl)ethyl]icosanamide |
| I-4 | 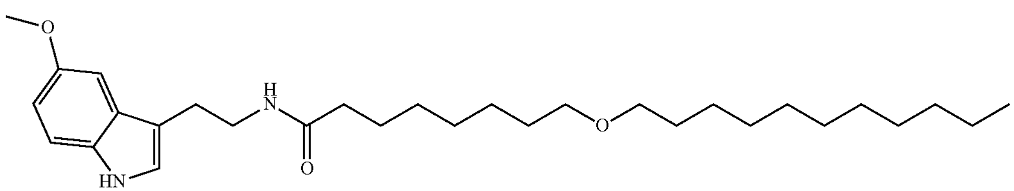 [SMILES: CCCCCCCCCCCOCCCCCCCC(=O)NCCc1c[nH]c2ccc(OC)cc12] | N-[2-(5-methoxy-1H-indol-3-yl)ethyl]-8-(undecyloxy)octanamide |

TABLE 1-continued
Exemplary Compounds
| Compound Number | Compound Structure | Compound Name |
|---|---|---|
| I-5 | 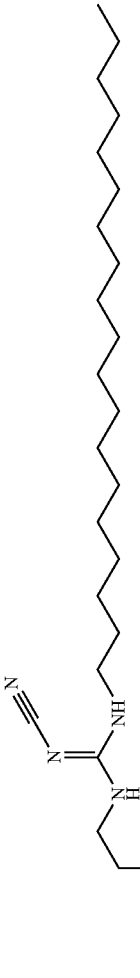 | 2-cyano-3-[2-(1H-indol-3-yl)ethyl]-1-nonadecylguanidine |
| I-6 | 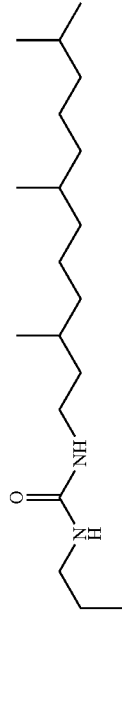 | 1-[2-(1H-indol-3-yl)ethyl]-3-(3,7,11-trimethyldodecyl)urea |
| I-7 | 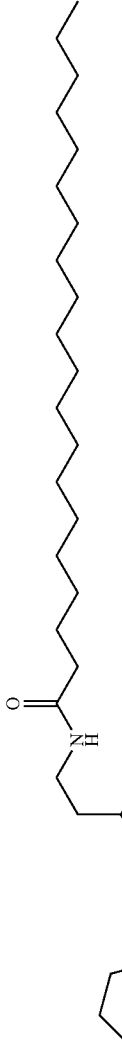 | N-{2-[5-(morpholin-4-yl)-1H-indol-3-yl]ethyl}icosamide |
| I-8 | 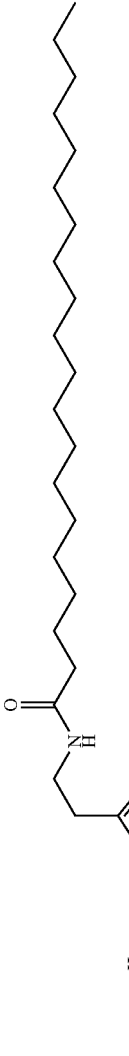 | N-{2-[5-(cyclopentylamino)-1H-indol-3-yl]ethyl}icosamide |

TABLE 1-continued
Exemplary Compounds
| Compound Number | Compound Structure | Compound Name |
|---|---|---|
| I-9 | 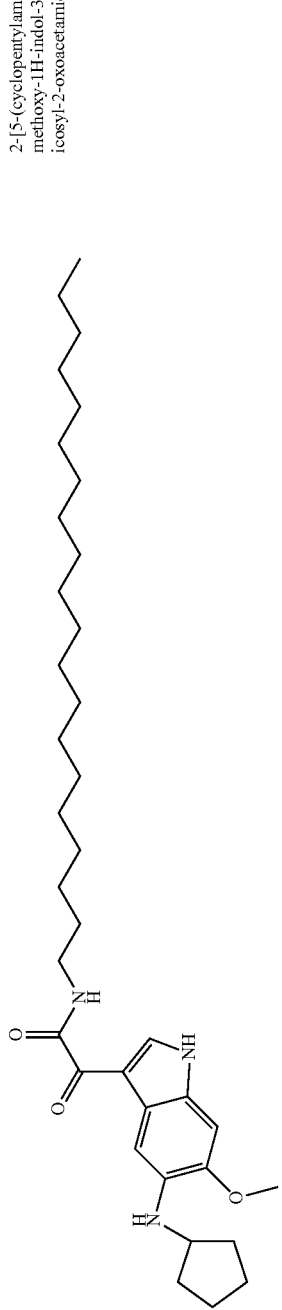 | 2-[5-(cyclopentylamino)-6-methoxy-1H-indol-3-yl]-N-icosyl-2-oxoacetamide |
| I-10 | 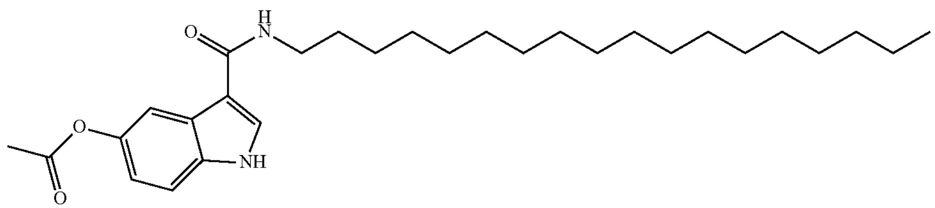 [SMILES: CCCCCCCCCCCCCCCCCCNC(=O)c1c[nH]c2ccc(OC(C)=O)cc12] | 3-(octadecylcarbamoyl)-1H-indol-5-yl acetate |
| I-11 | 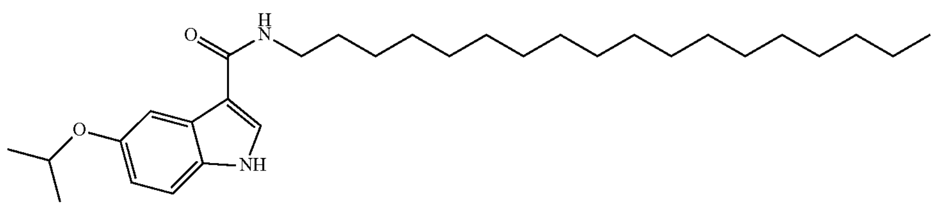 [SMILES: CCCCCCCCCCCCCCCCCCNC(=O)c1c[nH]c2ccc(OC(C)C)cc12] | N-octadecyl-5-(propan-2-yloxy)-1H-indole-3-carboxamide |
| I-12 | 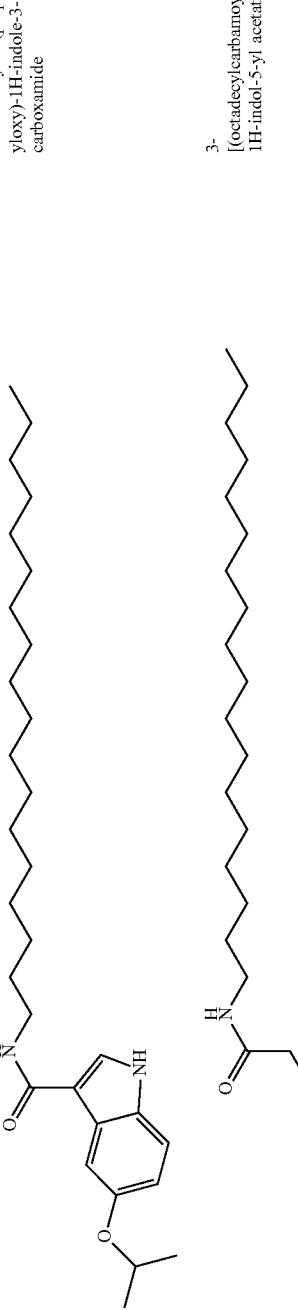 | 3-[(octadecylcarbamoyl)methyl]-1H-indol-5-yl acetate |

TABLE 1-continued

Exemplary Compounds

| Compound Number | Compound Structure | Compound Name |
|---|---|---|
| I-13 | 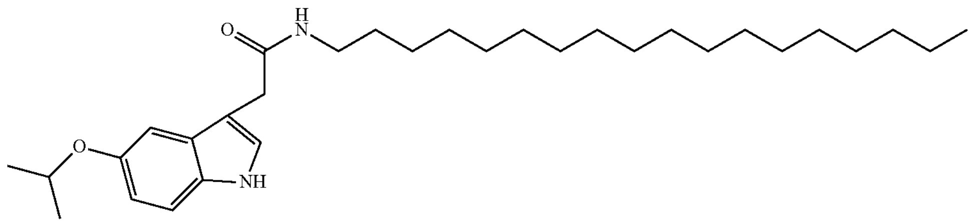 [SMILES: CCCCCCCCCCCCCCCCCCNC(=O)Cc1c[nH]c2ccc(OC(C)C)cc12] | N-octadecyl-2-[5-(propan-2-yloxy)-1H-indol-3-yl]acetamide |
| I-14 | 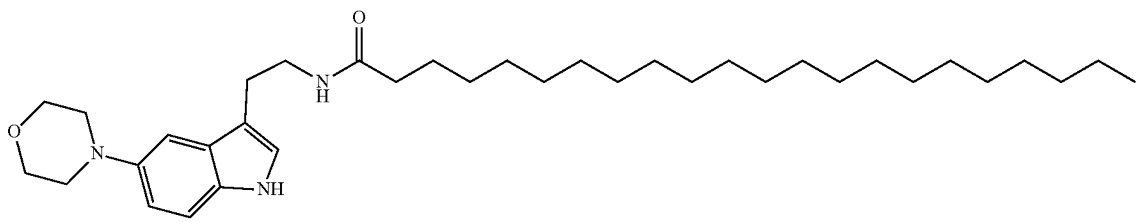 [SMILES: CCCCCCCCCCCCCCCCCCCCCC(=O)NCCc1c[nH]c2ccc(N3CCOCC3)cc12] | N-{2-[5-(morpholin-4-yl)-1H-indol-3-yl]ethyl}docosanamide |
| I-15 | 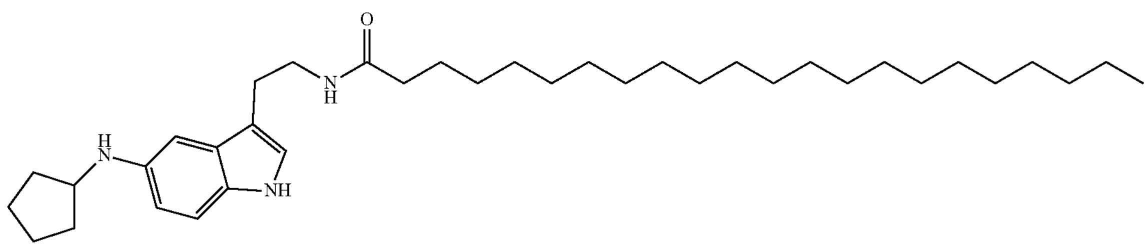 [SMILES: CCCCCCCCCCCCCCCCCCCCCC(=O)NCCc1c[nH]c2ccc(NC3CCCC3)cc12] | N-{2-[5-(cyclopentylamino)-1H-indol-3-yl]ethyl}docosanamide |
| I-16 | 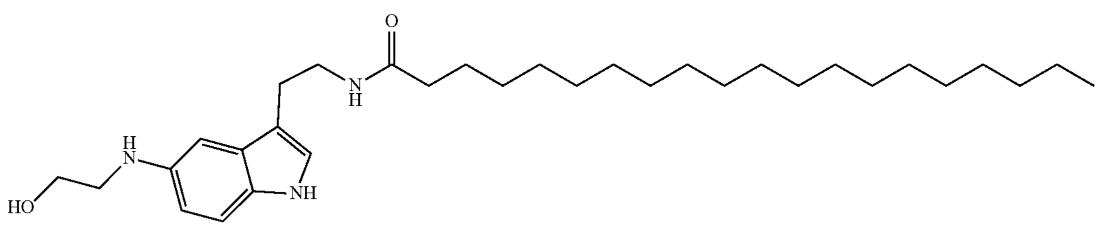 [SMILES: CCCCCCCCCCCCCCCCCCCC(=O)NCCc1c[nH]c2ccc(NCCO)cc12] | N-(2-{5-[(2-hydroxyethyl)amino]-1H-indol-3-yl}ethyl)icosanamide |

TABLE 1-continued

Exemplary Compounds

| Compound Number | Compound Structure | Compound Name |
|---|---|---|
| I-17 | 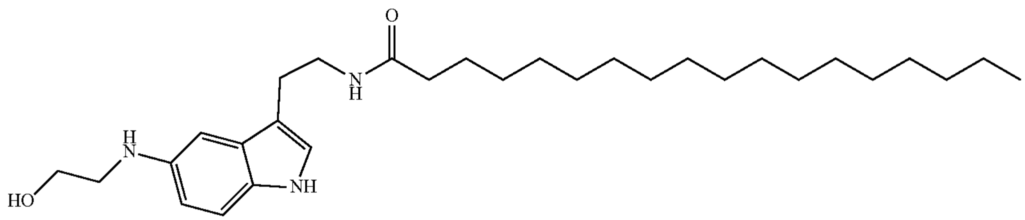 [SMILES: CCCCCCCCCCCCCCCCCC(=O)NCCc1c[nH]c2ccc(NCCO)cc12] | N-(2-{5-[(2-hydroxyethyl)amino]-1H-indol-3-yl}ethyl)octadecanamide |
| I-18 | 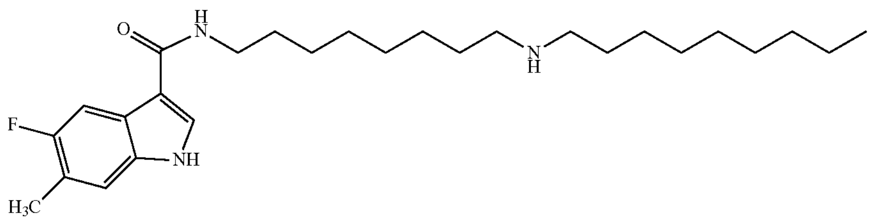 [SMILES: CCCCCCCCCNCCCCCCCCNC(=O)c1c[nH]c2cc(C)c(F)cc12] | 5-fluoro-6-methyl-N-[8-(nonylamino)octyl]-1H-indole-3-carboxamide |
| I-19 | 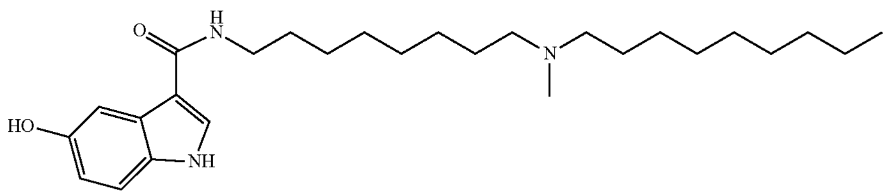 [SMILES: CCCCCCCCCN(C)CCCCCCCCNC(=O)c1c[nH]c2ccc(O)cc12] | 5-hydroxy-N-{8-[methyl(nonyl)amino]octyl}-1H-indole-3-carboxamide |
| I-20 | 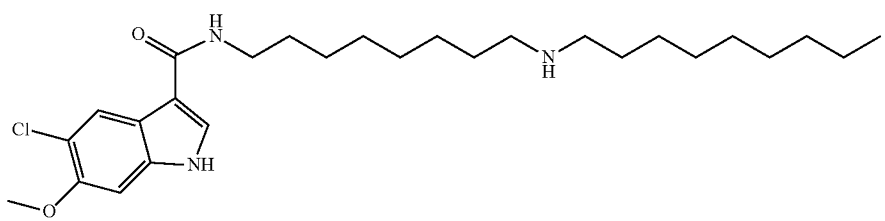 [SMILES: CCCCCCCCCNCCCCCCCCNC(=O)c1c[nH]c2cc(OC)c(Cl)cc12] | 5-chloro-6-methoxy-N-[8-(nonylamino)octyl]-1H-indole-3-carboxamide |

TABLE 1-continued

Exemplary Compounds

| Compound Number | Compound Structure | Compound Name |
|---|---|---|
| I-21 | 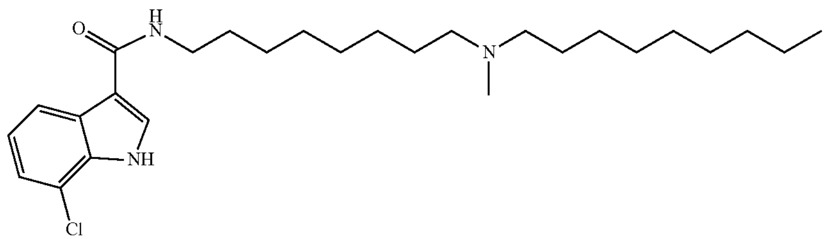 [SMILES: CCCCCCCCCCCCCCCCCCNC(=O)c1c[nH]c2c(F)cccc12] | 7-chloro-N-{8-[methyl(nonyl)amino]octyl}-1H-indole-3-carboxamide |
| I-22 | 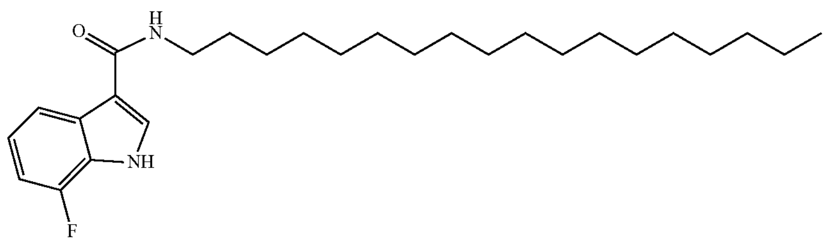 | 7-fluoro-N-octadecyl-1H-indole-3-carboxamide |
| I-23 | 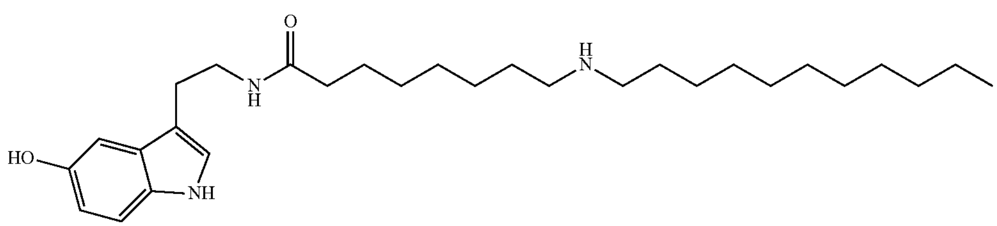 [SMILES: CCCCCCCCCCCNCCCCCCCC(=O)NCCc1c[nH]c2ccc(O)cc12] | N-[2-(5-hydroxy-1H-indol-3-yl)ethyl]-8-(undecylamino)octanamide |
| I-24 | 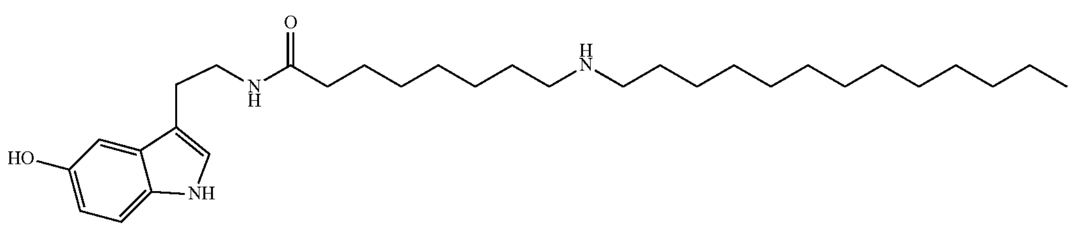 [SMILES: CCCCCCCCCCCCCNCCCCCCCC(=O)NCCc1c[nH]c2ccc(O)cc12] | N-[2-(5-hydroxy-1H-indol-3-yl)ethyl]-8-(tridecylamino)octanamide |

TABLE 1-continued

Exemplary Compounds

| Compound Number | Compound Structure | Compound Name |
|---|---|---|
| I-25 | 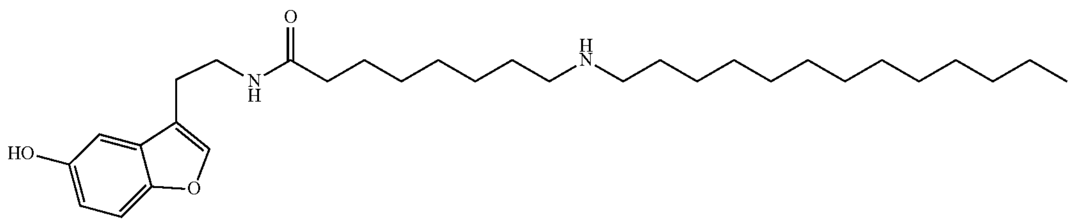 [SMILES: CCCCCCCCCCCCCNCCCCCCCC(=O)NCCc1coc2ccc(O)cc12] | N-[2-(5-hydroxy-1-benzofuran-3-yl)ethyl]-8-(tridecylamino)octanamide |
| I-26 | 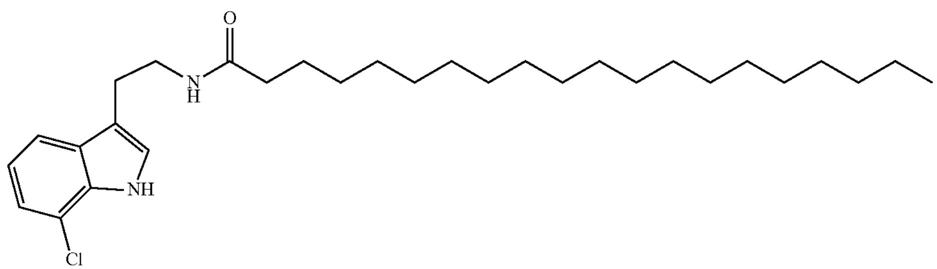 [SMILES: CCCCCCCCCCCCCCCCCCCC(=O)NCCc1c[nH]c2c(Cl)cccc12] | N-[2-(7-chloro-1H-indol-3-yl)ethyl]icosanamide |
| I-27 | 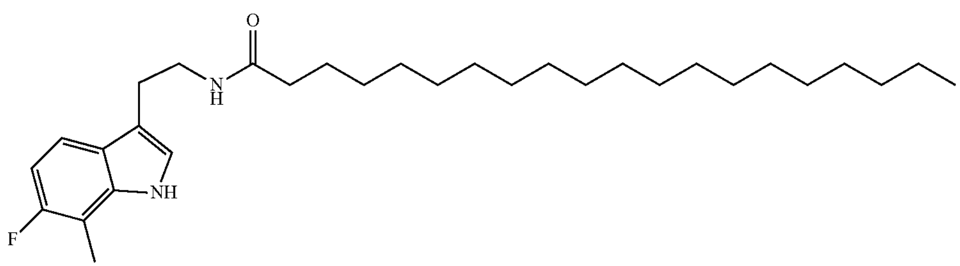 [SMILES: CCCCCCCCCCCCCCCCCCCC(=O)NCCc1c[nH]c2c(C)c(F)ccc12] | N-[2-(6-fluoro-7-methyl-1H-indol-3-yl)ethyl]icosanamide |

TABLE 1-continued
Exemplary Compounds
| Compound Number | Compound Structure | Compound Name |
|---|---|---|
| I-28 | 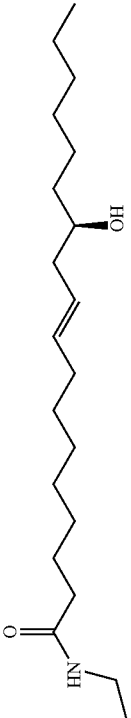 | (9Z,12S)-12-hydroxy-N-[2-(5-hydroxy-1H-indol-3-yl)ethyl]octadec-9-enamide |
| I-29 | 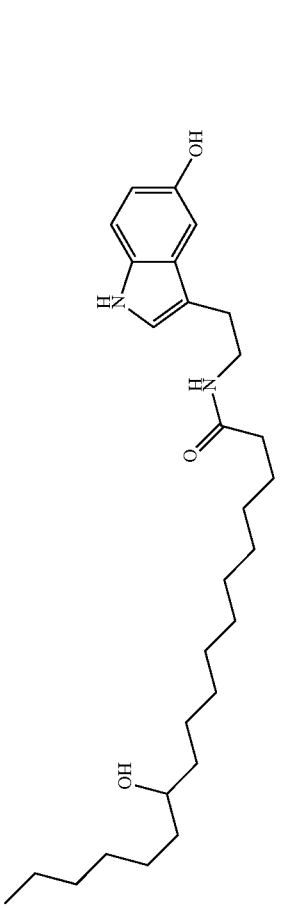 | 12-hydroxy-N-[2-(5-hydroxy-1H-indol-3-yl)ethyl]octadecanamide |
| I-30 | 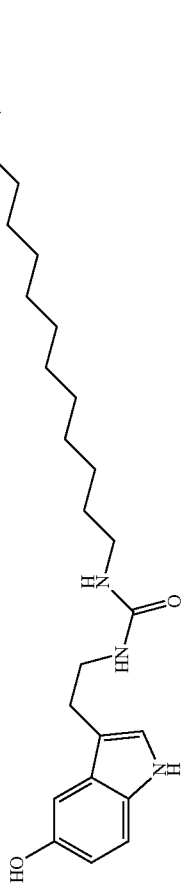 | 3-hexadecyl-1-[2-(5-hydroxy-1H-indol-3-yl)ethyl]urea |

TABLE 1-continued

Exemplary Compounds

| Compound Number | Compound Structure | Compound Name |
|---|---|---|
| I-31 | 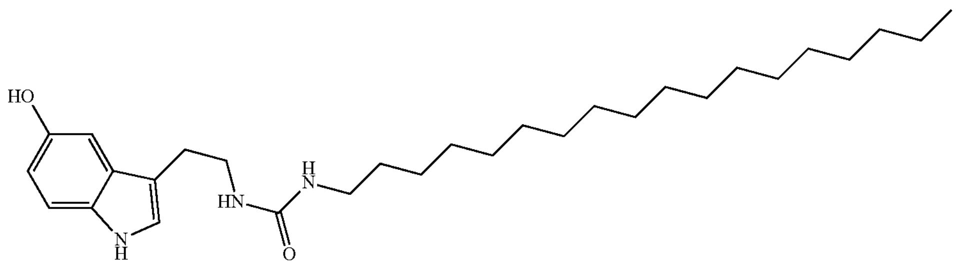 [SMILES: CCCCCCCCCCCCCCCCCCNC(=O)NCCc1c[nH]c2ccc(O)cc12] | 1-[2-(5-hydroxy-1H-indol-3-yl)ethyl]-3-octadecylurea |
| I-32 | 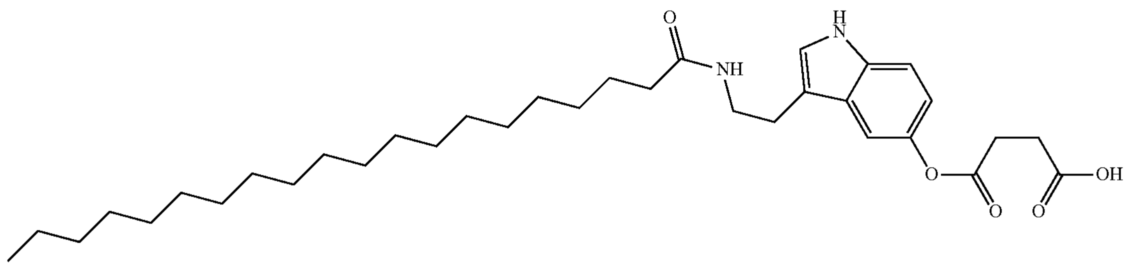 [SMILES: CCCCCCCCCCCCCCCCCCCC(=O)NCCc1c[nH]c2ccc(OC(=O)CCC(=O)O)cc12] | 4-{[3-(2-icosanamidoethyl)-1H-indol-5-yl]oxy}-4-oxobutanoic acid |
| I-33 | 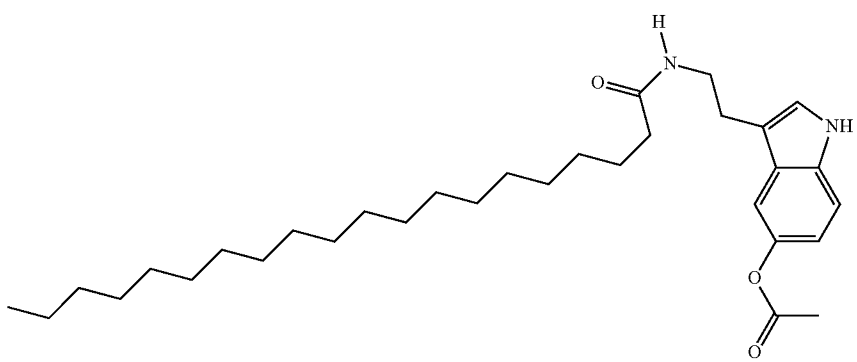 [SMILES: CCCCCCCCCCCCCCCCCCCC(=O)NCCc1c[nH]c2ccc(OC(C)=O)cc12] | 3-(2-icosanamidoethyl)-1H-indol-5-yl acetate |

TABLE 1-continued

Exemplary Compounds

| Compound Number | Compound Structure | Compound Name |
|---|---|---|
| I-34 | 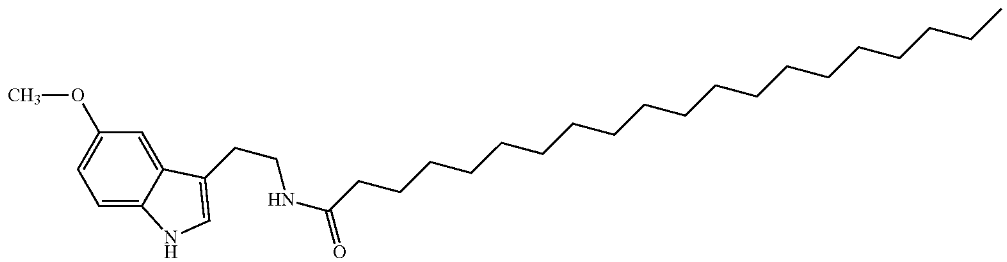 [SMILES: CCCCCCCCCCCCCCCCCCCC(=O)NCCc1c[nH]c2ccc(OC)cc12] | N-[2-(5-methoxy-1H-indol-3-yl)ethyl]icosanamide |
| I-35 | 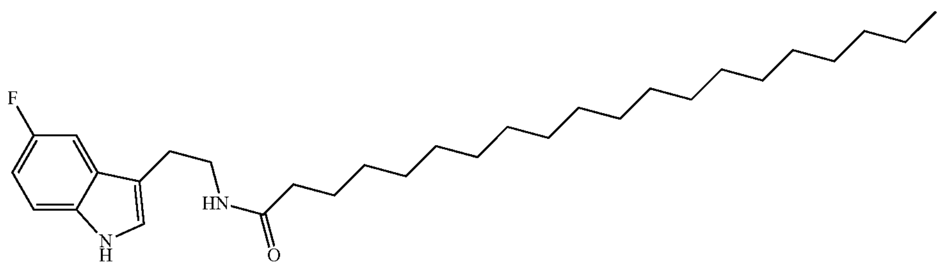 [SMILES: CCCCCCCCCCCCCCCCCCCC(=O)NCCc1c[nH]c2ccc(F)cc12] | N-[2-(5-fluoro-1H-indol-3-yl)ethyl]icosanamide |
| I-36 | 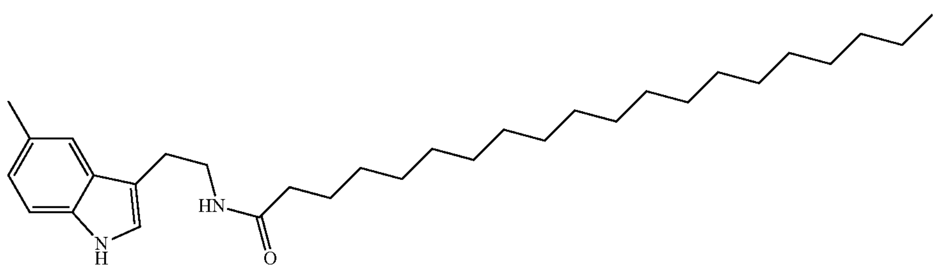 [SMILES: CCCCCCCCCCCCCCCCCCCC(=O)NCCc1c[nH]c2ccc(C)cc12] | N-[2-(5-methyl-1H-indol-3-yl)ethyl]icosanamide |

TABLE 1-continued

Exemplary Compounds

| Compound Number | Compound Structure | Compound Name |
|---|---|---|
| I-37 | 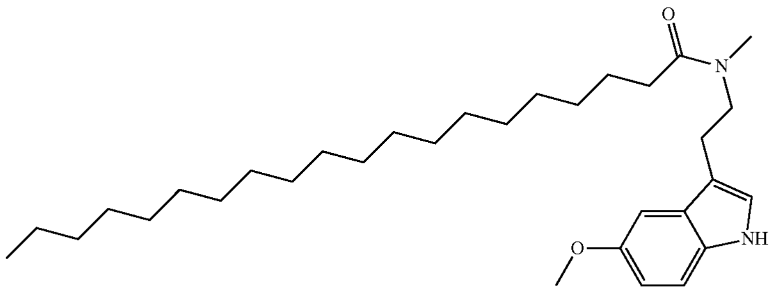 [SMILES: CCCCCCCCCCCCCCCCCCCC(=O)N(C)CCc1c[nH]c2ccc(OC)cc12] | N-[2-(5-methoxy-1H-indol-3-yl)ethyl]-N-methylicosanamide |
| I-38 | 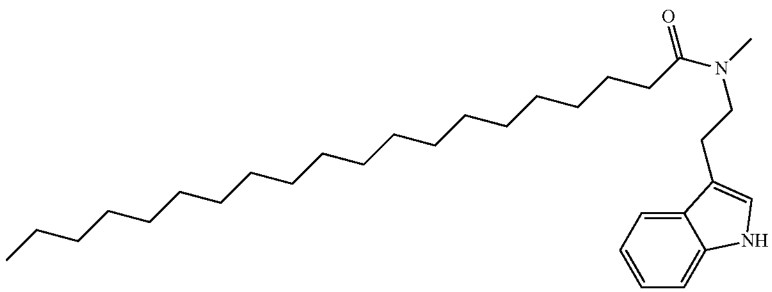 [SMILES: CCCCCCCCCCCCCCCCCCCC(=O)N(C)CCc1c[nH]c2ccccc12] | N-[2-(1H-indol-3-yl)ethyl]-N-methylicosanamide |
| I-39 | 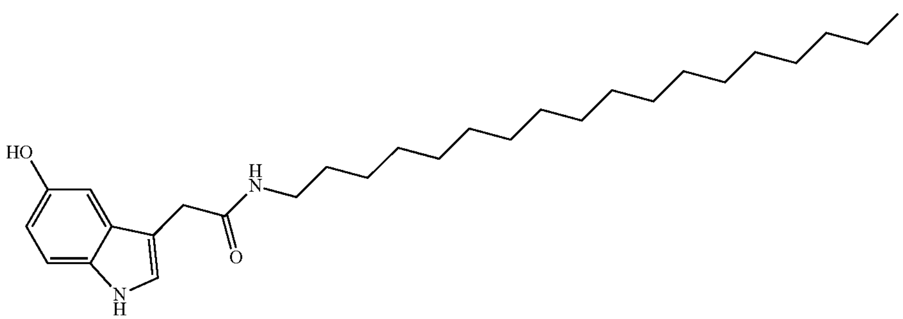 [SMILES: CCCCCCCCCCCCCCCCCCNC(=O)Cc1c[nH]c2ccc(O)cc12] | 2-(5-hydroxy-1H-indol-3-yl)-N-octadecylacetamide |

TABLE 1-continued
Exemplary Compounds
| Compound Number | Compound Structure | Compound Name |
|---|---|---|
| I-40 | 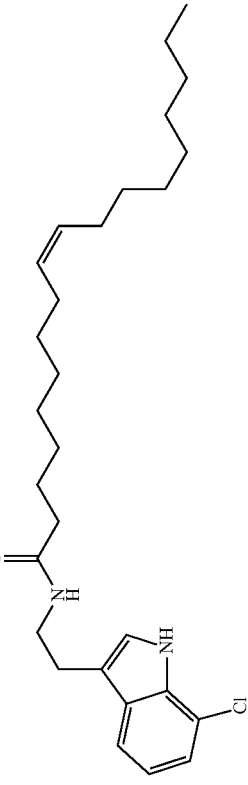 | (9Z)-N-[2-(7-chloro-1H-indol-3-yl)ethyl]octadec-9-enamide |
| I-41 | 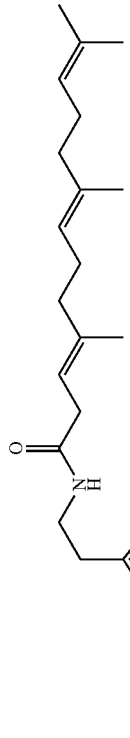 | (3E,7E)-N-[2-(5-hydroxy-1H-indol-3-yl)ethyl]-4,8,12-trimethyltrideca-3,7,11-trienamide |
| I-42 | 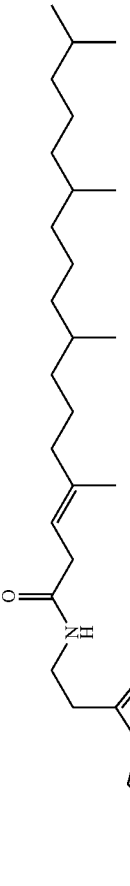 | (3E)-N-[2-(5-hydroxy-1H-indol-3-yl)ethyl]-4,8,12,16-tetramethylheptadec-3-enamide |
| I-43 | 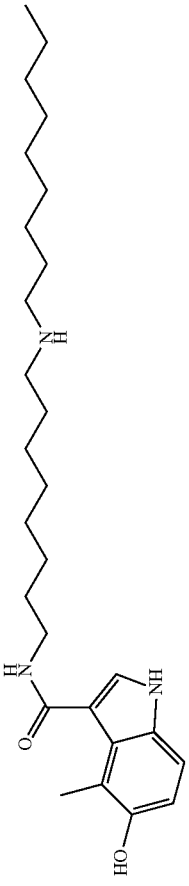 | 5-hydroxy-4-methyl-N-[8-(nonylamino)octyl]-1H-indole-3-carboxamide |

TABLE 1-continued

Exemplary Compounds

| Compound Number | Compound Structure | Compound Name |
|---|---|---|
| I-44 | 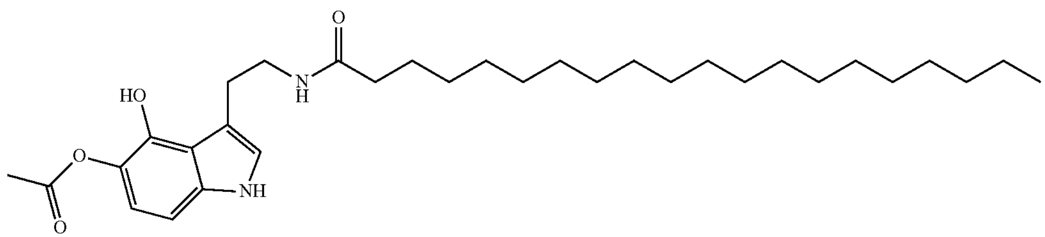 [SMILES: CCCCCCCCCCCCCCCCCCCC(=O)NCCc1c[nH]c2ccc(OC(C)=O)c(O)c12] | 4-hydroxy-3-(2-icosanamidoethyl)-1H-indol-5-yl acetate |
| I-45 | 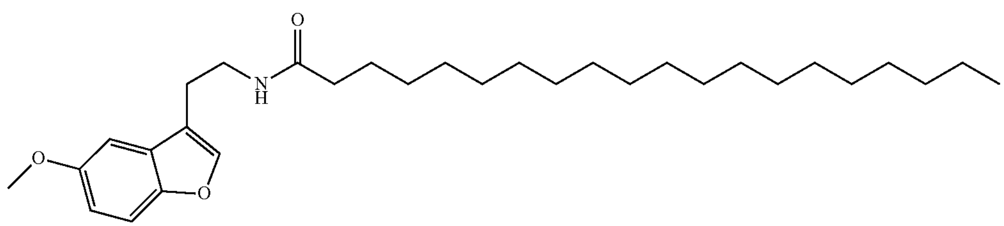 [SMILES: CCCCCCCCCCCCCCCCCCCC(=O)NCCc1coc2ccc(OC)cc12] | N-[2-(5-methoxy-1-benzofuran-3-yl)ethyl]icosanamide |
| I-46 | 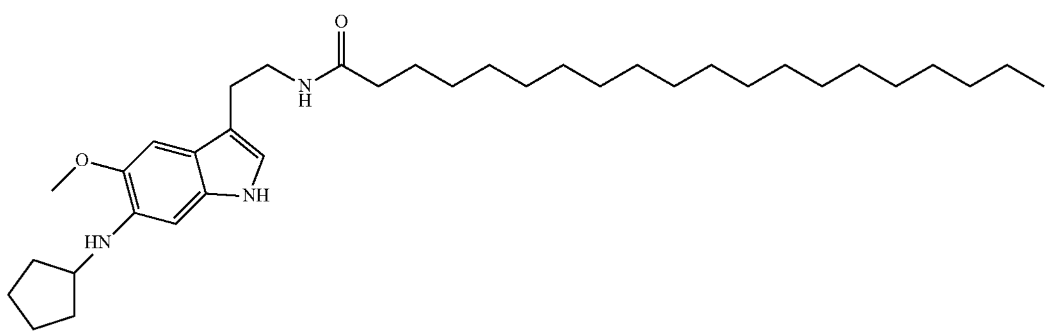 [SMILES: CCCCCCCCCCCCCCCCCCCC(=O)NCCc1c[nH]c2cc(NC3CCCC3)c(OC)cc12] | N-{2-[6-(cyclopentylamino)-5-methoxy-1H-indol-3-yl]ethyl}icosanamide |

TABLE 1-continued

Exemplary Compounds

| Compound Number | Compound Structure | Compound Name |
|---|---|---|
| I-47 | 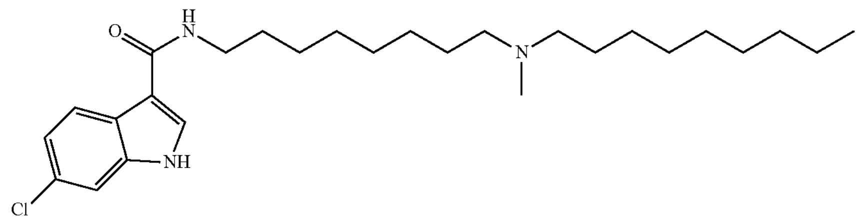 [SMILES: CCCCCCCCCN(C)CCCCCCCCNC(=O)c1c[nH]c2cc(Cl)ccc12] | 6-chloro-N-{8-[methyl(nonyl)amino]octyl}-1H-indole-3-carboxamide |
| I-48 | 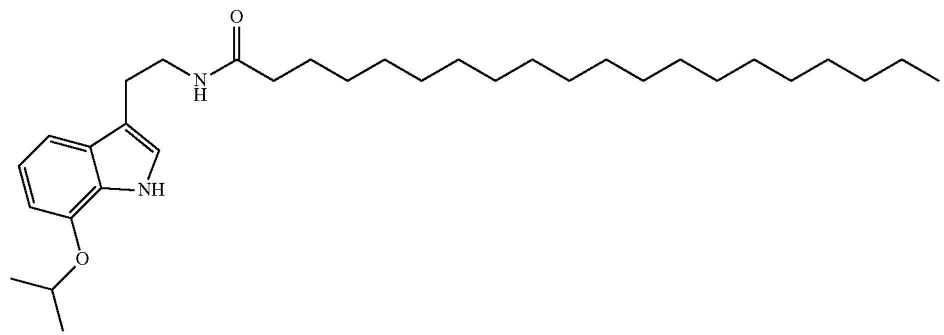 [SMILES: CCCCCCCCCCCCCCCCCCCC(=O)NCCc1c[nH]c2c(OC(C)C)cccc12] | N-{2-[7-(propan-2-yloxy)-1H-indol-3-yl]ethyl}icosanamide |
| I-49 | 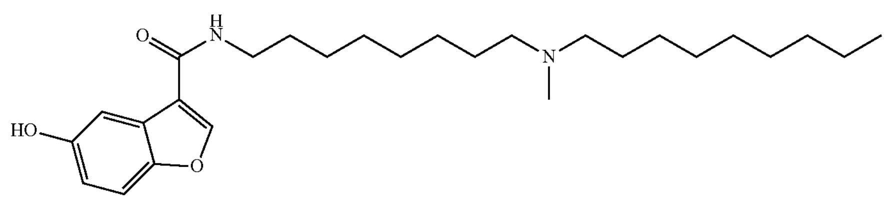 [SMILES: CCCCCCCCCN(C)CCCCCCCCNC(=O)c1coc2ccc(O)cc12] | 5-hydroxy-N-{8-[methyl(nonyl)amino]octyl}-1-benzothiophene-3-carboxamide |
| I-50 | 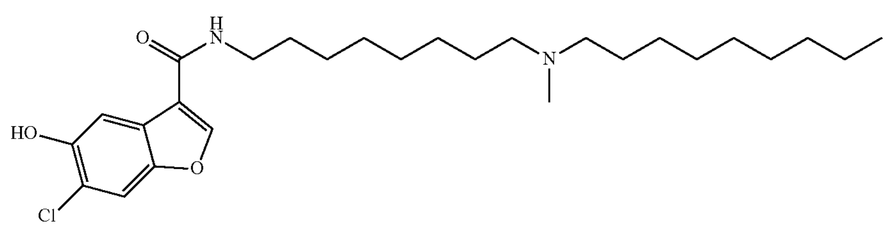 [SMILES: CCCCCCCCCN(C)CCCCCCCCNC(=O)c1coc2cc(Cl)c(O)cc12] | 6-chloro-5-hydroxy-N-{8-[methyl(nonyl)amino]octyl}-1-benzofuran-3-carboxamide |

TABLE 1-continued

Exemplary Compounds

| Compound Number | Compound Structure | Compound Name |
|---|---|---|
| I-51 | 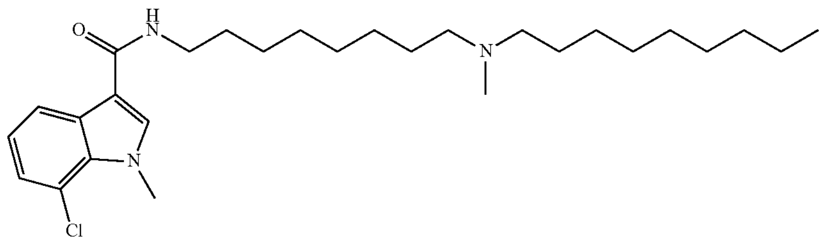 [SMILES: CCCCCCCCCN(C)CCCCCCCCNC(=O)c1cn(C)c2c(Cl)cccc12] | 7-chloro-1-methyl-N-{8-[methyl(nonyl)amino]octyl}-1H-indole-3-carboxamide |
| I-52 | 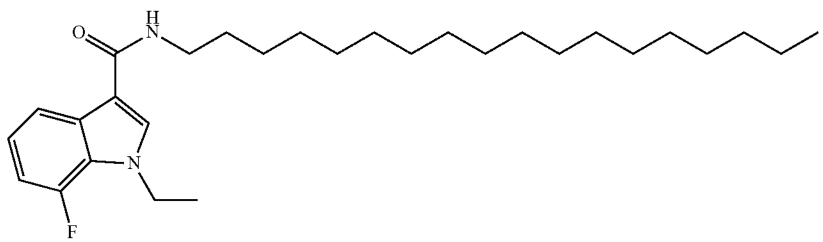 [SMILES: CCCCCCCCCCCCCCCCCCNC(=O)c1cn(CC)c2c(F)cccc12] | 1-ethyl-7-fluoro-N-octadecyl-1H-indole-3-carboxamide |
| I-53 | 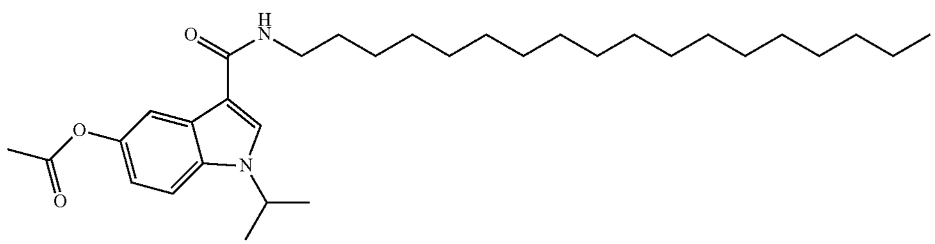 [SMILES: CCCCCCCCCCCCCCCCCCNC(=O)c1cn(C(C)C)c2ccc(OC(C)=O)cc12] | 3-(octadecylcarbamoyl)-1-(propan-2-yl)-1H-indol-5-yl acetate |
| I-54 | 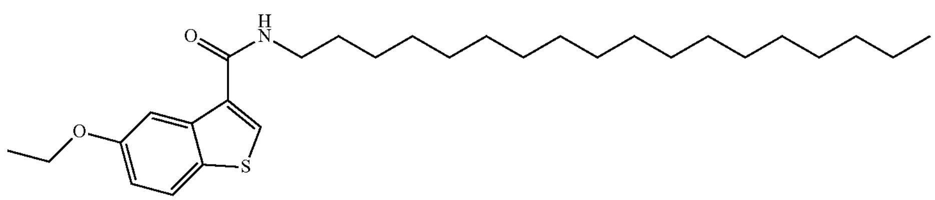 [SMILES: CCCCCCCCCCCCCCCCCCNC(=O)c1csc2ccc(OCC)cc12] | 5-ethoxy-N-octadecyl-1-benzothiophene-3-carboxamide |

TABLE 1-continued
Exemplary Compounds
| Compound Number | Compound Structure | Compound Name |
|---|---|---|
| I-55 | 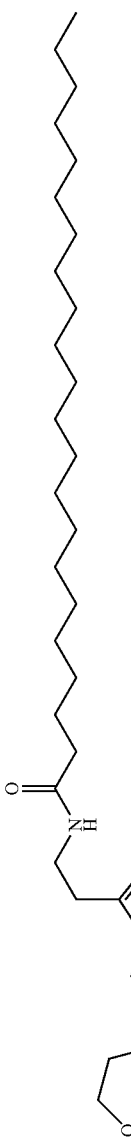 | N-{2-[5-(morpholin-4-yl)-1-benzothiophen-3-yl]ethyl}docosanamide |
| I-56 | 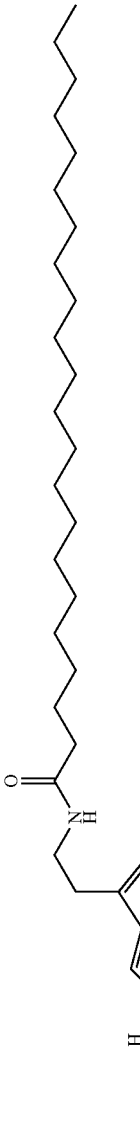 | N-{2-[5-(cyclopentylamino)-1-ethyl-1H-indol-3-yl]ethyl}docosanamide |
| I-57 | 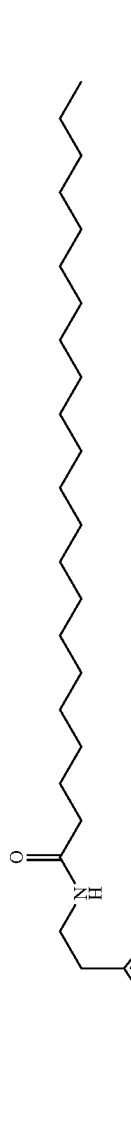 | N-[2-(5-hydroxy-1-methyl-1H-indol-3-yl)ethyl]docosanamide |
| I-58 | 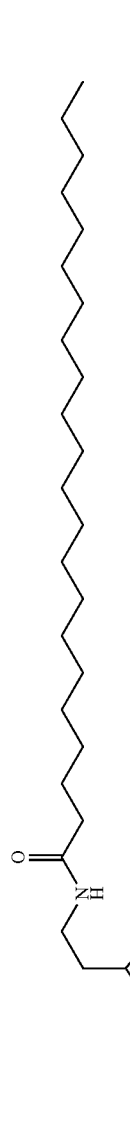 | N-[2-(5-hydroxy-1-benzothiophen-3-yl)ethyl]docosanamide |

TABLE 1-continued

Exemplary Compounds

| Compound Number | Compound Structure | Compound Name |
|---|---|---|
| I-59 | 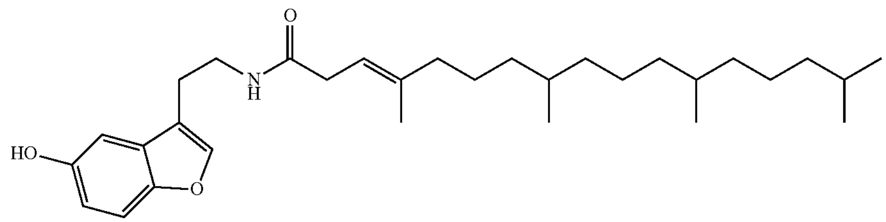 [SMILES: C/C(=C\CC(=O)NCCc1coc2ccc(O)cc12)CCCC(C)CCCC(C)CCCC(C)C] | (3E)-N-[2-(5-hydroxy-1-benzofuran-3-yl)ethyl]-4,8,12,16-tetramethylheptadec-3-enamide |
| I-60 | 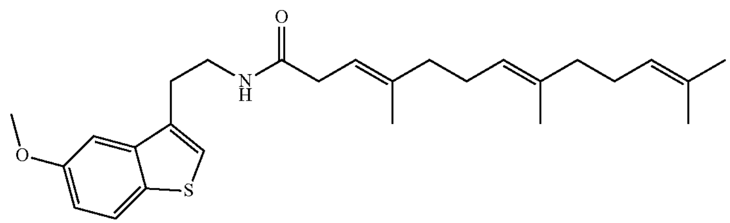 [SMILES: COc1ccc2scc(CCNC(=O)C/C=C(\C)CC/C=C(\C)CCC=C(C)C)c2c1] | (3E,7E)-N-[2-(5-methoxy-1-benzothiphen-3-yl)ethyl]-4,8,12-trimethyltrideca-3,7,11-trienamide |
| I-61 | 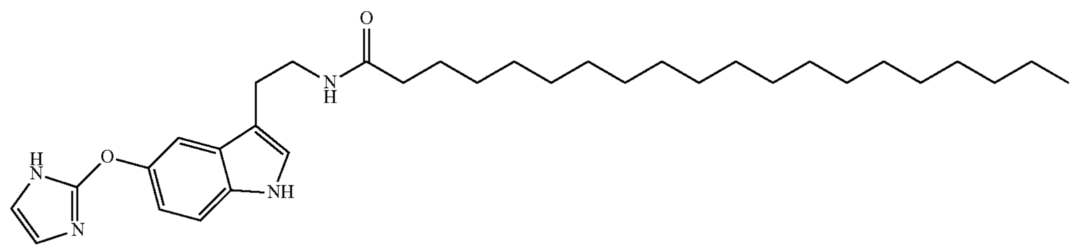 [SMILES: CCCCCCCCCCCCCCCCCCCC(=O)NCCc1c[nH]c2ccc(Oc3ncc[nH]3)cc12] | N-{2-[5-(1H-imidazol-2-yloxy)-1H-indol-3-yl]ethyl}icosanamide |
| I-62 | 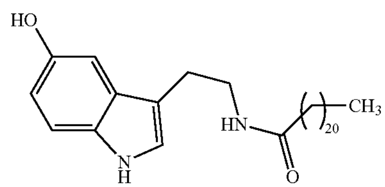 | N-(2-(5-hydroxy-1H-indol-3-yl)ethyl)docosanamide |

TABLE 1-continued

Exemplary Compounds

| Compound Number | Compound Structure | Compound Name |
|---|---|---|
| I-63* | 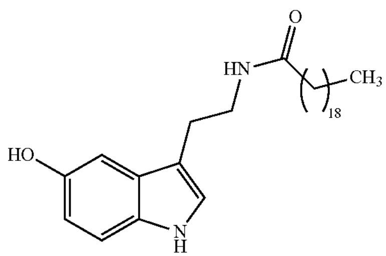 | N-(2-(5-hydroxy-1H-indol-3-yl)ethyl)icosanamide |
| I-64* | 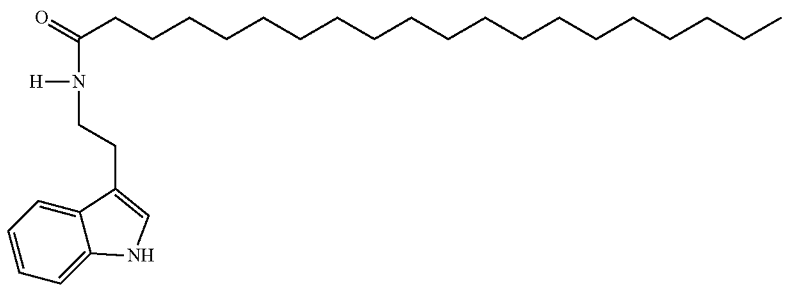 [SMILES: CCCCCCCCCCCCCCCCCCCC(=O)NCCc1c[nH]c2ccccc12] | N-(2-(1H-indol-3-yl)ethyl)icosanamide |
| I-65* | 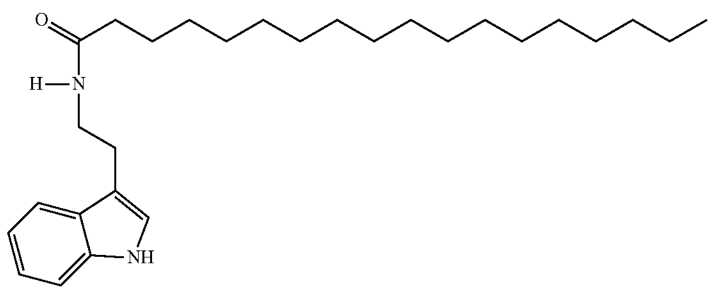 [SMILES: CCCCCCCCCCCCCCCCCC(=O)NCCc1c[nH]c2ccccc12] | N-(2-(1H-indol-3-yl)ethyl)stearamide |

TABLE 1-continued

Exemplary Compounds

| Compound Number | Compound Structure | Compound Name |
|---|---|---|
| I-66* | 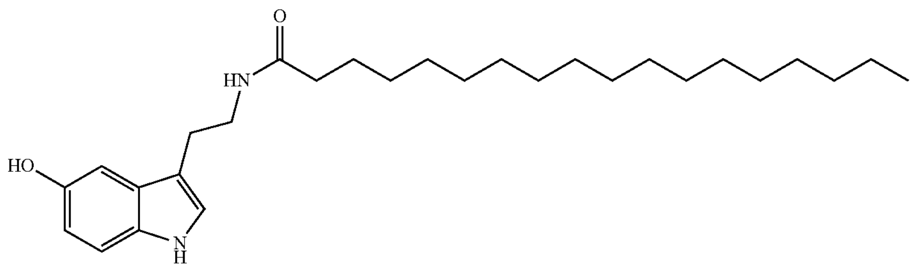 [SMILES: CCCCCCCCCCCCCCCCCC(=O)NCCc1c[nH]c2ccc(O)cc12] | N-(2-(5-hydroxy-1H-indol-3-yl)ethyl)stearamide |
| I-67* | 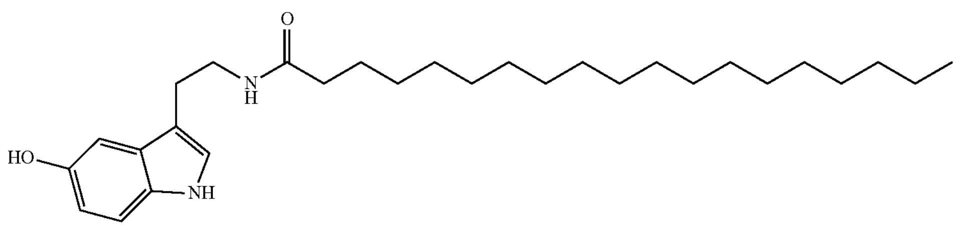 [SMILES: CCCCCCCCCCCCCCCCCCC(=O)NCCc1c[nH]c2ccc(O)cc12] | N-(2-(5-hydroxy-1H-indol-3-yl)ethyl)nonadecanamide |
| I-68* | 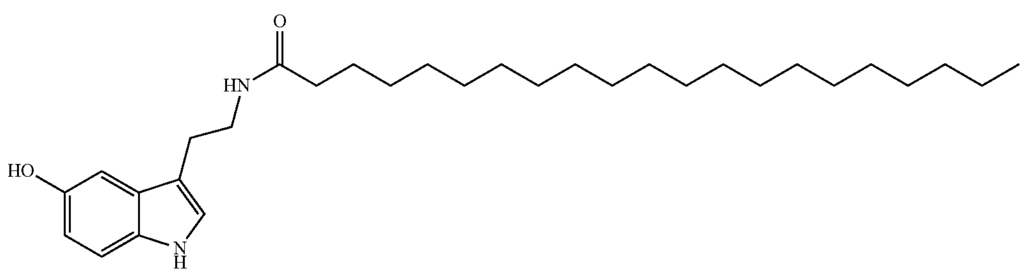 [SMILES: CCCCCCCCCCCCCCCCCCCCC(=O)NCCc1c[nH]c2ccc(O)cc12] | N-(2-(5-hydroxy-1H-indol-3-yl)ethyl)henicosanamide |

TABLE 1-continued

Exemplary Compounds

| Compound Number | Compound Structure | Compound Name |
|---|---|---|
| I-69* | 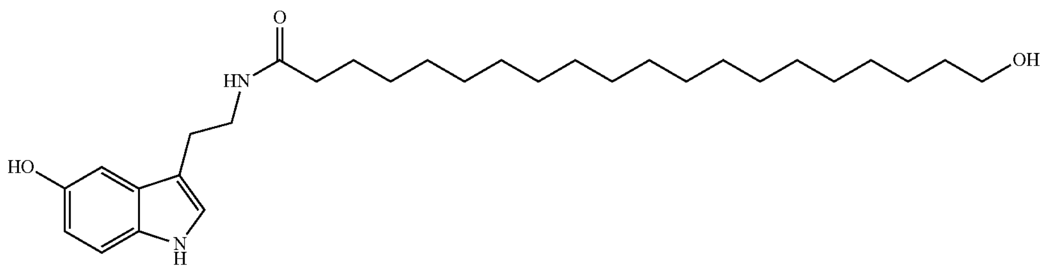 [SMILES: O=C(CCCCCCCCCCCCCCCCCCCO)NCCc1c[nH]c2ccc(O)cc12] | 20-hydroxy-N-(2-(5-hydroxy-1H-indol-3-yl)ethyl)icosanamide |
| I-70* | 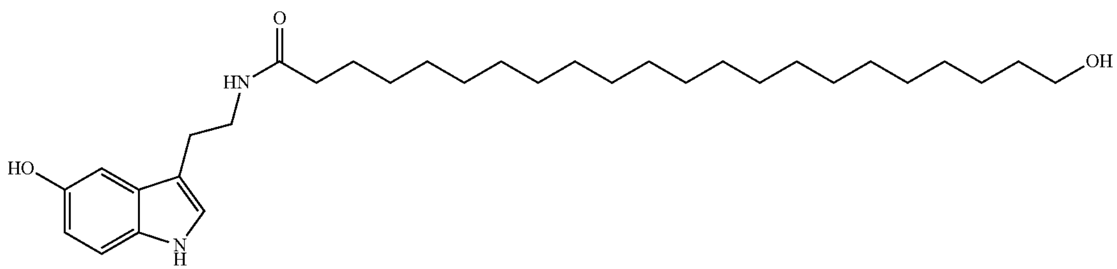 [SMILES: O=C(CCCCCCCCCCCCCCCCCCCCCO)NCCc1c[nH]c2ccc(O)cc12] | 22-hydroxy-N-(2-(5-hydroxy-1H-indol-3-yl)ethyl)docosanamide |
| I-71* | 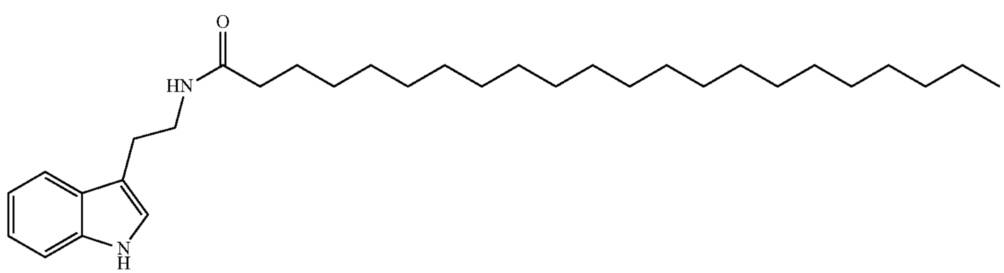 [SMILES: CCCCCCCCCCCCCCCCCCCCCC(=O)NCCc1c[nH]c2ccccc12] | N-(2-(1H-indol-3-yl)ethyl)docosanamide |

TABLE 1-continued

Exemplary Compounds

| Compound Number | Compound Structure | Compound Name |
|---|---|---|
| I-72* | 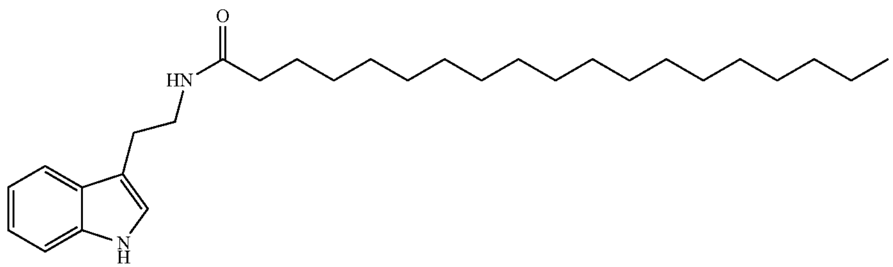 [SMILES: CCCCCCCCCCCCCCCCCCC(=O)NCCc1c[nH]c2ccccc12] | N-(2-(1H-indol-3-yl)ethyl)nonadecanamide |
| I-76 | 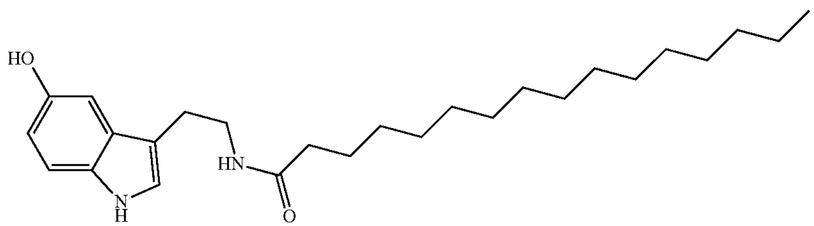 [SMILES: CCCCCCCCCCCCCCCC(=O)NCCc1c[nH]c2ccc(O)cc12] | N-(2-(5-hydroxy-1H-indol-3-yl)ethyl)palmitamide |
| I-77 | 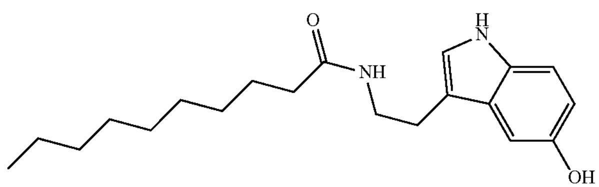 [SMILES: CCCCCCCCCC(=O)NCCc1c[nH]c2ccc(O)cc12] | N-(2-(5-hydroxy-1H-indol-3-yl)ethyl)decanamide |
| I-78 | 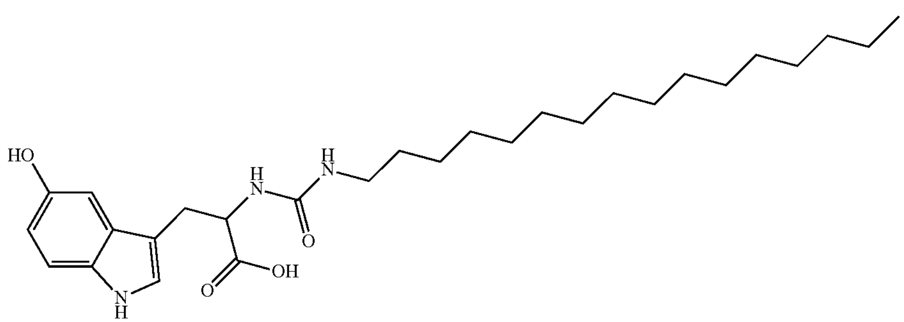 [SMILES: CCCCCCCCCCCCCCCCNC(=O)NC(Cc1c[nH]c2ccc(O)cc12)C(=O)O] | 2-(3-hexadecylureido)-3-(5-hydroxy-1H-indol-3-yl)propanoic acid |

TABLE 1-continued
Exemplary Compounds
| Compound Number | Compound Structure | Compound Name |
|---|---|---|
| I-79 | 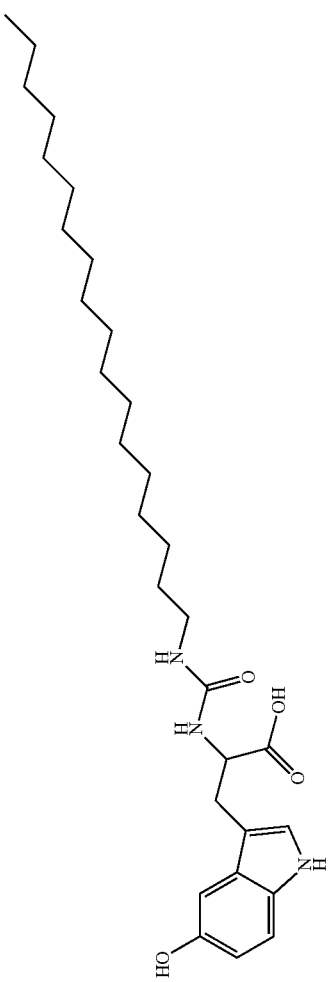 | 3-(5-hydroxy-1H-indol-3-yl)-2-(3-octadecylureido)propanoic acid |
| I-80 | 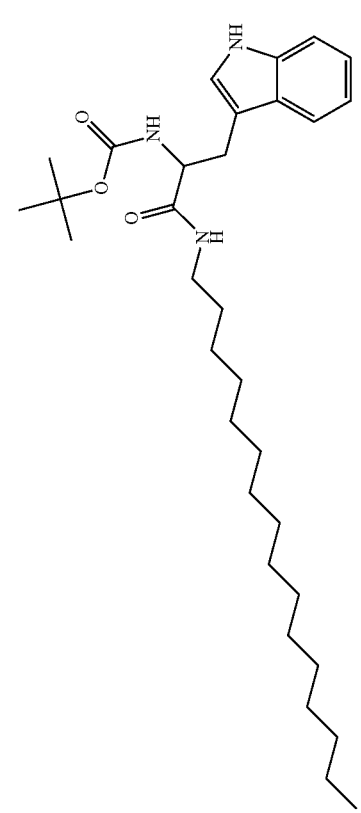 | tert-butyl 1-(hexadecylamino)-3-(1H-indol-3-yl)-1-oxopropan-2-ylcarbamate |

TABLE 1-continued

Exemplary Compounds

| Compound Number | Compound Structure | Compound Name |
|---|---|---|
| I-81* | 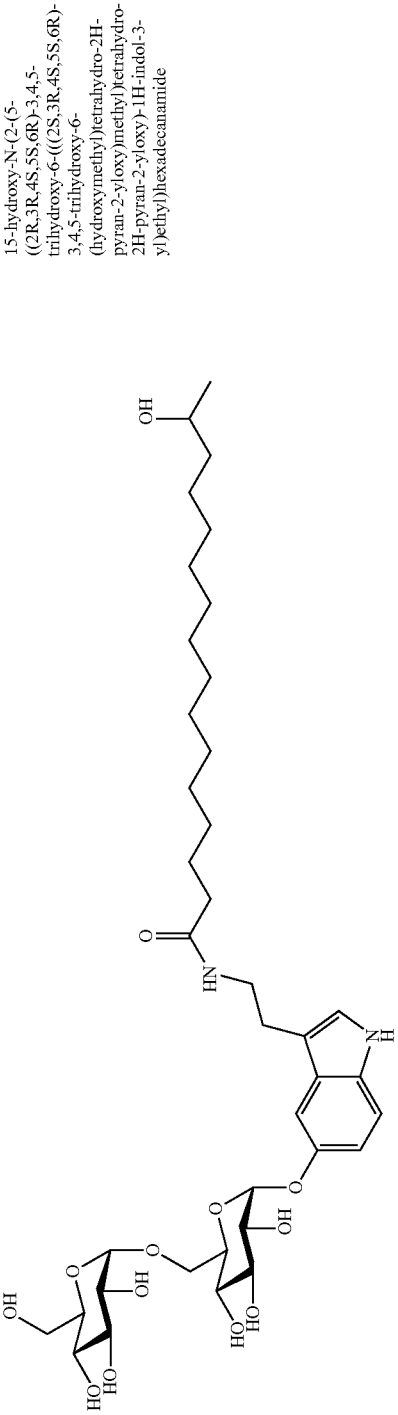 | 15-hydroxy-N-(2-(5-((2R,3R,4S,5S,6R)-3,4,5-trihydroxy-6-(((2S,3R,4S,5S,6R)-3,4,5-trihydroxy-6-(hydroxymethyl)tetrahydro-2H-pyran-2-yloxy)methyl)tetrahydro-2H-pyran-2-yloxy)-1H-indol-3-yl)ethyl)hexadecanamide |
| I-82* | 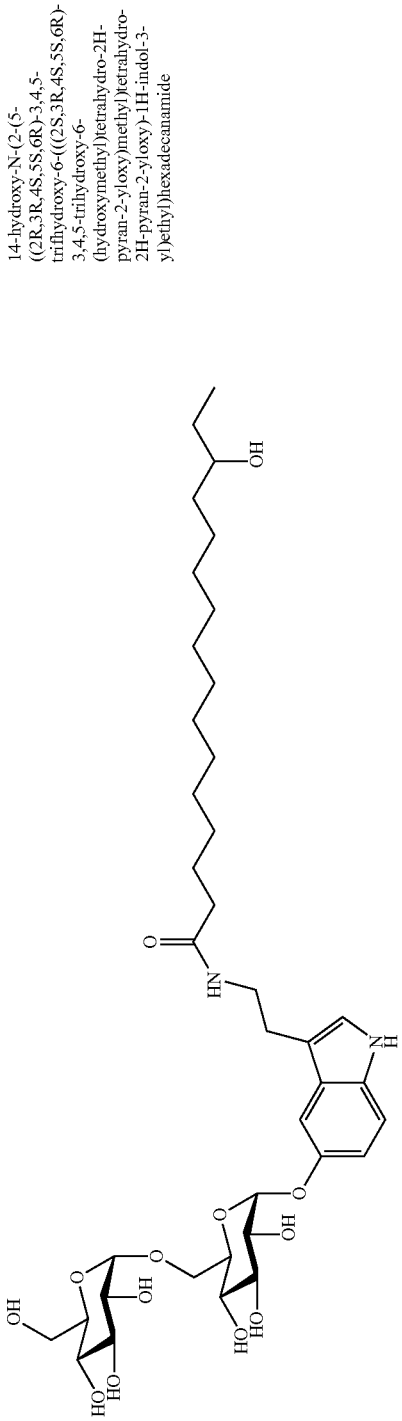 | 14-hydroxy-N-(2-(5-((2R,3R,4S,5S,6R)-3,4,5-trihydroxy-6-(((2S,3R,4S,5S,6R)-3,4,5-trihydroxy-6-(hydroxymethyl)tetrahydro-2H-pyran-2-yloxy)methyl)tetrahydro-2H-pyran-2-yloxy)-1H-indol-3-yl)ethyl)hexadecanamide |

TABLE 1-continued

Exemplary Compounds

| Compound Number | Compound Structure | Compound Name |
|---|---|---|
| I-83* | 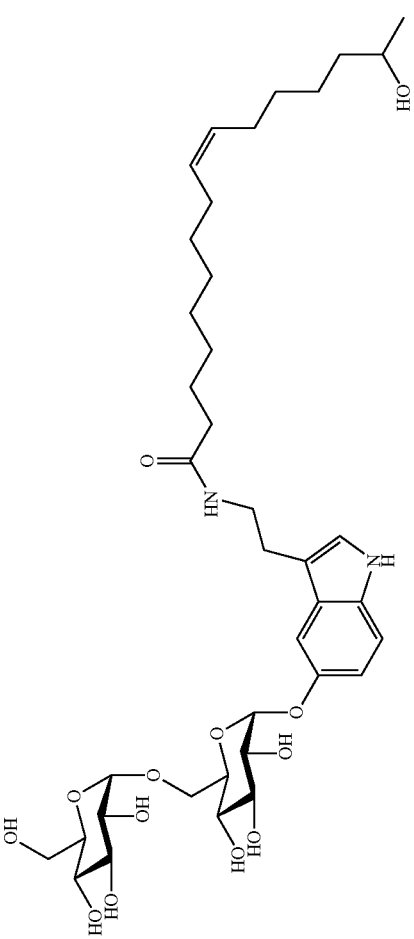 | (Z)-15-hydroxy-N-(2-(5-((2R,3R,4S,5S,6R)-3,4,5-trihydroxy-6-(((2S,3R,4S,5S,6R)-3,4,5-trihydroxy-6-(hydroxymethyl)tetrahydro-2H-pyran-2-yloxy)methyl)tetrahydro-2H-pyran-2-yloxy)-1H-indol-3-yl)ethyl)hexadec-9-enamide |
| I-84* | 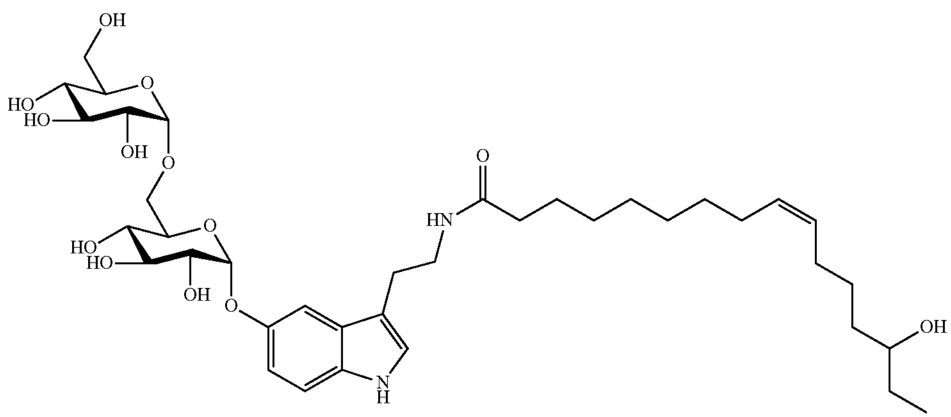 | (Z)-14-hydroxy-N-(2-(5-((2R,3R,4S,5S,6R)-3,4,5-trihydroxy-6-(((2S,3R,4S,5S,6R)-3,4,5-trihydroxy-6-(hydroxymethyl)tetrahydro-H-pyran-2-yloxy)methyl)tetrahydro-2H-pyran-2-yloxy)-1H-indol-3-yl)ethyl)hexadec-9-enamide |

TABLE 1-continued

Exemplary Compounds

| Compound Number | Compound Structure | Compound Name |
|---|---|---|
| I-85* | 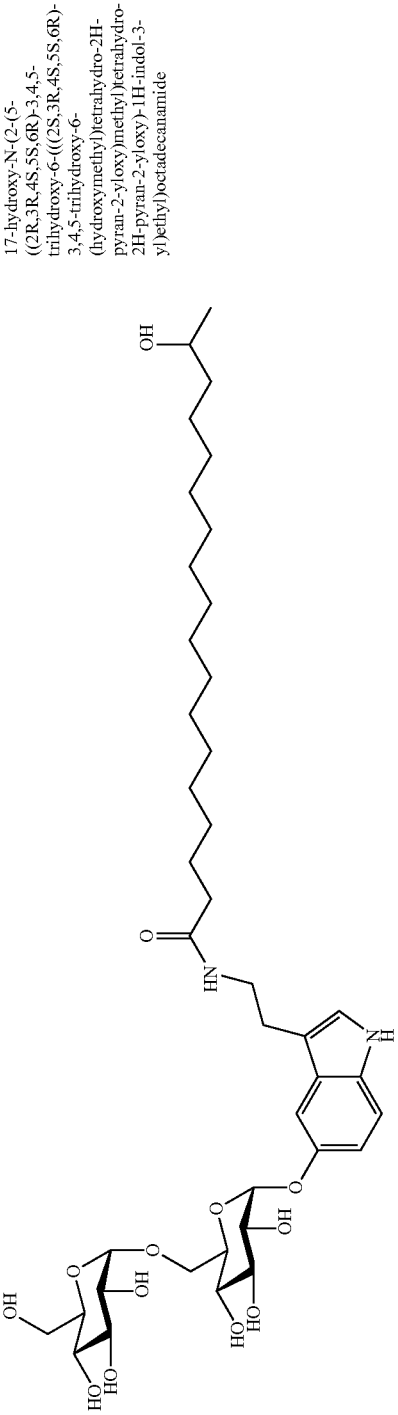 | 17-hydroxy-N-(2-(5-((2R,3R,4S,5S,6R)-3,4,5-trihydroxy-6-(((2S,3R,4S,5S,6R)-3,4,5-trihydroxy-6-(hydroxymethyl)tetrahydro-2H-pyran-2-yloxy)methyl)tetrahydro-2H-pyran-2-yloxy)-1H-indol-3-yl)ethyl)octadecanamide |
| I-86* | 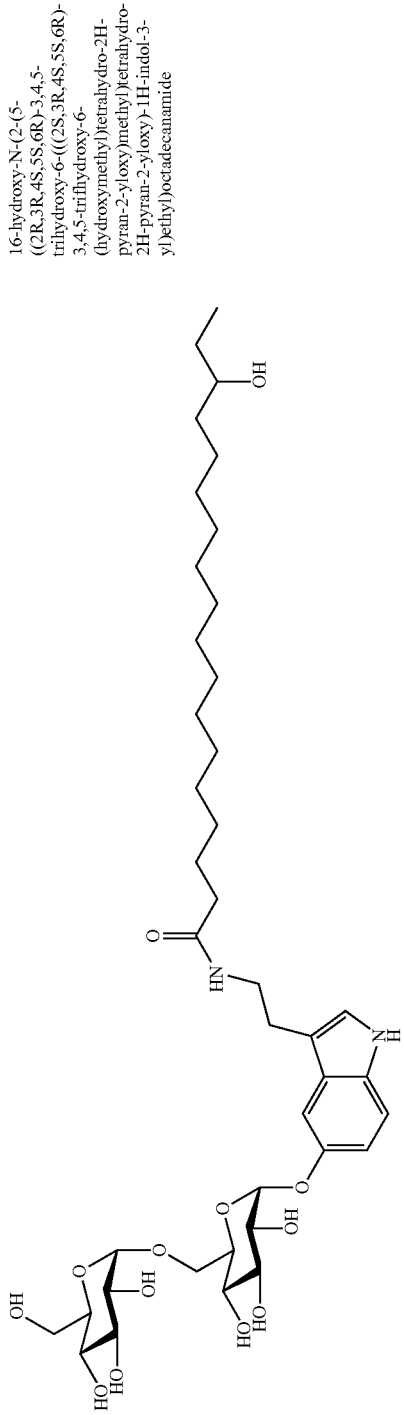 | 16-hydroxy-N-(2-(5-((2R,3R,4S,5S,6R)-3,4,5-trihydroxy-6-(((2S,3R,4S,5S,6R)-3,4,5-trihydroxy-6-(hydroxymethyl)tetrahydro-2H-pyran-2-yloxy)methyl)tetrahydro-2H-pyran-2-yloxy)-1H-indol-3-yl)ethyl)octadecanamide |

In certain embodiments, the present invention provides any compound depicted in Table 1, above, or a pharmaceutically acceptable salt thereof.

Compounds of the above described formulae may be provided according to the present invention in any of a variety of useful forms, for example as pharmaceutically acceptable salts, as particular crystal forms, etc. In some embodiments, prodrugs of one or more compounds of the above described formulae are provided. Various forms of prodrugs are known in the art, for example as discussed in Bundgaard (ed.), *Design of Prodrugs*, Elsevier (1985); Widder et al. (ed.), *Methods in Enzymology*, vol. 4, Academic Press (1985); Kgrogsgaard-Larsen et al. (ed.); *"Design and Application of Prodrugs"*, Textbook of Drug Design and Development, Chapter 5, 113-191 (1991); Bundgaard et al., *Journal of Drug Delivery Reviews*, 8:1-38 (1992); Bundgaard et al., *J Pharmaceutical Sciences*, 77:285 et seq. (1988); and Higuchi and Stella (eds.), *Prodrugs as Novel Drug Delivery Systems*, American Chemical Society (1975).

Provided herein are compounds of formula I that can exist in a variety of solid forms. Such forms include neat crystal forms, known as polymorphs. Such solid forms also include solvates, hydrates, anhydrous forms and amorphous. Such solid forms of a compound of formula I are contemplated as within this disclosure. In certain embodiments, provided is a compound of formula I as a mixture of one or more different solid forms (e.g., polymorphs, solvates and amorphous compound analogs).

Certain compounds of the present invention the above described formulae may exist in particular geometric or stereoisomeric forms. The present invention encompasses all such compounds, including cis- and trans-isomers, R- and S-enantiomers, diastereomers, (D)-isomers, (L)-isomers, the racemic mixtures thereof, and other mixtures thereof, as falling within the scope of the invention. It will be appreciated that asymmetric carbon atoms may be present in a substituent such as an alkyl group, such that different isomers of a particular compound may exist due to different configurations of a substituent. All such isomers, as well as mixtures thereof, are intended to be included in this invention. In some embodiments, the present invention provides individual isomeric [e.g., geometric (or conformational), stereoisomeric] compound forms (and/or compositions containing them); in some embodiments, the present invention provides compositions comprising two or more isomeric (e.g., geometric or steroisomeric) forms. Unless otherwise stated, all tautomeric forms of the compounds of the invention are within the scope of the invention. Additionally, unless otherwise stated, the present invention encompasses compounds that differ only in the presence of one or more isotopically enriched atoms from structures depicted herein. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In some embodiments, the fatty acid, fatty acid mimic moiety, heterocyclic moiety or a tether group group in the above described formulae comprises one or more deuterium atoms. Mixtures of isomeric forms may be separated and/or purified by techniques as would be known to one skilled in this art, including but not limited to column chromatography.

Those of ordinary skill in the art will appreciate that compositions containing two or isomeric forms of a compound may contain such different forms in particular relative amounts. For example, compositions containing only two isomers may include such isomers at ratios such as: 50:50, 60:40, 70:30, 80:20, 90:10, 95:5, 96:4, 97:3, 98:2, 99:1, or 100:0 isomer ratios. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

According to the present invention, compounds described herein can modulate PP2A activity and/or can have any of a variety of interesting biological activities. Such activities can be tested, assessed, and/or utilized using isolated compounds or using compounds in a composition (e.g., an extract, a comestible composition, a pharmaceutical composition, etc.). Examples included herein describe biological activities of various compounds of formula I.

Compounds that modulate PP2A activity can function by various mechanisms. To give but a few examples of possible mechanisms, compounds that modulate PP2A activity may modulate the methylation of PP2A, modulate the demethylation of PP2A, modulate the interaction of PP2A substrates with PP2A, modulate the interaction of auxiliary proteins with PP2A and/or directly interact with PP2A, etc II. Methods of Preparation A. Synthetic Preparation of Compounds Some compounds of formula I occur in nature and may be prepared or isolated from natural sources. In some embodiments, such compounds are prepared or isolated from extracts obtained from a botanical source. As will be appreciated by those of ordinary skill in the art, representative such botanical sources include, for example, coffee (e.g., from green coffee beans, roasted coffee beans, spent ground coffee beans, coffee wax, etc.), chocolate, *withania somnifera* (fruit), Butcher's broom (root), coconut, *ginkgo biloba, bacopa monniera, nigella sativa*, St. John's wort, *annova atemoya* (seeds), and *scorodocarpus, borneesis* (fruit). Those of ordinary skill in the art are well familiar with a wide array of separation and isolation techniques useful in the preparation of compounds of formula I from natural extracts (e.g., botanical extracts).

The present invention provides synthetic methodologies for preparing compounds of formula I and/or compositions containing compounds of formula I, derivatives and synthetic intermediates thereof. As will be understood by those in the art, the provision of chemical synthesis methodologies allows access to a wide range of compounds that may not be found in nature and cannot be isolated or prepared from natural sources. Thus, the present invention provides methodologies that allow for the preparation of compounds of formula I and/or compositions containing compounds of formula I, derivatives and synthetic intermediates thereof that were previously not available.

In certain embodiments, the present compounds are generally preparing according to Scheme I set forth below:

Scheme I

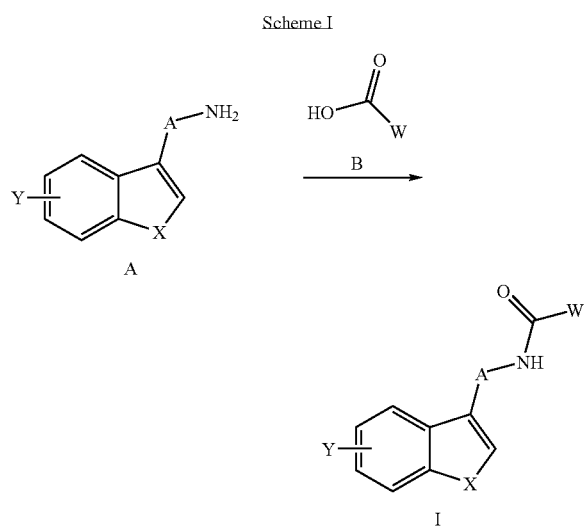

In Scheme I above, each of $R^1$, $R^2$, n, and $R^3$ is as defined herein.

In certain embodiments, the present invention provides methods for preparing compounds of formula I according to the step described in Scheme I above. In this step, an amine compound of formula A is coupled to an acid compound of formula B. Such coupling of a carboxylic acid with an amine can be performed using methods well known to one of ordinary skill in the art.

In certain embodiments, the acid compound of formula B is activated prior to coupling. In certain embodiments, the carboxylic acid moiety of the acid compound of formula B is treated with a suitable reagent to form an acid halide prior to coupling. In certain embodiments, the suitable reagent is thionyl chloride. In certain embodiments, the acid halide is then coupled to the amine moiety of the amine compound of formula A, to form a compound of formula I. In certain embodiments, the suitable reagent is thionyl iodide. In certain embodiments, the acid halide is then coupled to the amine moiety of the amine compound of formula A, to form a compound of formula I. In certain embodiments, the suitable reagent is oxalyl chloride. In certain embodiments, the acid halide is then coupled to the amine moiety of the amine compound of formula A, to form a compound of formula I. In certain embodiments, the acid compound of formula B is treated with hydroxybenzotriazole (HOBt) to form the activated acid compound of formula B thereof, which is then coupled to the amine moiety of the amine compound of formula A, to form a compound of formula I. In certain embodiments, the acid compound of formula B is treated with a heterocyclic base to form the activated acid compound of formula B thereof which is then coupled to the amine moiety of the amine compound of formula A, to form a compound of formula I. In certain embodiments, the acid compound of formula B is treated with heterocyclic acid to form the activated acid compound of formula B thereof, which is then coupled to the amine moiety of the amine compound of formula A, to form a compound of formula I. In certain embodiments, the acid compound of formula B is treated with an organic base to form the activated acid compound of formula B thereof which is then coupled to the amine moiety of the amine compound of formula A, to form a compound of formula I. Such activated acid compound of formula B can be performed using other methods well known to one of ordinary skill in the art, e.g., see "Comprehensive Organic Transformations—A Guide to Functional Group Preparations," Richard C. Larock, $2^{nd}$ Ed., pp. 1929-1932, John Wiley & Sons, Inc. New York (1999).

In certain embodiments, the coupling is achieved with a suitable coupling agent. Such reagents are well known in the art and include, for example, benzotriazol-1-yl-oxy-tris-(dimethylamino)-phosphonium hexafluorphosphate (BOP), N,N'-carbonyldiimidazole (CDI), N,N'-dicyclohhexylcarbodiimide (DCC), N,N'-diisopropylcarbodiimide (DIC), 3-(diethoxyphosphoryloxy)-1,2,3-benzotriazin-4-(3H)-one (DEPBT), N-ethyl-N'-(3-dimethylaminopropyl)carbodiimide hydrochloride (EDC) or (EDAC), 2-(1H-benzotriazol-1-yl)-1,1,3,3-tetramethyluronoium hexafluorphosphate (HBTU), 2-(3,4-dihydro-4-oxo-1,2,3-benzotriazin-3-yl)-N,N,N',N'-tetramethyluronium hexafluorophosphate (HDBTU), 2-(mercaptobenzothiazol)-N,N,N',N'-tetramethyluronium hexafluorophosphate (HMTU), 2-(endo-5-norbornene-2,3-dicarboxymido)-1,1,3,3-tetramethyluronium hexafluorophosphate (HNTU), 1-hydroxibenzotriazol monohydrate (HOBt*1H₂O), 1-hydroxy-1H-1,2,3-Triazole-4-carboxylate (HOCt), N-hydroxy-5-norbornene-2,3-dicarboxylimide (HONB), 3-hydroxy-3,4-dihydro-4-oxo-1,2,3-benzotriazine (HOOBt), S-(1-oxido-2-pyridyl)-thio-N,N,N',N'-tetramethyluronium hexafluorophosphate (HOTT), O-succinimidyl-1,3-dimethylpropyleneuronium hexafluorophosphate (HPD-OSu), S-(1-oxo-2-pyridyl)-thio-1,3-dimethylpropyleneuronium hexafluorophosphate (HPTDP), O-(1,2-dihydro-2-oxo-pyridyl]-N,N,N',N'-tetramethyluronium hexafluorophosphate (HPTU), 2-succinimido-1,1,3,3-tetramethyluronium hexafluorophosphate (HSTU), 4-(4,6-dimethoxy-1,3,5-triazin-2-yl)-4-morpholinium tetrafluoroborate (MMTM), 1-(mesitylene-2-sulfonyl)-3-nitro-1,2,4-triazole (MSNT), pentafluorphenol-tetramethyluronium hexafluorophosphate (PFTU), tris-n-propan-phosphonic acid anhydride (50% in AcOEt) (PPAA/AcOEt), tris-n-propan-phosphonic acid anhydride (50% in DMF) (PPAA/DMF), 2-(1H-benzotriazole-1-yl)-1,1,3,3-tetramethyluronium tetrafluoroborate (TBTU), N,N,N',N'-tetramethylchloroformamidinium-hexafluorophosphate (TCFH), N,N,N',N'-tetramethylfluoroformamidinium hexafluorophosphate (TFFH), 2-(endo-5-norbornene-2,3-dicarboxymido)-1,1,3,3-tetramethyluronium tetrafluoroborate (TNTU), S-(1-oxo-2-pyridyl)-thio-N,N,N',N'-tetramethyluronium tetrafluoroborate (TOTT), O-succinimidyl-1,3-dimethylpropyleneuronium tetrafluoroborate (TPD-OSu), S-(1-oxo-2-pyridyl)-thio-1,3-dimethylpropyleneuronium tetrafluoroborate (TPTDP), O-(1,2-dihydro-2-oxo-pyridyl]-N,N,N',N'-tetramethyluronium tetrafluoroborate (TPTU), or N,N,N',N'-tetramethyl-O-(succinimidyl)uronium tetrafluoroborate (TSTU), and combinations thereof. In some embodiments, the coupling agent is selected from the group consisting of HATU, SOCl₂, PyBOP, and combinations thereof. In some embodiments, the coupling agent is or includes HATU; in some embodiments, the coupling agent is or includes SOCl₂; in some embodiments, the coupling agent is or includes PyBOP; in some embodiments, the coupling agent is or includes (COCl)₂.

In certain embodiments, the coupling is performed in the presence of a suitable base. Such suitable bases are well known in the art and include organic bases, e.g., triethylamine, DIEA, pyridine, DABCO, and other non-nucleophilic basic nitrogen containing molecules. Other suitable bases include aqueous inorganic bases, such as NaOH, Na₂CO₃, NaHCO₃, KOH, K₂CO₃, KHCO₃, Na₃PO₄, K₃PO₄, NHOH, Ca(OH)₂, LiOH, or Li₂CO₃. Combinations of such bases may also be employed. In some embodiments, a base is selected from the group consisting of pyridine, TEA, NaHCO$_3$, DIEA, and combinations thereof (e.g., TEA/pyridine).

In certain embodiments, the coupling is performed in the presence of a suitable solvent or a solvent mixture that, in combination with the combined reacting partners and reagents, facilitates the progress of the reaction therebetween. A suitable solvent may solubilize one or more of the reaction components, or, alternatively, the suitable solvent may facilitate the suspension of one or more of the reaction components; see generally, Larock, R. C. Comprehensive Organic Transformation, A Guide to Functional Group Preparation, 2$^{nd}$ Edition, 1999, John Wiley & Sons (New York, N.Y.). Suitable solvents for use in the coupling step include ethers, halogenated hydrocarbons, aromatic solvents, polar aprotic solvents, or mixtures thereof. In certain embodiments, the solvent is or contains diethyl ether, dioxane, tetrahydrofuran (THF), dichloromethane (DCM), dichloroethane (DCE), chloroform, toluene, benzene, dimethylformamide (DMF), dimethylacetamide (DMA), dimethylsulfoxide (DMSO), N-methylpyrrolidinone (NMP), glyme and diglyme, or mixtures thereof. In certain embodiments, the coupling is performed in the presence of a a suitable solvent mixture. This mixture may include water and/or an organic solvent or a mixture of organic solvents.

In certain embodiments, the coupling step is conducted at temperatures between about −12° C. to about 90° C. In certain embodiments, the coupling step is conducted at about 0° C. to about 60° C. In certain embodiments, the coupling step is conducted at about 16° C. to about 28° C.

In certain embodiments, the coupling step, when conducted under Schotten-Bauman conditions, is conducted at a pH in the range of about 7.5 to about 10. In certain embodiments, the coupling step is conducted at a pH in the range of about 8.5 to about 9.5. In certain embodiments, the coupling step is conducted at a pH of about 9.

The above described methods, and others, are known to one of ordinary skill in the art, e.g., see "Advanced Organic Chemistry," Jerry March, 5$^{th}$ Ed., John Wiley and Sons, N.Y.

B. Preparation of Compounds by Extraction from Botanical Sources

The naturally occurring compounds of Formula I may be prepared from extracts obtained from a variety of botanical sources such as green coffee beans, roasted coffee beans, spent ground coffee beans, coffee wax (collectively "coffee"), coffee cherries (berries), chocolate, *withania somnifera* (fruit), Butcher's broom (root), coconut, *ginkgo biloba, bacopa monniera, nigella sativa*, St. John's wort, *annova atemoya* (seeds), and *scorodocarpus borneesis* (fruit). The compounds may be separated from the botanical source by any method known to those of ordinary skill in the art. Exemplary methods for extraction are described, for example, in US 2008/0213406, which is hereby incorporated by reference in its entirety.

For example, the compounds can be extracted from coffee by adding a solvent to coffee and agitating the resulting mixture, followed by removal of the solvent and collection of the residue containing the compounds. Any solvent in which the compounds are soluble may be used, including alcohols, such as ethanol, and chlorinated solvents, such as dichloromethane. In some embodiments, the agitation is performed by shaking the mixture for about 30 minutes to about 300 minutes. In other embodiments, the agitation is performed at a temperature ranging from about 20° C. to about the boiling point of the solvent.

Depending on the purity of the resulting residue, the residue is then loaded onto a column, eluted with a solvent, and the different fractions collected. The fraction containing the desired compound(s) may be further purified as necessary, such as by preparative HPLC, repeated column chromatography, or by extraction. This, and related methods known to those of skill in art allow for the separation of compounds from less desirable compounds also contained in the botanical source, such as free fatty acids, caffeine, caffeic acid, chlorogenic acid and other lipids. These methods also allow for the removal of compounds of Formula I where W is less than 15 or greater than 22. In some embodiments these less desirable compounds are present in amounts less than 20% by weight of the composition. As an alternative to column purification, one skilled in the art will recognize that the product can be purified by precipitation or crystallization.

In some aspects, naturally occurring compounds of formula I are prepared by extracting coffee wax. Coffee wax can be extracted in a solvent such as acetonitrile, hexane, ethyl acetate, petroleum ether, diethyl ether, ethanol, heptanes, benzene, toluene, diglyme, glyme, propyl acetate, butyl acetate, isopropanol, butanol, chlorphorm, dichloroethane or a combination thereof. In some embodiments, solvent extraction is carried out at elevated temperatures (e.g., at a temperature at or above 50° C., 55° C., or 60° C.). In some embodiments, solvent extraction is carried out under vacuum. Insoluble particulate material is removed by any available means (e.g., filtration). A fraction containing compounds is isolated from the extract, e.g., by precipitation and/or solvent evaporation. In some embodiments, an extract is cooled to precipitate impurities, or to precipitate the desired compounds. One of skill in the art is able to determine whether a given condition precipitates impurities or the desired compounds. Precipitated material containing compounds can be washed by further extraction, e.g., with one or more additional solvent extraction and precipitation steps, using the same solvents as used in the initial extraction, or using different solvents, optionally at elevated temperatures. Extracts enriched for compounds can be subjected to further purification and/or concentration steps, e.g., to enrich for a particular compound of interest.

In some embodiments, a coffee extraction method produces an extract comprising at least 2%, 3%, 4%, 5%, 10%, 20%, 30%, 40%, 50%, 60%, 70%, 80%, or 90% compound(s). In some embodiments, a coffee extraction method produces an extract comprising at least 2%, 3%, 4%, 5%, 10%, 20%, 30%, 40%, 50%, 60%, 70%, 80%, or 90% of a particular compound.

In one exemplary method, an extract is prepared from coffee wax as follows. Coffee wax is dissolved in acetonitrile and heated to 60° C. under vacuum. Insoluble material is removed and extraction of insoluble material is repeated. The soluble portions of the extraction are combined and cooled to 4° C. over 16 hours and filtered. The precipitate collected from the filtration is dissolved in hot acetonitrile at 60° C., cooled at 4° C. up to 16 hours and filtered. The solid phase is dissolved in hot ethanol at 70° C., cooled to room temperature, and incubated for 16 hours. The precipitate is recovered and is optionally subjected to further purification steps, e.g., to isolate a particular compound.

In another exemplary method, an extract is prepared from coffee wax by first dissolving the coffee wax in ethyl acetate and heating to 50° C. under vacuum. The extract is cooled at room temperature for one hour and filtered. Solid precipitate is discarded. The filtrate is evaporated to dryness and dissolved in hexane or petroleum ether at 50° C. and filtered.

Compounds provided herein can be recovered from the solid phase (e.g., at 60-80% purity) or from the liquid phase (e.g., at 15-40% purity).

IV. Compositions

In certain embodiments, the present invention provides compositions (in an appropriate form). Such compositions may be formulated as pharmaceutical and/or nutraceutical preparations. Compositions as described herein may be used in the treatment of one or more diseases, disorders, or conditions, for example, those associated with abnormal levels of PP2A methylation and/or PP2A phosphatase activity.

In general, one or more compounds of the present invention may be formulated into pharmaceutical and/or nutraceutical compositions by admixing a compound or extract containing a compound or extract, containing a compound, further fortified with the compound and/or extract of formula I with one or more additives (e.g., carriers, vehicles, binders, diluents, etc.) suitable for the selected route of administration.

In certain embodiments, compositions provided herein comprise at least one component of a botanical source that produces the compound, which botanical source is selected from the group consisting of green coffee beans, roasted coffee beans, spent ground coffee beans, coffee wax (collectively "coffee"), coffee cherries (berries), chocolate, *withania somnifera* (fruit), Butcher's broom (root), coconut, *ginkgo biloba, bacopa monniera, nigella sativa*, St. John's wort, *annova atemoya* (seeds), and *scorodocarpus borneesis* (fruit).

In certain embodiments, compositions provided herein are substantially free of caffeine, caffeic acid or chlorogenic acid. In certain embodiments, the composition contains less than about 10%, 9%, 8%, 7%, 6%, 5%, 4%, 3%, 2%, 1%, 0.5%, 0.4%, 0.3%, 0.2%, 0.1%, 0.01% or less of caffeine, caffeic acid, and/or chlorogenic acid.

In certain embodiments, the present invention provides compositions comprising a compound of formula I, Ia, Ib, Ic, Id, Ie, If, Ig and/or Ih, and one or more components of a natural source that produces the compound. In some such embodiments, the natural source is a botanical source, and the component is a component of the botanical source. In some embodiments, the botanical source is selected from the group consisting of green coffee beans, roasted coffee beans, spent ground coffee beans, coffee wax (collectively "coffee"), coffee cherries (berries), chocolate, *withania somnifera* (fruit), Butcher's broom (root), coconut, *ginkgo biloba, bacopa monniera, nigella sativa*, St. John's wort, *annova atemoya* (seeds), and *scorodocarpus borneesis* (fruit).

In certain embodiments, the present invention provides compositions comprising a compound of formula I, Ia, Ib, Ic, Id, Ie, If, Ig and/or Ih and one or more natural source components selected from the group consisting of naturally-occurring oils and lipids. In certain embodiments, the present invention provides compositions comprising a compound of formula I, Ia, Ib, Ic, Id, Ie, If, Ig and/or Ih, which composition either: (i) lacks one or more components that is found in a natural source that produces the compound; or (ii) contains a reduced concentration (with respect to concentration of compound) of such one or more natural source components than is found in the natural source when it produces the compound in nature. In certain embodiments, the reduced or missing component is selected from the group consisting of caffeine, sterols, caffeic acid, chlorogenic acid, residual pesticides, residual heavy metals and combinations thereof. That said, in certain embodiments, provided compositions do contain one or more of caffeine, sterols, caffeic acid, chlorogenic acid, residual pesticides, residual heavy metals and combinations thereof.

The amount of compound of formulae described herein added to a nutraceutical, pharmaceutical, or comestible is typically at least about 0.1 mg. In some embodiments, the compound is dosed at least once per day. In other embodiments, supplemental dosages can be administered after the initial dosage and can contain any additional amount of compound beyond the initial about 0.1 mg dose. In some embodiments, the nutraceutical, pharmaceutical or comestible contains at least 0.1 mg of the compound of formulae added to or fortified in an extract containing at least 0.1 mg of the compound.

In certain embodiments, the amount of compounds of formula I added to a nutraceutical, pharmaceutical, or comestible is typically at least about 8 mg. In some embodiments, the compound is dosed at least once per day. In other embodiments, supplemental dosages can be administered after the initial dosage and can contain any additional amount of compound beyond the initial about 8 mg dose. In some embodiments, the nutraceutical, pharmaceutical or comestible contains at least 8 mg of the compound of formulae added to or fortified in an extract containing at least 8 mg of the compound.

In some embodiments, the present invention provides a packaged nutraceutical, pharmaceutical, or comestible comprising at least about 0.1 mg of a compound of the formulae herein, where W ranges from about 15 to about 21, having an activity in the inhibition of methylesterase ($IC_{50}$) of less than about 100 µM. In certain embodiments the activity in the inhibition of methylesterase ($IC_{50}$) is less than about 90 µM. In certain embodiments the activity in the inhibition of methylesterase ($IC_{50}$) is less than about 80 µM. In certain embodiments the activity in the inhibition of methylesterase ($IC_{50}$) is less than about 70 µM. In certain embodiments the activity in the inhibition of methylesterase ($IC_{50}$) is less than about 60 µM. In certain embodiments the activity in the inhibition of methylesterase ($IC_{50}$) is less than about 50 µM. In certain embodiments the activity in the inhibition of methylesterase ($IC_{50}$) is less than about 40 µM. In certain embodiments the activity in the inhibition of methylesterase ($IC_{50}$) is less than about 30 µM. In certain embodiments the activity in the inhibition of methylesterase ($IC_{50}$) is less than about 20 µM. In certain embodiments the activity in the inhibition of methylesterase ($IC_{50}$) is less than about 10 µM. In certain embodiments the activity in the inhibition of methylesterase ($IC_{50}$) is less than about 5 µM.

In some embodiments, the present invention provides a packaged nutraceutical, pharmaceutical, or comestible comprising at least about 8 mg of a compound of the formulae herein, where W ranges from about 15 to about 21, having an activity in the inhibition of methylesterase ($IC_{50}$) of less than about 100 µM. In certain embodiments the activity in the inhibition of methylesterase ($IC_{50}$) is less than about 90 µM. In certain embodiments the activity in the inhibition of methylesterase ($IC_{50}$) is less than about 80 µM. In certain embodiments the activity in the inhibition of methylesterase ($IC_{50}$) is less than about 70 µM. In certain embodiments the activity in the inhibition of methylesterase ($IC_{50}$) is less than about 60 µM. In certain embodiments the activity in the inhibition of methylesterase ($IC_{50}$) is less than about 50 µM. In certain embodiments the activity in the inhibition of methylesterase ($IC_{50}$) is less than about 40 µM. In certain embodiments the activity in the inhibition of methylesterase ($IC_{50}$) is less than about 30 µM. In certain embodiments the activity in the inhibition of methylesterase ($IC_{50}$) is less than about 20 µM. In certain embodiments the activity in the inhibition of methylesterase ($IC_{50}$) is less than about 10 µM. In certain embodiments the activity in the inhibition of methylesterase ($IC_{50}$) is less than about 5 µM.

In some embodiments, the present invention provides a packaged nutraceutical, pharmaceutical, or comestible comprising at least about 0.1 mg of a compound of the formulae herein, where W ranges from about 15 to about 21, having an activity in the inhibition of methyltransferase ($IC_{50}$) of less than about 100 µM, an additive, and instructions for use thereof. In certain embodiments the activity in the inhibition of methyltransferase ($IC_{50}$) is less than about 90 µM. In certain embodiments the activity in the inhibition of methyltransferase ($IC_{50}$) is less than about 80 µM. In certain embodiments the activity in the inhibition of methyltransferase ($IC_{50}$) is less than about 70 µM. In certain embodiments the activity in the inhibition of methyltransferase ($IC_{50}$) is less than about 60 µM. In certain embodiments the activity in the inhibition of methyltransferase ($IC_{50}$) is less than 50 µM. In certain embodiments the activity in the inhibition of methyltransferase ($IC_{50}$) is less than about 40 µM. In certain embodiments the activity in the inhibition of methyltransferase ($IC_{50}$) is less than about 30 µM. In certain embodiments the activity in the inhibition of methyltransferase ($IC_{50}$) is less than about 20 µM. In certain embodiments the activity in the inhibition of methyltransferase ($IC_{50}$) is less than about 10 µM. In certain embodiments the activity in the inhibition of methyltransferase ($IC_{50}$) is less than about 5 µM.

In some embodiments, the present invention provides a packaged nutraceutical, pharmaceutical, or comestible comprising at least about 8 mg of a compound of the formulae herein, where W ranges from about 15 to about 21, having an activity in the inhibition of methyltransferase ($IC_{50}$) of less than about 100 µM, an additive, and instructions for use thereof. In certain embodiments the activity in the inhibition of methyltransferase ($IC_{50}$) is less than about 90 µM. In certain embodiments the activity in the inhibition of methyltransferase ($IC_{50}$) is less than about 80 µM. In certain embodiments the activity in the inhibition of methyltransferase ($IC_{50}$) is less than about 70 µM. In certain embodiments the activity in the inhibition of methyltransferase ($IC_{50}$) is less than about 60 µM. In certain embodiments the activity in the inhibition of methyltransferase ($IC_{50}$) is less than about 50 µM. In certain embodiments the activity in the inhibition of methyltransferase ($IC_{50}$) is less than about 40 µM. In certain embodiments the activity in the inhibition of methyltransferase ($IC_{50}$) is less than about 30 µM. In certain embodiments the activity in the inhibition of methyltransferase ($IC_{50}$) is less than about 20 µM. In certain embodiments the activity in the inhibition of methyltransferase ($IC_{50}$) is less than about 10 µM. In certain embodiments the activity in the inhibition of methyltransferase ($IC_{50}$) is less than about 5 µM.

Any additive may be used provided that they do not destabilize the compositions. Without wishing to be bound by any particular theory, it is believed that strong bases, effervescent disintegrants, and oxidants should be kept to a minimum in any formulation or composition to avoid destabilization.

Suitable additives include, but are not limited to, dietary suitable starch, vegetable oil, vegetable gums, gelatins, soy extracts, sugars, grains, natural and artificial flavorings, and the like. Other suitable additives include water, salt solutions, alcohol, vegetable oils, polyethylene glycols, gelatin, lactose, amylose, magnesium stearate, talc, silicic acid, viscous paraffin, perfume oil; fatty acid monoglycerides and diglycerides, petroethral fatty acid esters, hydroxymethylcellulose, polyvinylpyrrolidone, and the like. Yet other suitable additives include Cremaphor, Tween, and cyclodextrin. Further additives or carriers are described in detail in *Remington's Pharmaceutical Sciences*, Twentieth Edition, ©02000, incorporated herein by reference.

Of course, the additive selected, and the amount of additive needed, depend on the route of administration and vehicle chosen for delivery. In some embodiments, the additive is formulated with the compound as a unit-dose formulation. For example, a tablet may contain from about 0.5% to about 95% by weight of a compound of formula I and from about 5% to about 99.5% of an additive. Those skilled in the art will be able to select an appropriate amount of additive depending on the amount of compound and route of administration.

A dosage form may include other conventional excipients in generally known amounts. In some embodiments, these excipients supplement, or depending on their properties, replace the additives mentioned above, and thus can act as carriers or vehicles themselves for the compositions. These may include binders, sweeteners, coloring components, flavors, glidants, lubricants, preservatives, fillers, noneffervescent disintegrants, stabilizers, wetting agents, emulsifiers, and salts for influencing osmotic pressure. Of course, other auxiliary ingredients may be added to any formulation, including colorings, flavoring and/or aromatic substances.

Examples of excipients include the following: Fillers include sugar and sugar alcohols and these may include nondirect compression and direct compression fillers. Nondirect compression fillers generally, at least when formulated, have flow and/or compression characteristics which make them impractical for use in high speed tableting process without augmentation or adjustment. For example, a formulation may not flow sufficiently well and therefore, a glidant such as, for example, silicon dioxide may need to be added.

Direct compression fillers, by contrast, do not require similar allowances. They generally have compressibility and flowability characteristics which allow them to be used directly. It is noted that, depending upon the method by which formulations are made, nondirect compression fillers may be imparted with the properties of direct compression fillers. The reverse is also true. As a general matter, non direct compression fillers tend to have a relatively smaller particle size when compared to direct compression fillers. However, certain fillers such as spray dried mannitol have relatively smaller particle sizes and yet are often directly compressible, depending upon how they are further processed. There are also relatively large nondirect compression fillers as well.

Suitable fillers include mannitol, lactose, sorbitol, dextrose, sucrose, xylitol and glucose. Noneffervescent disintegrants may also be used in accordance with the present invention. These may also include binders that have disintegrating properties. Disintegrants in accordance with the present invention can include microcrystalline cellulose, cross linked polyvinyl pyrrolidone (PVP XL), sodium starch glycolate, croscarmellose dosium, cross-lined hydroxypropyl cellulose and the like.

The compositions of the present invention may be formulated as aqueous suspensions wherein a compound of formula I is in admixture with excipients, additives and/or suitable for the manufacture of aqueous suspensions. Such additives and/or excipients are suspending agents, for example, sodium carboxymethylcellulose, methylcellulose, hydroxy-propylmethylcellulose, sodium alginate, polyvinylpyrrolidone, gum tragacanth, and gum acacia; dispersing or wetting agents may be a naturally-occurring phosphatide such as lecithin, or condensation products of an alkylene oxide with fatty acids, for example, polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions also may contain one or more coloring agents, one or more flavoring agents, and one or more sweetening agents, such as sucrose or saccharin.

Compositions of the present invention may be formulated as oily suspensions by suspending a compound of formula I in a vegetable oil, for example arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral composition. These compositions may be preserved by the addition of an antioxidant such as ascorbic acid.

Compositions of the present invention may be formulated in the form of dispersible powders and granules suitable for composition of an aqueous suspension by the addition of water. Compounds of formula I in such powders and granules is provided in admixture with a dispersing or wetting agent, suspending agent, and one or more preservatives. Suitable dispersing or wetting agents and suspending agents are exemplified by those already mentioned above. Additional excipients or example, sweetening, flavoring and coloring agents also may be present.

Compositions of the invention also may be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example, gum acacia or gum tragacanth, naturally occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate. The emulsions also may contain sweetening and flavoring agents.

Compositions of the invention also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

The compositions and compounds of the present invention may be added to traditional pharmaceutical or nutraceutical dosage forms or may be combined with comestibles.

One aspect of the present invention is a dosage form containing at least about 0.1 mg of a fatty-acid conjugated compound of formula I, where W is between about 15 and about 22 carbons, having an activity in the inhibition of methylesterase of less than about 50 µM, and an additive.

One aspect of the present invention is a dosage form containing at least about 8 mg of a fatty-acid conjugated compound of formula I, where W is between about 15 and about 22 carbons, having an activity in the inhibition of methylesterase of less than about 50 µM, and an additive.

In some embodiments, the dosage form is administered as a pharmaceutical or neutraceutical. In other embodiments, the dosage forms are added to foods, beverages, or other comestibles.

In certain embodiments, the present invention provides a nutraceutical, pharmaceutical, or comestible formulation comprising: an active ingredient, at least one solubilizing and/or thickening agent, at least one solvent, and a diluent.

In certain embodiments, the active ingredient is a compound of formula I, Ia, Ib, Ic, Id, Ie, If, Ig, or Ih. In certain embodiments, the active ingredient in the formulation is compound I-63. In certain embodiments, the active ingredient is present in the formulation in an amount of about 0.5% (wt %). In certain embodiments, the active ingredient is present in the formulation in an amount of about 5% (wt %). In certain embodiments, the active ingredient is present in the formulation in an amount of about 10% (wt %). In certain embodiments, the active ingredient is present in the formulation in an amount of about 25% (wt %). In certain embodiments, the active ingredient is present in the formulation in an amount of about 50% (wt %).

In certain embodiments, the formulation comprises at least one solubilizing agent and/or thickening agent. In certain embodiments, the solubilizing agent and/or thickening agent is a fatty acid ethyl ester. In certain embodiments, the solubilizing agent and/or thickening agent is ethyl oleate. In certain embodiments, the solubilizing agent and/or thickening agent is Solutol-HS15 (i.e., polyethylene glycol 660 hydroxy stearate). In certain embodiments, the solubilizing agent and/or thickening agent is a surfactant. In certain embodiments, the surfactant is non-ionic. In certain embodiments, the solubilizing agent and/or thickening agent is Tween-80 or Polysorbate 80. In certain embodiments, the solubilizing agent and/or thickening agent is present in an amount of about 20-30% (wt %). In certain embodiments, the solubilizing agent and/or thickening agent is present in an amount of about 0-7% (wt %). In certain embodiments, the solubilizing agent and/or thickening agent is present in an amount of about 0-1% (wt %).

In certain embodiments, the formulation comprises at least one solvent. In certain embodiments, the solvent is a polar, organic solvent. In certain embodiments, the solvent is an alcohol. Exemplary alcohols include isopropanol, SDA-3A alcohol, or ethanol. In certain embodiments, the solvent is present in an amount of from about 0 to 5% (wt %). In certain embodiments, the solvent is present in an amount of from about 0 to 1% (wt %).

In certain embodiments, the formulation comprises at least one diluent. In certain embodiments, the diluent is phosphate buffered saline (PBS). In certain embodiments, the PBS is present in an amount of from about 20%-50% (wt %). In certain embodiments, the PBS is present in an amount of from about 40% (wt %).

In certain embodiments, the formulation has a pH range of from about 2.0-9.0. In certain embodiments, the pH is from 3.0-5.0. In certain embodiments, the pH is 4.9.

Other ingredients which may be desirable to use in the preparations of provided compositions include preservatives, co-solvents and viscosity building agents, additives, excipients, fillers, organometallic modifiers, coloring and masking agents One skilled in the art will readily appreciate that the category under which a particular component of a formulation is listed is not intended to be limiting. In some cases, a particular component might appropriately fit in more than one category. Also, as will be appreciated by one skilled in the art, the same component can sometimes perform different functions, or can perform more than one function, in the context of a particular formulation for example, depending upon the amount of the ingredient and/or the presence of other ingredients and/or active compound(s). Exemplary categories of components used herein include, but are not limited to, solubilizing agent, thickening agent, preservatives, co-solvents, viscosity building agents, additives, excipients, fillers, etc.

Daily Dose Amounts

The therapeutically effective dose of any specific compounds of the formulae described herein will vary from compound to compound, subject to subject, and upon the route of delivery, as well as the final formulation. In some embodiments, to be therapeutically effective, 0.1 mg of one or more compounds of the formulae described herein must be administered daily. In some embodiments, to be therapeutically effective, 0.1 mg of one or more compounds of the formulae described herein must be administered daily. In certain embodiments, at least about 12 mg of a compound of the formulae described herein can be administered daily. In certain embodiments, at least about 8 mg of at least one compound of the formulae described herein can be administered daily. In yet other embodiments, at least about 20 mg of at least one compound of the formulae described herein can be administered daily. In yet further embodiments, at least about 50 mg of at least one compound of the formulae described herein can be administered daily. In yet even further embodiments, at least about 100 mg of at least one compound of the formulae described herein can be administered daily.

Additional doses beyond about a 0.1 mg dose may be given throughout the day. These supplemental doses may contain any amount of the compounds of Formula I. In some embodiments, the supplemental doses include at least an additional 0.1 mg of at least one compound of the formulae described herein. In some embodiments, the supplemental doses include at least an additional 8 mg of at least one compound of the formulae described herein. In some embodiments, the supplemental doses include at least an additional 0.1 mg of at least one compound of the formulae described herein. In some embodiments, the supplemental doses include at least an additional 8 mg of at least one compound of the formulae described herein. In other embodiments, the supplemental dosages include at least an additional 12 mg of at least one compound of the formulae described herein. In yet other embodiments, the supplemental dosages include at least an additional about 20 mg of at least one compound of the formulae described herein.

Accordingly, any dosage form (whether a nutraceutical, pharmaceutical, comestible, or an extract) which is administered only once daily should contain at least 0.1 mg of a compound of the formulae described herein. In certain embodiments, any dosage form (whether a nutraceutical, pharmaceutical, comestible, or an extract) which is administered only once daily should contain at least 8 mg of a compound of the formulae described herein. Of course, it is entirely acceptable for multiple doses to be administered.

In some embodiments, the subject is dosed two or more times per day. In some embodiments, the subject is provided a daily dose of 0.1 mg/day, 8 mg/day, 12 mg/day, 10 mg/day, 12 mg/day 20 mg/day, 24 mg/day, 50 mg/day, and 100 mg/day of one or more of the compounds of the formulae described herein.

While there is believed to be no upper limit in the amount of a compound of the formulae described herein which may be administered, as with any substance taken into the body, subjects should avoid dosage levels which could result in toxicity.

Delivery

The compounds of formula I, their salts, acid derivatives and/or mixtures thereof are useful as nutraceuticals or as pharmaceutically active agents and may be utilized in bulk form or may be formulated into nutraceutical or pharmaceutical compositions for administration. For example, compositions comprising at least one compound of formula I can be administered as conventional pharmaceuticals or as nutraceutical compositions, including dietary supplements.

Alternatively, the bulk extracts of formula I may be added to foods or beverages and, thus administered as part of a comestible product. Alternatively, compounds of formula I may be synthesized or purchased from a commercial source, provided they have the structure of formula I and are naturally occurring.

Oral Dosage Forms

In general, compositions comprising a therapeutically or pharmaceutically effective amount of a compound of formula I may be formulated for administration in unit dosage forms.

In some embodiments, the dosage form is administered by any route including oral, buccal, parenteral, transdermal, tranmucosal, or inhalation.

Compositions provided herein may be in a form suitable for oral use, for example, as tablets, troches, lozenges, pills, aqueous or oily suspensions, solutions, dispersible powders or granules, emulsions, hard or soft capsules, syrups or elixirs, pastes, gels or the like.

Compounds intended for oral use may be prepared according to any known method, and such compositions may contain one or more excipients selected from the group consisting of sweetening agents, flavoring agents, coloring agents, and preserving agents in order to provide pharmaceutically elegant and palatable compositions. In general, the formulations for oral administration are prepared by uniformly and intimately admixing the active compound with a liquid or finely divided solid excipient, or both, and then, if necessary, shaping the resulting mixture.

Tablets may contain the active ingredient(s) in admixture with non-toxic pharmaceutically acceptable additives and/or excipients which are suitable for the manufacture of tablets. These additives or excipients may be, for example, fillers, wetting agents, inert diluents, such as calcium carbonate, sodium carbonate, lactose, calcium phosphate or sodium phosphate; granulating effervescent disintegrating agents (e.g., effervescent tablets) and noneffervescent disintegrating agents, for example, corn starch or alginic acid; binding agents, for example, starch, gelatin or acacia; and lubricating agents, for example, magnesium stearate, stearic acid or talc.

Tablets may be prepared by traditional methods such as by compressing or molding a powder or granules containing the compound. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They also may be coated for controlled delivery. For example, a "delayed release" dosage form releases a product or substance at a time other than promptly after administration. Examples of delayed-release systems include repeat-action tablets and capsules, and enteric-coated tablets where timed release is achieved by a barrier coating.

Compositions of the present invention also may be formulated for oral use as hard gelatin capsules, where the compounds of formula I are mixed with an inert solid diluent, for example, calcium carbonate, calcium phosphate or kaolin, or soft gelatin capsules wherein the active ingredient(s) is (are) mixed with water or an oil medium, for example, peanut oil, liquid paraffin, or olive oil.

In another embodiment, liquid preparations for oral administration can also be used. Liquid preparations can be in the form of solutions, syrups or suspensions, or a dry product for reconstitution with water or another suitable vehicle before use. Such liquid preparations can be prepared by conventional means with pharmaceutically acceptable additives such as suspending agents, emulsifying agents, non-aqueous vehicles, and preservatives.

Liquid based oral dosage forms, like their solid counterparts, must contain at least 0.1 mg of a compound of formula I. In certain embodiments, the liquid based oral dosage forms, like their solid counterparts, must contain at least 8 mg of a compound of formula I. One skilled in the art will be able to properly formulate a liquid formulation containing an appropriate amount of a compound of formula I per fluidic ounce, depending on the additive or carrier selected.

Rectal and/or Vaginal Administration

Alternatively, or additionally, the pharmaceutical compositions provided herein may be administered in the form of suppositories for rectal and/or vaginal administration. These may be prepared by mixing the agent with a suitable non-irritating excipient which is solid at room temperature but liquid at rectal and/or vaginal temperature and therefore will melt in the rectum and/or vagina to release the drug. Such materials include cocoa butter, beeswax and polyethylene glycols.

Buccal Administration

Formulations suitable for buccal administration include tablets and lozenges comprising a compound of formula I in a flavored base, such as sucrose, acacia or tragacanth; and pastilles comprising the compound in an inert base, such as gelatin and glycerin or sucrose and acacia.

Topical Administration

Formulations of the present invention suitable for topical application to the skin take the form of an ointment, cream, lotion, paste, gel, spray, aerosol, or oil. Additives which may be used include vaseline, lanoline, polyethylene glycols, alcohols, transdermal enhancers, and combinations of two or more thereof.

Formulations suitable for transdermal administration may also be presented as medicated bandages or discrete patches adapted to remain in intimate contact with the epidermis of the recipient for a prolonged period of time. Formulations suitable for transdermal administration may also be delivered by iontophoresis (passage of a small electric current C15 mA) to "inject" electrically charged ions into the skin) through the skin. For this, the dosage form typically takes the form of an optionally buffered aqueous solution of the active compound.

Inhalable Dosage Forms

For administration by inhalation, compositions for use in the present invention can be delivered in the form of an aerosol spray in a pressurized package or as a nebulizer, with use of suitable propellants and/or pellets. In the case of a pressurized aerosol, the dosage unit can be determined by providing a valve to deliver a metered dose in accordance with the invention.

Parenteral Administration

Parenterally administered compositions are formulated to allow for injection, either as a bolus or as a continuous infusion. For parenteral application, "parenteral" meaning subcutaneous injections, intravenous, intramuscular, intrasternal injection, or infusion techniques, particularly suitable vehicles consist of solutions, preferably oily or aqueous solutions, as well as suspensions, emulsions, or implants. Formulations for injection can be prepared in unit dosage forms, such as ampules, or in multi-dose units, with added preservatives. The compositions for injection can be in the form of suspensions, solutions, or emulsions, containing either oily or aqueous additives. They may also contain formulatory agents such as suspending agents, stabilizing agents, and/or dispersing agents. Compounds of the present invention may also be presented in powder form for reconstitution with a suitable vehicle before use.

Compositions of the present invention also may be in the form of a sterile injectable aqueous or oleaginous suspension. Injectable compositions, such as sterile injectable aqueous or oleaginous suspensions, may be formulated according to the known art using suitable dispersing or wetting agents and suspending agents. The sterile injectable composition may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In some embodiments, formulations of the present invention suitable for parenteral administration conveniently comprise sterile aqueous preparations of the active compound, which preparations are preferably isotonic with the blood of the intended recipient. Such preparations may conveniently be prepared by admixing the active compound with water or a glycine buffer and rendering the resulting solution sterile and isotonic with the blood.

In addition, sterile, fixed oils are conventionally employed as a solvent or suspending medium. Aqueous suspensions may contain substances which increase the viscosity of the suspension and include, for example, sodium carboxymethyl cellulose, sorbitol and/or dextran. Optionally, the suspension may also contain stabilizers.

Alternately, compounds of formula I be added to a parenteral lipid solution.

Comestibles

The compounds and compositions containing a compounds of formula I may also be formulated as or with comestibles. The comestibles of the invention include water, flavored water, fruit-based drinks, coffee-based drinks (caffeinated or decaffeinated), tea-based drinks, sport drinks, nutrition bars, snack foods, gums, cereals, candies, baby formulas, energy drinks, adult nutritional drinks, health drinks, spirits, fruit juices, carbonated beverages, and other food products. The term "sports drink" refers to a beverage that is supposed to rehydrate athletes, as well as restoring electrolytes, sugar and other nutrients, for example, Gatorade®, POWERade®, and All Sport®. As used herein, the term "energy drink" refers to a beverage, including, but not limited to, Jolt Cola®, Red Bull® and similar products, that contains legal stimulants, electrolytes, vitamins and minerals; these products are formulated to give the user a burst of energy. The term "adult nutritional drink" as used herein refers to such products as Ensure®, Longetics® or a similar product. The term "health drink" refers to any beverage purported to have beneficial health effects, including, but not limited to, reducing inflammation, supporting the immune system, neutralizing infectious agents, preventing clogged arteries, preserving cognitive function and inhibiting cancer growth. The comestibles may also include additional ingredients that confer cognitive or other health benefits. In the case of beverages, the comestibles can be used in powder form which can be dissolved in a liquid suitable for human consumption.

Adding a compound of formula I to decaffinated coffee, tea or other decaffeinated products is especially appealing. It is believed that the decaffeination process not only strips caffeine out of the coffee, but also removes or reduces the amount of certain compounds of formula I. In that case, in order to attain the health benefits presumably attributed to certain coffees, it is necessary to add back in those compounds of formula I which were removed or whose concentrations were reduced.

The compounds of formula I can also be combined with ordinary foods. For example, the compositions can be mixed with soft drinks, food supplements, candy, cereal, breakfast bars, high-energy bars, and virtually any other food that can be supplemented with a powder, granules, or liquid. Thus, the invention specifically includes food substances of specific types combined with the composition of the invention in specified forms and quantities. The comestibles can either be a meal replacement or a snack between meals.

Moreover, compounds of formula I can be administered either alone or in combination with other phytochemicals, as dietary supplements, known to affect anxiety. The dietary supplements can be in the form of a solid bar, a paste, a gel, a tablet, a capsule, or a liquid. Examples of other phytochemicals which can be used in combination with compounds described herein include, but are not limited to, resveratrol and its hydroxylated and methoxylated analogs, rosemary extract, green tea extracts, orange peel extracts, Mexican Bamboo, and Huzhang extracts. Compounds of formula I can also be combined with vitamins (e.g. Vitamin E) and minerals. In addition, compounds of formula I may be administered as part of a multi-vitamin or other herbal formula or remedy.

Various methods are known to those skilled in the art for addition or incorporation of nutraceuticals or extracts into foods or beverages. In some embodiments, the compounds described herein may be added by the subject to any food or beverage as a dietary supplement. For example, a subject would add a predetermined therapeutically effective dosage of a compound of formula I, preferably pre-packaged, to a food or beverage, such as by sprinkling the compound onto the food or mixing the extract with a beverage. In other embodiments, a compound of formula I may be precombined with a food or beverage (e.g. a dairy or non dairy creamer may contain the extract). In yet other embodiments, a compound of formula I may be prepackaged as part of, or instead of, a sweetener (e.g. a sugar packet containing a teaspoon of sugar and 0.1 mg, or 8 mg, of a compound of formula I). In yet further embodiments, a therapeutically effective dosage of a compound may be pre-combined with ground coffee (caffeinated or decaffeinated) instant coffee or tea. For example, packets of the compound can be provided to be sprinkled in drinks or foods such that it does not affect taste. A compound of formula I may also be added to spices, such as cinnamon.

IV. Package

In another aspect of the invention is a package containing at least 0.1 mg of a compound or composition of formula I, an additive, and instructions for use. In certain embodiments, the invention is a package containing at least 8 mg of a compound or composition of formula I, an additive, and instructions for use. A compound or composition of formula I contained in the package will contain a suitable additive such that the contents of the package could be added to a comestible. Instructions will provide information on how to add the package contents to the comestible. For example, the package may provide instructions that 1 mg of a composition of formula I, should be added per fluidic ounce of a beverage. The instructions may further provide dosage information, such as the amount of a composition that should be administered daily. For example, the instructions may provide that at least two packets containing a composition of formula I should be consumed daily.

V. Uses

In certain embodiments, the present invention provides synthetic and/or naturally occurring fatty-acid conjugated compounds which may themselves be added to or combined with pharmaceuticals, nutraceuticals, or other comestibles to treat, prevent, control or ameliorate diabetes, insulin resistance, and metabolic syndrome. In some embodiments, the present invention provides synthetic and/or naturally occurring fatty-acid conjugated compounds which may themselves be added to or combined with pharmaceuticals, nutraceuticals, or other comestibles to treat, prevent, control or ameliorate neurodegenerative diseases, such as proteinopathies. Exemplary proteinopathies include tauopathies and synucleopathies. In certain embodiments, tauopathies include Alzheimer's Disease, neurodegeneration in adult cases of Down's syndrome, Dementia pugilistica, Pick's Disease, Guam parkinsonism dementia complex, Fronto-temporal dementia, Cortico-basal degeneration, Pallido-pontal-nigral degeneration, and Progressive supranuclear palsy. In certain embodiments, synucleinopathies (e.g., alpha-synucleinopathies), include Parkinson's Disease, Dementia with Lewy bodies (DLB), and multiple system atrophy (MSA).

In certain embodiments, compounds which may themselves be added to or combined with pharmaceuticals, nutraceuticals, or other comestibles to treat, prevent, control or ameliorate neurological disorders, neurodegenerative diseases, diabetes, and/or metabolic syndrome. In certain embodiments, the metabolic syndrome disorder is selected from hyperglycemia, reduced insulin production, reduced insulin secretion and insulin resistance. In certain embodiments, the neurodegenerative disease is Parkinson's disease or Alzheimer's disease.

In certain embodiments the present invention provides compounds, compositions, extracts and/or methods of their preparation or use in the treatment of, for example certain neurodegenerative diseases (e.g., Alzheimer's disease and/or Parkinson's disease), diabetes, insulin resistance, and metabolic syndrome.

In certain particular embodiments, the present invention provides compounds, compositions, extracts in the treatment of, or amelioration of symptoms in, for example certain neurodegenerative diseases (e.g., Alzheimer's disease and/or Parkinson's disease), diabetes and metabolic disorders. Although not wishing to be bound by theory, it is believed these compounds, compositions, extracts as described herein are useful for modulating the activity of PP2A for the treatment of or amelioration of symptoms in neurodegenerative diseases such as Alzheimer's disease and/or Parkinson's disease, and in diabetes and/or metabolic disorders.

In another aspect, the present invention provides methods of sustaining PP2A levels in a subject by administering at least 0.1 mg of a compound and/or extract of formula I. In another aspect, the present invention provides methods of sustaining PP2A levels in a subject by administering at least 8 mg of a compound and/or extract of formula I. In another aspect, the present invention provides methods of modulating PP2A activity in a subject by administering at least 0.1 mg of a compound and/or extract of formula I. In another aspect, the present invention provides methods of modulating PP2A activity in a subject by administering at least 8 mg of a compound and/or extract of formula I. It is believed that such an administration will allow a subject to: (a) maintain current PP2A levels without further loss of PP2A levels and/or activity; (b) restore at least partial PP2A levels and/or activity; and/or (c) completely restore PP2A levels and/or activity compared to those found in normal healthy subjects.

Specific examples of certain particular diseases, disorders or conditions that may be treated with compounds of formula I, Ia, Ib, Ic, Id, Ie, If, Ig and/or Ih in accordance with the present invention are addressed individually below.

Tauopathies

Tauopathies constitute a family of neurodegenerative disorders characterized by a progressive loss of neuronal structural integrity. In tauopathies such as Fronto-temporal dementia and Progressive supranuclear palsy, mutations in the microtubule associated protein, tau, contribute to its abnormal hyperphosphorylation, aggregation and subsequent neuronal dysfunction. As described herein, one such tauopathy of particular interest, inter alia, is Alzheimer's Disease. Age-related abnormal tau hyperphosphorylation is recognized as a major causative factor of the dementia associated with Alzheimer's disease.

By 2050, the worldwide incidence of Alzheimer's disease is believed to quadruple from the estimated 26.6 million reported cases in 2006 (see Brookmeyer R., Johnson E., Ziegler-Graham K., Arrighi M. H. Forecasting the Global Burden of Alzheimer's Disease. *Alzheimer's and Dementia* 2007; 3 (3): 186-91). While a significant proportion of Alzheimer's Disease intervention research to date has been directed towards targeting β-amyloidosis, only recently, has the focus on much neglected neurofibrillary degeneration, which is another major histopathology in Alzheimer's Disease, brought microtubule associated protein tau to the forefront of drug discovery research in neurodegeneration (see Marx J., "Alzheimer's Disease: A New Take on Tau", *Science* 2007: Vol. 316. no. 5830, pp. 1416-1417; Roder H. M., Hutton M. L., Microtubule-associated Protein Tau as a Therapeutic Target in Neurodegenerative Disease. Expert Opin. Ther. Targets 2007; 11(4): 435-442; and Mazanetz M., Fisher P. M., "Untangling Tau Hyperphosphorylation in Drug Design for Neurodegenerative Diseases", Nature 2007; 6: 464-479).

Hyperphosphorylation of tau protein leads to its aggregation and formation of neurofibrillary tangles (NFT), subsequently leading to microtubules disruption and ultimately, neurodegeneration not only in Alzheimer's Disease, but also in Pick's disease, progressive supranuclear palsy (PSP) and corticobasal degeneration (CBD) (see Alonso A. D., Zaidi T., Grundke-Iqbal I., Iqbal K., Role of Abnormally Phosphorylated Tau in the Breakdown of Microtubules in Alzheimer's Disease, Proc Natl Acad Sci USA 1994; 91: 5562-6; Li B., Chohan M. O., Grundke-Iqbal I., Iqbal K., Disruption of Microtubule Network by Alzheimer Abnormally Hyperphosphorylated Tau. Acta Neuropathol. 2007; 113: 501-11; Hutton, M. et al., *Association of Missense and 5'-Splice Site Mutations in Tau with the Inherited Dementia FTDP-17, Nature* 393, 702-705 (1998); Dumanchin, C. et al., Segregation of a Missense Mutation in the Microtubule—associated Protein Tau Gene with Familial Frontotemporal Dementia and Parkinsonism. *Hum. Mol. Genet.* 7, 1825-1829 (1998); and Rizzu, P. et al., High Prevalence of Mutations in the Microtubule-associated Protein Tau in a Population Study of Frontotemporal Dementia in the Netherlands. *Am. J. Hum. Genet.* 64, 414-421 (1999). Tau-mediated neurodegeneration is also linked to specific mutations in the human gene (MAPT) causing frontotemporal dementia and Parkinsonism of chromosome 17 (FTDP-17).

Protein phosphatase-2A (PP2A) is the major phosphatase acting to reduce hyperphosphorylated tau, and in AD brains, PP2A is significantly downregulated (see Gong C. X., Shaikh S., Wang J. Z., Zaidi T., Grundke-Iqbal I., Iqbal K., Phosphatase Activity Toward Abnormally Phosphorylated Tau: Decrease in Alzheimer's Disease Brain, J. Neurochem 1995; 65: 732-738; and Vogelsberg-Ragaglia V., Schuk T., Trojanowski J. Q., Lee V. M., PP2a mRNA Expression is Quantitatively Decreased in Alzheimer's Disease Hippocampus, Exp. Neurol. 2001; 168: 402-412).

More specifically, post-mortem analyses of affected regions of the brains of Alzheimer's Disease-afflicted individuals, particularly the frontal and temporal regions, show significant deficiency in levels of $AB_\alpha C$ (i.e., the major form of PP2A that dephosphorylates p-tau) (see Sontag E., Luangpirom A., Hladik C., Mudrak I., Ogris E., Speciale S., White C. L., 3rd (2004b), Altered Expression Levels of the Protein Phosphatase 2A ABalphaC enzyme are Associated with Alzheimer's Disease Pathology, *J. Neuropathol. Exp. Neurol.*, 63(4): 287-301). Posttranslational modification of PP2A by reversible methylation at carboxy-terminal Leu309 greatly increases the affinity of $B_\alpha$ for AC dimers (see Tolstykh T., Lee J., Vafai S., Stock J. B. (2000), Carboxyl Methylation Regulates Phosphoprotein Phosphatase 2A by Controlling the Association of Regulatory B subunits, *Embo. J.,* 19 (21): 5682-5691) and regulates the assembly of $AB_\alpha C$ heterotrimers, the key prerequisite for healthy tau phosphorylation levels (see Vafai S. B., Stock J. B., 2002, "Protein Phosphatase 2A Methylation: A Link Between Elevated Plasma Homocysteine and Alzheimer's Disease", *FEBS Lett* 518 (1-3): 1-4).

PP2A methylation is regulated by a fine balance of two activities: (1) methylation activity of the protein phosphatase 2A methyltransferase (PPMT), which results in the increase of PP2A methylation; and (2) the demethylation activity of the protein phosphatase 2A methylesterase (PPME), which results in a decrease of PP2A methylation. The present invention encompasses a class of compounds, compositions and/or extracts of Formula I or a comestible containing such an extract that modulate PP2A activity towards phospho-tau by selectively targeting PPME and PPMT activities.

In certain embodiments, the present invention provides methods of treating ameloriating, controlling, or preventing neurodegenerative diseases such as Alzheimer's disease and other tauopathies by administering a compound, composition and/or extract of Formula I or a comestible containing such an extract, provided that at least 0.1 mg of the extract is administered. In certain embodiments, the present invention provides methods of treating ameloriating, controlling, or preventing neurodegenerative diseases such as Alzheimer's disease and other tauopathies by administering a compound, composition and/or extract of Formula I or a comestible containing such an extract, provided that at least 8 mg of the extract is administered.

According to one aspect, the present invention provides methods of treating, ameliorating, controlling, or preventing neurodegenerative diseases such as Alzheimer's disease and other tauopathies comprising administering to a subject in need thereof a dosage form comprising at least about 0.1 mg of a fatty-acid conjugated compounds of formula I and it various classes and subclasses as described herein, wherein W ranges between about 15 and about 22 carbons, having an activity in the inhibition of methylesterase ($IC_{50}$) of less than about 50 μM.

According to one aspect, the present invention provides methods of treating, ameliorating, controlling, or preventing neurodegenerative diseases such as Alzheimer's disease and other tauopathies comprising administering to a subject in need thereof a dosage form comprising at least about 8 mg of a fatty-acid conjugated compound of formula I and it various classes and subclasses as described herein, wherein W ranges between about 15 and about 22 carbons, having an activity in the inhibition of methylesterase ($IC_{50}$) of less than about 50 μM.

Synucleopathies

Synucleopathies are a class of neurodegenerative disorders associated with abnormal phosphorylation of certain neuronal proteins such as alpha-synuclein. Such abnormal phosphorylation is an early event that leads to their aggregation, formation of neuronal inclusions, and ultimately, loss of neuronal function. As described herein, one such synucleopathy of particular interest, inter alia, is Parkinson's Disease. Lewy bodies are aggregates of phosphorylated alpha-synuclein with a pathogenic role in Parkinson's disease, dementia with Lewy bodies, and Multiple system atrophy (Ma, Q. et. al., J. Alzheimers Dis. 5(2):139-48, 2003), among others.

Parkinson's Disease is the second most frequent neurodegenerative disorder after Alzheimer's Disease. Clinically, the cardinal symptoms of Parkinson's Disease include tremor, muscle rigidity, slowness of voluntary movement and postural instability. Although Parkinson's Disease neuropathology involves a number of different neurotransmitter pathways, the disabling symptoms cited above are attributed primarily to a deficiency in brain dopamine. Among the different dopaminergic systems of the brain, the ascending nigrostriatal pathway is most severely damaged in Parkinson's Disease. Parkinson's Disease researchers rely on model systems to explore various aspects of the disease. MPTP (1-methyl-4-phenyl-1,2,3,6-tetrahydropyridine) model has become the most commonly known in Parkinson's Disease research, since it is the only known dopaminergic neurotoxin capable of causing a clinical picture in both humans and monkeys that is similar to that seen in Parkinson's Disease. (see Jackson-Lewis V. and Przedborski S., "Protocol for the MPTP Mouse Model of Parkinson's Disease, (1-methyl-4-phenyl-1,2,3,6-tetrahydropyridine)", Nature Protocols Vol 2 (1) 2007 Pages 141-152).

In certain embodiments, the present invention provides methods of treating ameloriating, controlling, or preventing neurodegenerative diseases such as Parkinson's disease and other synucleopathies by administering a compound and/or extract of Formula I or a comestible containing such an extract, provided that at least 0.1 mg of the extract is administered.

In certain embodiments, the present invention provides methods of treating ameloriating, controlling, or preventing neurodegenerative diseases such as Parkinson's disease or other synucleopathies by administering a compound and/or extract of Formula I or a comestible containing such an extract, provided that at least 8 mg of the extract is administered.

According to one aspect, the present invention provides methods of treating, ameliorating, controlling, or preventing neurodegenerative diseases such as Parkinson's disease or other synucleopathies comprising administering to a subject in need thereof a dosage form comprising at least about 0.1 mg of a fatty-acid conjugated compound of formula I and it various classes and subclasses as described herein, wherein W ranges between about 15 and about 22 carbons, having an activity in the inhibition of methylesterase ($IC_{50}$) of less than about 50 μM.

According to one aspect, the present invention provides methods of treating, ameliorating, controlling, or preventing neurodegenerative diseases such as Parkinson's disease or other synucleopathies comprising administering to a subject in need thereof a dosage form comprising at least about 8 mg of a fatty-acid conjugated compound of formula I and it various classes and subclasses as described herein, wherein W ranges between about 15 and about 22 carbons, having an activity in the inhibition of methylesterase ($IC_{50}$) of less than about 50 μM.

Diabetes, Insulin Resistance and Metabolic Syndrome

Excessive dietary intakes of carbohydrates and fats, combined with a lack of adequate physical exercise are recognized as important causative factors in the development of type 2 diabetes and obesity. (see Stettler, R., M. Ith, et al., 2005, "Interaction Between Dietary Lipids and Physical Inactivity on Insulin Sensitivity and on Intramyocellular Lipids in Healthy Men", Diabetes Care 28(6): 1404-9; and Weiss, R., S. Dufour, et al, 2003, "Prediabetes in Obese Youth: A Syndrome of Impaired Glucose Tolerance, Severe Insulin Resistance, and Altered Myocellular and Abdominal Fat Partitioning", Lancet 362(9388): 951-7). Chronically elevated levels of glucose and free fatty acids lead to impaired glucose tolerance, dyslipidemia and insulin resistance (see Savage, D. B., K. F. Petersen, et al., 2007, "Disordered Lipid Metabolism and the Pathogenesis of Insulin Resistance", Physiol. Rev. 87(2): 507-20). Individuals with these metabolic disturbances are considered to be in a pre-diabetic condition and are at significantly greater risk of developing not just type 2 diabetes, but other progressively developing complications collectively described herein as metabolic syndrome, which may include disorders such as hyperglycemia, reduced insulin production and/or secretion and insulin resistance (see Laaksonen, D. E., H. M. Lakka, et al., 2002, "Metabolic Syndrome and Development of Diabetes Mellitus: Application and Validation of Recently Suggested Definitions of the Metabolic Syndrome in a Prospective Cohort Study", Am. J. Epidemiol. 156(11): 1070-7; Moller, D. E. and K. D. Kaufman, 2005, "Metabolic Syndrome: A Clinical and Molecular Perspective", Annual Rev. Med. 56: 45-62). Given the scale of this world-wide clinical problem, there is a pressing need to develop novel and effective strategies to halt or slow the progressive nature of the metabolic syndrome and related disorders.

The uptake, utilization, and metabolism of glucose in multiple cell types, is coordinately regulated by insulin and other intracellular signaling pathways. Two critical protein components of the insulin signaling pathway are Insulin Receptor Substrate 1 and 2 (IRS-1/2). Chronic insulin signaling and elevated nutrient and fatty acid levels leads to chronic Ser/Thr phosphorylation of IRS-1/2 by multiple downstream kinases. This has been proposed as one the mechanisms of development of insulin resistance, and some of the kinases implicated in this process include PI3K, Akt, PKC isoforms, mTOR, IκBα, and p70S6K (see Furukawa, N., P. Ongusaha, et al., 2005, "Role of Rho-kinase in Regulation of Insulin Action and Glucose Homeostasis", Cell Metab. 2(2): 119-29; Tremblay, F., A. Gagnon, et al., 2005, "Activation of the Mammalian Target of Rapamycin Pathway Acutely Inhibits Insulin Signaling to Akt and Glucose Transport in 3T3-L1 and Human Adipocytes", Endocrinology 146(3): 1328-37; and Morino, K., K. F. Petersen, et al., 2006, "Molecular Mechanisms of Insulin Resistance in Humans and Their Potential Links with Mitochondrial Dysfunction." Diabetes 55 Suppl. 2: S9-S15).

Multiple kinases relevant to the metabolic syndrome are dephosphorylated by Ser/Thr phosphatases such as protein phosphatase 2A (PP2A), protein phosphatase 1 (PP1) and protein phosphatase 5 (PP5). These phosphatases form 'signaling modules' with various kinases and are considered to have an important role in maintaining the balance of phosphorylated and dephosphorylated forms of proteins involved in insulin signaling. (see Westphal, R. S., R. L. Coffee, Jr., et al., 1999, "Identification of Kinase-phosphatase Signaling Modules Composed of p70 S6 Kinase-protein Phosphatase 2A (PP2A) and p21-activated kinase-PP2A", J. Biol. Chem. 274(2): 687-92; Andrabi, S., 0. V. Gjoerup, et al., 2007, "Protein Phosphatase 2A Regulates Life and Death Decisions via Akt in a Context-dependent Manner", Proc. Natl. Acad. Sci. USA 104(48): 19011-6; and Harwood, F. C., L. Shu, et al., 2008, "mTORC1 Signaling Can Regulate Growth Factor Activation of p44/42 Mitogen-activated Protein Kinases through Protein Phosphatase 2A", J. Biol. Chem. 283(5): 2575-85).

Targeting therapeutics to correct imbalances in IRS-1/2 signaling and abnormal activation of downstream kinases may thus constitute a novel approach to ameliorating insulin resistance. Downregulation of PP2A and PP1 activities has been reported to lead to decreased insulin secretion in pancreatic beta cells, suggesting that normal PP2A activity is important in $Ca^{2+}$-mediated insulin granule exocytosis. (see Sato, Y., P. Mariot, et al., 1998, "Okadaic Acid-induced Decrease in the Magnitude and Efficacy of the $Ca^{2+}$ Signal in Pancreatic beta Cells and Inhibition of Insulin Secretion", Br. J. Pharmacol. 123(1): 97-105). Collectively, these findings indicate that an incremental upregulation of PP2A activity may have a beneficial impact on ameliorating insulin resistance and enhancing insulin secretion, and may be an innovative approach to therapeutic intervention in diabetes-related metabolic disorders.

According to one aspect, the present invention provides methods of treating, ameliorating, controlling, or preventing diabetes, insulin resistance, and metabolic syndrome comprising administering to a subject in need thereof a dosage form comprising at least about 0.1 mg of a fatty-acid conjugated compound of formula I and it various classes and subclasses as described herein (e.g., Ib) wherein W ranges between about 15 and about 22 carbons, having an activity in the inhibition of methylesterase ($IC_{50}$) of less than about 50 μM.

According to one aspect, the present invention provides methods of treating, ameliorating, controlling, or preventing diabetes, insulin resistance, and metabolic syndrome comprising administering to a subject in need thereof a dosage form comprising at least about 8 mg of a fatty-acid conjugated compound of formula I and it various classes and subclasses as described herein (e.g., Ib) wherein W ranges between about 15 and about 22 carbons, having an activity in the inhibition of methylesterase ($IC_{50}$) of less than about 50 μM.

VI. Combination Therapy and Screening

It is contemplated that a provided compound can be used in combination with other drugs or therapeutic agents.

In some embodiments, compounds as described herein are administered in combination with one or more other agents intended to treat the same condition, or disease. As used herein, additional therapeutic agents that are normally administered to treat a particular disease, or condition, are known as "appropriate for the disease, or condition, being treated."

The present invention provides methods comprising steps of providing a plurality of compounds of formula I, assessing the effect(s) of at least one of the compounds of the plurality on PP2A activity and/or determining that at least one compound modulates PP2A activity.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference.

EXAMPLES

The compounds of Formula I may be prepared synthetically by methods known to those of skill in the art. Examples illustrating these methods are detailed below.

Example 1

Synthesis of (9Z,12S)-12-hydroxy-N-[2-(5-hydroxy-1H-indol-3-yl)ethyl]octadec-9-enamide (Compound I-28)

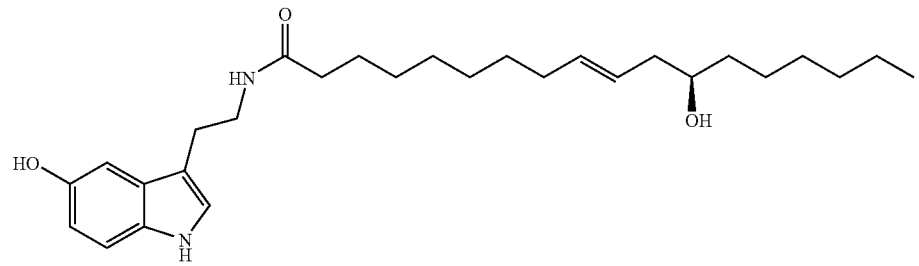 [SMILES: CCCCCC[C@@H](O)C/C=C/CCCCCCCC(=O)NCCc1c[nH]c2ccc(O)cc12]

(R)-12-Hydroxy-cis-9-octadecenoic acid (60 mg, 0.2 mmole) and HATU (O-(7-Azabenzotriazol-1-yl)-N,N,N',N'-tetramethyluronium hexafluorophosphate, 70 mg, 0.2 mmole) were dissolved in pyridine (1 mL). The reaction mixture was stirred at room temperature for 30 minutes. Serotonin hydrochloride (42 mg, 0.2 mmole) was added to the reaction mixture. The reaction mixture was stirred at room temperature overnight, water (10 mL) was added, the water-insoluble product precipitated and was isolated by filtration to yield the desired product. The desired product was washed with additional water (3×10 mL) and dried under the vacuum. 45 mg of the desired compound was obtained in 50% yield. $^{1}$H-NMR (500 MHz, CD$_{3}$OD) δ 0.91 (t, J=6.9 Hz, 3H), 1.31-1.61 (m, 20H), 2.07 (dt, J=6.0, 13.0 Hz, 2H), 2.15-2.20 (m, 4H), 2.88 (t, J=7.3 Hz, 2H), 3.45 (t, J=7.3 Hz, 2H), 3.55 (m, 1H), 5.44 (m, 2H), 6.67 (dd, J=8.8, 2.0 Hz, 1H), 6.95 (d, J=2.0 Hz, 1H), 7.01 (s, 1H), 7.16 (d, J=8.8 Hz, 1H); $^{13}$C-NMR (125 MHz, CD$_{3}$OD) δ 13.7, 22.9, 25.3, 25.6, 26.0, 27.6, 29.5, 29.6, 29.8, 29.9, 32.3, 34.1, 35.5, 36.4, 36.9, 40.4, 71.8, 102.7, 111.5, 111.6, 111.8, 123.4, 126.1, 131.8, 132.1, 132.3, 150.3, 175.5; ES-MS: mass calculated for Chemical Formula: C$_{28}$H$_{45}$N$_{2}$O$_{3}$ 457.7 (MH$^{+}$). Found m/z 457.4.

Example 2

Synthesis of 12-hydroxy-N-[2-(5-hydroxy-1H-indol-3-yl)ethyl]octadecanamide (Compound I-29)

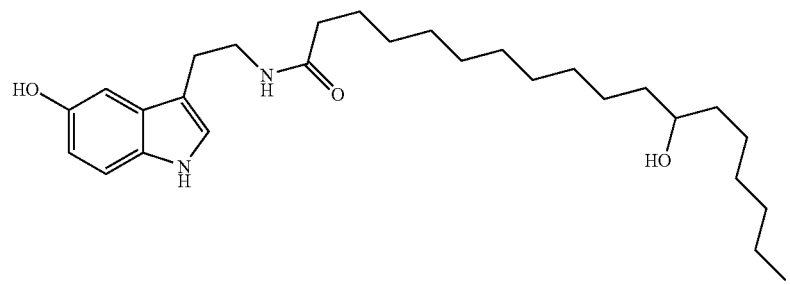 [SMILES: CCCCCCC(O)CCCCCCCCCCC(=O)NCCc1c[nH]c2ccc(O)cc12]

12-Hydroxy-octadecenoic acid (60 mg, 0.2 mmole) and HATU (O-(7-azabenzotriazol-1-yl)-N,N,N',N'-tetramethyluronium hexafluorophosphate, 70 mg, 0.2 mmole) were dissolved in pyridine (1 mL). The reaction mixture was stirred at room temperature for 30 min. Serotonin hydrochloride (42 mg, 0.2 mmole) was added to the reaction mixture and the reaction mixture was stirred at room temperature overnight, water (10 mL) was added, the water-insoluble product precipitated and was isolated by filtration to yield the desired product. The desired product was washed with water (3×10 mL) and dried under the vacuum. 46 mg of product was obtained in 50% yield. $^{1}$H-NMR (500 MHz, CD$_{3}$OD) δ 0.93 (t, J=6.6 Hz, 3H), 1.30-1.59 (m, 28H), 2.17 (t, J=7.6 Hz, 2H), 2.88 (t, J=7.3 Hz, 2H), 3.33 (t, J=7.3 Hz, 2H), 3.47 (m, 1H), 6.67 (dd, J=8.9, 2.2 Hz, 1H), 6.95 (d, J=2.0 Hz, 1H), 7.02 (s, 1H), 7.16 (d, J=8.9 Hz, 1H); $^{13}$C-NMR (125 MHz, CD$_{3}$OD) δ 14.5, 23.8, 24.2, 26.4, 26.8, 26.9, 27.1, 30.3, 30.5, 30.6, 30.7, 30.8, 33.1, 37.2, 38.4, 41.3, 72.5, 103.5, 112.3, 112.4, 112.7, 124.2, 129.5, 133.1, 151.1, 176.4; ES-MS: mass calculated for Chemical Formula: C$_{28}$H$_{47}$N$_{2}$O$_{3}$ 459.7 (M+Na). Found m/z 481.4.

Example 3

Synthesis of 3-hexadecyl-1-[2-(5-hydroxy-1H-indol-3-yl)ethyl]urea (Compound I-30)

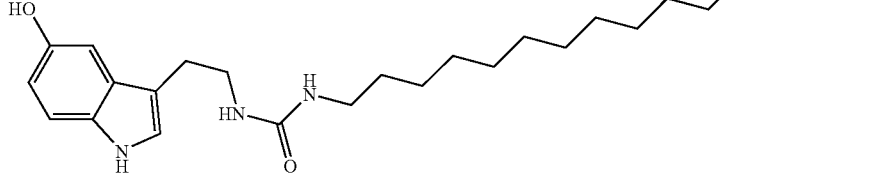

Serotonin hydrochloride (42 mg, 0.2 mmole) and hexadecyl isocyanate (54 mg, 0.2 mmole) were dissolved in pyridine (1 mL). The reaction mixture was stirred at room temperature overnight, water (10 mL) was added, the water-insoluble urea product precipitated and was isolated by filtration to yield the desired product. The desired product was washed with water (3×10 mL) and dried under the vacuum to yield the desired compound (60 mg, 67% yield) as a white solid. $^{1}$H NMR (500 MHz, MeOH-d$_{4}$) δ 0.92 (t, J=6.9 Hz, 3H), 1.30 (bs, 26H), 1.46 (m, 2H), 2.86 (t, J=7.25 Hz, 2H), 3.08 (t, J=7.25 Hz, 2H), 3.63 (t, J=7.25 Hz, 2H), 6.66 (dd, J=2.2, 8.5, 1H), 6.94 (d, J=2.2 Hz, 1H), 7.02 (s, 1H), 7.16 (d, J=8.5 Hz, 1H), $^{13}$C NMR (125 MHz, MeOH-d$_{4}$) δ 14.6, 23.8, 27.3, 27.9, 30.5, 30.8, 31.2, 33.1, 41.0, 41.7, 103.5, 112.3, 112.5, 112.6, 124.4, 129.4, 133.1, 151.1, 161.4; ES-MS: mass calculated for Chemical Formula: C$_{27}$H$_{46}$N$_{3}$O$_{2}$ 444.7 (MH$^{+}$). Found m/z 444.4.

Example 4

Synthesis of 1-[2-(5-hydroxy-1H-indol-3-yl)ethyl]-3-octadecylurea (Compound I-31)

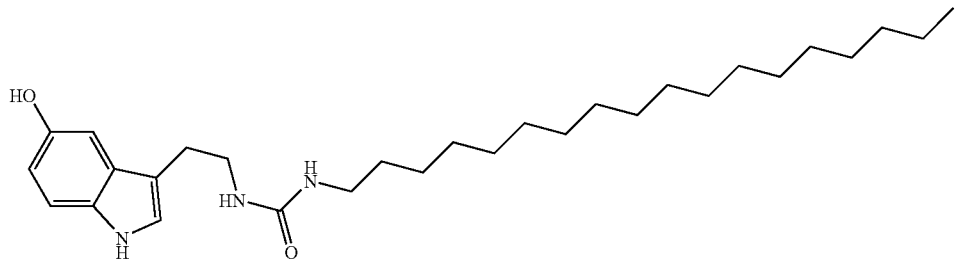 [SMILES: CCCCCCCCCCCCCCCCCCNC(=O)NCCc1c[nH]c2ccc(O)cc12]

Serotonin hydrochloride (42 mg, 0.2 mmole) and octadecyl isocyanate (60 mg, 0.2 mmole) were dissolved in pyridine (1 mL). The reaction mixture was stirred at room temperature overnight, water (10 mL) was added, the water-insoluble urea product precipitated and was isolated by filtration to yield the desired product. The desired product was washed with water (3×10 mL) and dried under the vacuum to yield the desired compound (50 mg, 53% yield) as a white solid. $^1$H NMR (500 MHz, MeOH-$d_4$) δ 0.92 (t, J=6.9 Hz, 3H), 1.30 (bs, 26H), 1.46 (m, 2H), 2.86 (t, J=7.25 Hz, 2H), 3.09 (t, J=7.25 Hz, 2H), 3.43 (t, J=7.25 Hz, 2H), 6.67 (dd, J=2.2, 8.5, 1H), 6.94 (d, J=2.2 Hz, 1H), 7.02 (s, 1H), 7.16 (d, J=8.5 Hz, 1H); $^{13}$C NMR (125 MHz, MeOH-$d_4$) δ 14.5, 23.8, 27.2, 28.0, 30.5, 30.8, 31.2, 33.1, 41.1, 41.9, 103.5, 112.3, 112.5, 112.6, 124.4, 129.5, 133.1, 151.1, 161.3; ES-MS: mass calculated for Chemical Formula: $C_{29}H_{50}N_3O_2$ 472.7 (MH$^+$). Found m/z 472.5.

Example 5

General Procedure for Modifying a Free —OH Group (on a Tryptamide Compound)

A tryptamide starting material with a free hydroxyl group, such as Compound I-63, is dissolved in pyridine and a slight molar excess of an acylating reagent is added and the reaction mixture is stirred at RT for about 1 to about 6 hours. Reaction completion is monitored by HPLC and once complete, the reaction mixture is diluted with NH$_4$Cl, and extracted with dichloromethane (DCM). The DCM layer is washed with NH$_4$Cl (aq., sat, 3× washes), is dried over magnesium sulfate, is concentrated and is dried under vacuum to afford the desired compound.

Exemplary syntheses of the general method in Example 5 are described in Examples below.

Example 6

Synthesis of 4-(3-(2-icosanamidoethyl)-1H-indol-5-yloxy)-4-oxobutanoic acid (Compound I-32)

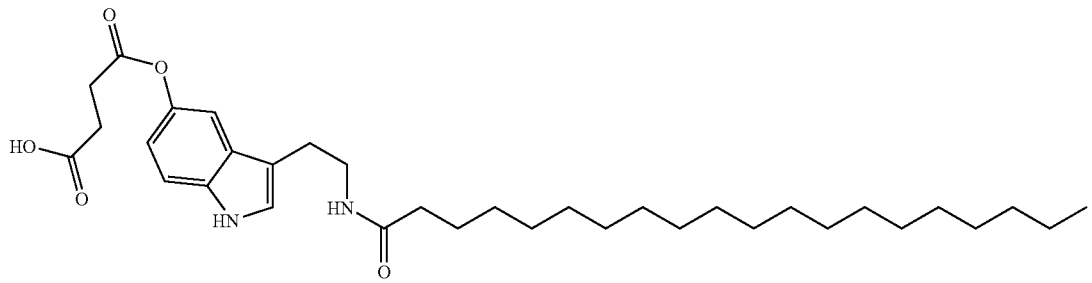 [SMILES: CCCCCCCCCCCCCCCCCCCC(=O)NCCc1c[nH]c2ccc(OC(=O)CCC(=O)O)cc12]

Compound I-63 (0.1 mmol, 0.047 g) was dissolved in pyridine (2 mL), succinic anhydride (0.11 mmol) was added and the reaction mixture was stirred at room temperature (between about 20° C. and about 28° C.). Upon reaction completion (monitored by HPLC) the reaction mixture was diluted with NH$_4$Cl (aq., sat, 5 mL) and extracted with DCM (5 mL). The DCM layer was further washed with NH$_4$Cl (aq., sat, 5 mL×3), dried over magnesium sulfate, concentrated and dried under vacuum to yield the desired compound (43 mg, 75% yield). $^1$H NMR (500 MHz, MeOH-$d_4$): δ 0.88 (t, J=6.9 Hz, 3H), 1.27 (bs, 26H), 1.49-1.56 (m, 2H), 2.12 (t, J=7.1 Hz, 2H), 2.63 (t, J=7.1 Hz, 2H), 2.83 (t, J=7.25 Hz, 2H), 3.48 (t, J=7.25 Hz, 2H), 6.78 (d, J=8.5, 1H), 7.12 (s, 1H), 7.29 (s, 1H), 7.41 (d, J=8.5 Hz, 1H); $^{13}$C NMR (125 MHz, MeOH-$d_4$): δ 14.8, 23.8, 25.3, 26.9, 30.5, 30.9, 30.0, 30.0-30.1 (6C), 30.2 (7C), 31.2, 33.1, 41.7, 112.3, 113.8, 114.6, 117.1, 124.8, 129.4, 133.1, 147.2, 173.4, 178.1; ES-MS: mass calculated for Chemical Formula: $C_{34}H_{54}N_2O_5$ 571.4 (MH$^+$). Found m/z 571.5.

Example 7

Synthesis of 3-(2-icosanamidoethyl)-1H-indol-5-yl acetate (Compound I-33)

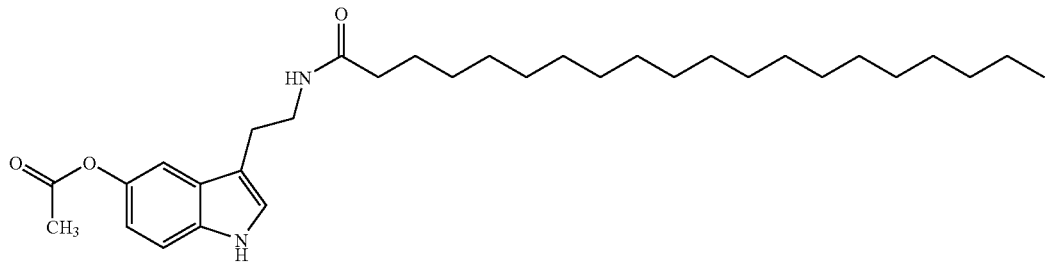 [SMILES: CCCCCCCCCCCCCCCCCCCC(=O)NCCc1c[nH]c2ccc(OC(C)=O)cc12]

Compound I-63 (0.1 mmol, 0.047 g) was dissolved in pyridine (2 mL) and 0.11 mmol of acetic anhydride was added, and the reaction mixture was stirred at RT. Upon reaction completion (monitored by HPLC) the reaction mixture was diluted with $NH_4Cl$ (aq., sat, 5 mL) and extracted with DCM (5 mL). The DCM layer was washed with $NH_4Cl$ (aq., sat, 5 mL×3), dried over magnesium sulfate, concentrated and dried under vacuum to yield the desired compound (42 mg, 81% yield). $^1H$ NMR (500 MHz, $CDCl_3$): δ 0.88 (t, J=6.9 Hz, 3H), 1.25 (bs, 26H), 1.53-1.57 (m, 2H), 2.02 (t, J=7.1 Hz, 2H), 2.31 (s, 3H), 2.83 (t, J=7.25 Hz, 2H), 3.48 (t, J=7.25 Hz, 2H), 5.49 (bs, 1H), 6.88 (d, J=8.5, 1H), 7.07 (s, 1H), 7.28 (s, 1H), 7.32 (d, J=8.5 Hz, 1H), 8.16 (bs, 1H); $^{13}C$ NMR (125 MHz, $CDCl_3$): δ 14.2, 21.2, 22.7, 25.3, 25.8, 29.3-29.7 (13C), 30.4, 31.2, 36.9, 39.5, 110.9, 111.7, 113.4, 116.3, 123.4, 127.7, 134.2, 144.1, 170.6, 173.2; ES-MS: mass calculated for Chemical Formula: $C_{32}H_{52}N_2O_3$ 513.4 ($MH^+$). Found m/z 513.5.

Example 8

General Procedure for Preparation of Compounds in Example 9 Through Example 13

Arachidic acid (0.11 mmol, 0.034 g) is mixed with HATU (0.11 mmol, 0.042 g) and triethylamine (0.5 mL, co-solvent) in DMF (2 mL, anhydrous). The reaction mixture is stirred for 30 minutes, and the appropriately substituted compound (0.1 mmol) is added. The reaction mixture is stirred at room temperature for about 4 to about 16 hrs (monitored by HPLC). Upon completion $NH_4Cl$ (10 mL, aq., saturated) is added and the solid is collected by filtration, is washed with water (10 mL×2), $NaHCO_3$ (10 mL×2, aq., is saturated) and is washed finally by acetonitrile (2 mL). The desired product is dried under the vacuum.

Exemplary syntheses of the general method in Example 8 are described in Example 9 through Example 13.

Example 9

Synthesis of N-[2-(5-methoxy-1H-indol-3-yl)ethyl] icosanamide (Compound I-34)

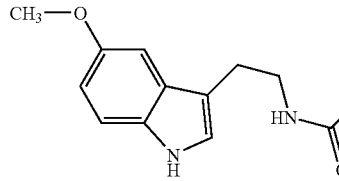

The desired compound is prepared substantially as described above in Example 8 except that 5-methoxy-tryptamine is used as the starting material. ES-MS: mass calculated for Chemical Formula: $C_{31}H_{52}N_2O_2$ 484.8 (M+).

Example 10

Synthesis of N-[2-(5-fluoro-1H-indol-3-yl)ethyl] icosanamide (Compound I-35)

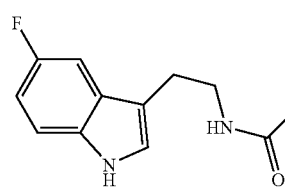

The desired compound is prepared substantially as described above in Example 8 except that 5-fluoro-tryptamine is used as the starting material. $^1$H NMR (500 MHz, DMSO-d6): 0.82 (t, 3H, J=6.9 Hz), 1.15-1.26 (m, 16H), 1.51 (m, 2H), 2.09 (t, 2H, J=7.6 Hz), 2.87 (t, 2H, J=7.6 Hz), 3.41 (q, 2H, J=7.6 Hz), 6.74 (t, 1H, J=8.7 Hz), 7.14 (s, 1H), 7.22 (d, 1H, J=8.6 Hz), 7.28 (dd, 1H, J=2.2 Hz, J=8.6 Hz); ES-MS: mass calculated for Chemical Formula $C_{30}H_{49}FN_2O$ 473.7 (MH+). Found (M+H) m/z 473.4.

Example 11

Synthesis of N-[2-(5-methyl-1H-indol-3-yl)ethyl]icosanamide (Compound I-36)

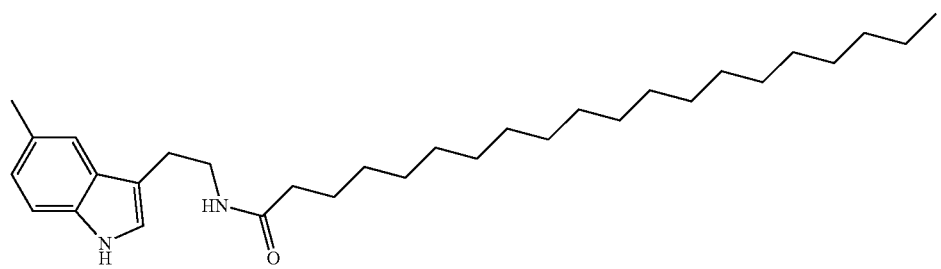 [SMILES: CCCCCCCCCCCCCCCCCCCC(=O)NCCc1c[nH]c2ccc(C)cc12]

The desired compound is prepared substantially as described above in Example 8 except that 5-methyl-tryptamine is used as the starting material. $^1$H NMR (500 MHz, DMSO-d6): 0.89 (t, 3H, J=7.1 Hz), 1.16-1.29 (m, 16H), 1.47 (m, 2H), 2.03 (t, 2H, J=7.5 Hz), 2.34 (s, 3H), 2.67 (t, 2H, J=7.5 Hz), 3.61 (t, 2H, J=6.7 Hz), 6.87 (d, 1H, J=8.7 Hz), 7.02 (s, 1H)), 7.13 (d, 1H, J=6.7 Hz), 7.38 (s, 1H); ES-MS: mass calculated for Chemical Formula $C_{31}H_{52}N_2O$ 469.8 (MH+). Found (M+H) m/z 469.5.

Example 12

Synthesis of N-[2-(1H-indol-3-yl)ethyl]-N-methylicosanamide (Compound I-38)

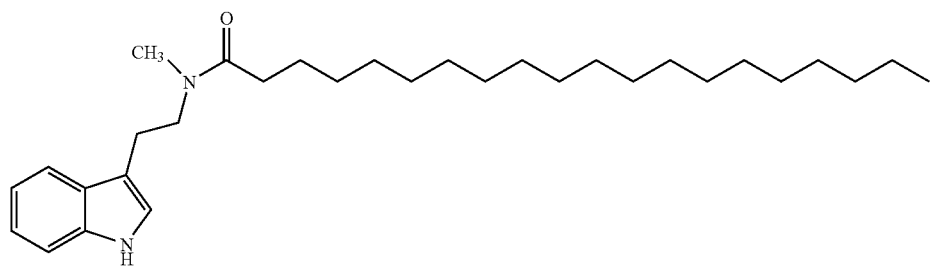 [SMILES: CCCCCCCCCCCCCCCCCCCC(=O)N(C)CCc1c[nH]c2ccccc12]

The desired compound is prepared substantially as described above in Example 8 except that N-ω-methyltryptamine is used as the starting material. $^1$H NMR (500 MHz, DMSO-d6): 0.84 (t, 3H, J=6.8 Hz), 1.16-1.33 (m, 16H), 1.52 (m, 2H), 2.62 (t, 2H, J=7.6 Hz), 3.59-3.62 (m, 2H), 7.21-7.26 (m, 1H), 7.53-7.71 (m, 2H), 7.84 (d, 1H, J=7.2 Hz), 8.02 (d, 1H, J=7.2 Hz); ES-MS: mass calculated for Chemical Formula $C_{31}H_{52}N_2O$ 469.8 (MH+). Found: 469.5 (M+H) m/z.

Example 13

Synthesis of N-Methyl-N-[2-(5-methoxy-1H-indol-3-yl)ethyl]icosanamide (Compound I-37)

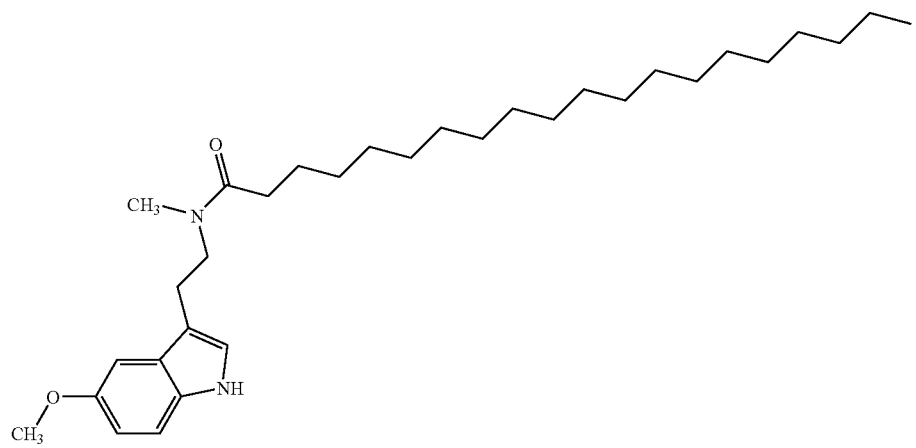 [SMILES: CCCCCCCCCCCCCCCCCCCC(=O)N(C)CCc1c[nH]c2ccc(OC)cc12]

The desired compound is prepared substantially as described above in Example 8 except that 5-methoxy-2-N-methyl-tryptamine is used as the starting material. ES-MS: mass calc'd for Chemical Formula: $C_{32}H_{54}N_2O_2$ 498.78 (M+).

Example 14

Preparation of 2-(5-hydroxy-1H-indol-3-yl)-N-octadecylacetamide (Compound I-39)

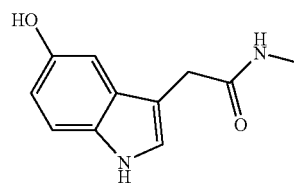

Commercial 5-hydroxy-indolyl-3-acetic acid (0.11 mmol, 0.021 g) was mixed with HATU (0.11 mmol, 0.042 g) and triethylamine (0.5 mL, co-solvent) in DMF (2 mL, anhydrous). The reaction mixture was stirred for 30 minutes and octadecylamine (0.1 mmol, 0.026 g) was added. The reaction mixture was stirred at room temperature for overnight (monitored by HPLC). Upon reaction completion, NH$_4$Cl (10 mL, aq., saturated) was added and the solid was collected by filtration, washed with water (10 mL×2), NaHCO3 (10 mL×2, aq., saturated) and finally by acetonitrile (2 mL). The product was dried under the vacuum to afford the desired compound as an off-white solid (74%, 0.033 g). $^1$H-NMR (500 MHz, (CD$_3$)$_2$SO): 0.84 (t, 3H, J=6.9 Hz), 1.18-1.29 (m, 12H), 1.38 (m, 2H), 3.01 (s, 2H), 6.54 (d, 1H, J=7.1 Hz), 6.81 (s, 1H), 7.00 (d, 1H, J=2.2 Hz), 7.09 (d, 1H, J=7.1 Hz), 7.82 (t, 1H, J=5.7 Hz), 8.52 (s, 1H), 10.49 (s, 1H). $^{13}$C NMR (125 MHz, (CD$_3$)$_2$SO): d 13.2, 23.2, 25.8, 29.3-29.7 (11C), 30.4, 31.2, 36.9, 102.6, 108.0, 111.2, 111.5, 123.8, 127.9, 130.6, 150.1, 170.5; ES-MS: mass calc'd for Chemical Formula $C_{28}H_{46}N_2O_2$ 443.7 (MH+). Found (M+Na) m/z 465.3.

Example 15

Preparation of N-(2-(5-hydroxy-1H-indol-3-yl)ethyl)icosanamide (Compound I-63)

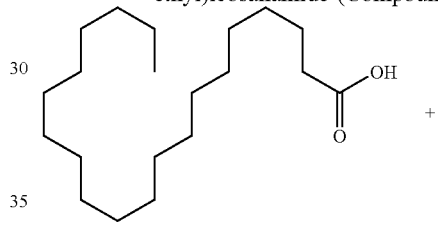

-continued

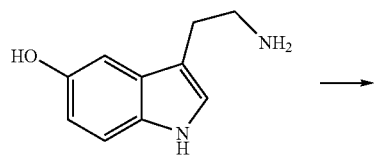

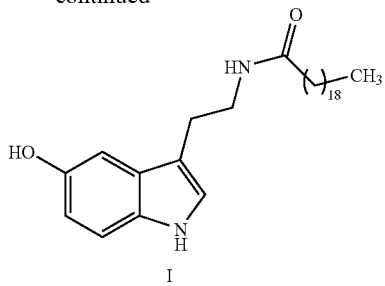

Arachidic acid (9.38 g, 30 mmol) was mixed with the appropriate amounts (30-45 mmol) of a coupling reagent, and if needed, an additional activating agent (10-45 mmol) (e.g., HOBt, heterocyclic base, heterocyclic acid) and/or organic base (10-60 mmol) (e.g., triethylamine, DIEA, pyridine, DABCO, non-nucleophilic basic nitrogen containing molecule) in an appropriate solvent (e.g., DMF, THF, dioxane, DCM, DCE, glyme, diglyme). The reaction mixture was stirred for 0.5-6 hrs, then serotonin (it's salt, free base or appropriately protected form) was added (either neat or premixed with solvent and/or organic base). The reaction mixture was stirred at room temperature for about 4 to about 16 hrs (monitored by HPLC). Upon completion the excess of the organic solvent was removed and the residual oil was treated with aqueous acid (0.1-3 N HCl, $NH_4Cl$ (aq., saturated), 0.1-1N $H_2SO_4$, etc.). N-(2-5-hydroxy-1H-indol-3-yl)ethyl)propionamide was collected by filtration as amorphous solid, washed with water (4×250 mL) and acetonitrile (100 mL). The product was dried under the vacuum and recrystallized from hot organic solvent (ethanol, methanol, isopropanol, acetonitrile, EtOAc, THF, etc.) to yield 12.43 g (88%) of N-(2-5-hydroxy-1H-indol-3-yl)ethyl)propionamide as an off-white amorphous solid.

Example 16

Alternate Preparation of N-(2-(5-hydroxy-1H-indol-3-yl)ethyl)icosanamide (Compound I-63)

An activated arachidic acid was mixed (stepwise or as a whole) with serotonin (in the salt, free base or appropriately protected form) in the presence of the appropriate amount of organic base (30-60 mmol) (e.g., triethylamine, DIEA, pyridine, DABCO, non-nucleophilic basic nitrogen containing molecule) in an appropriate solvent (e.g., DMF, THF, dioxane, DCM, DCE, glyme, diglyme). The reaction mixture was stirred for about 4 to about 24 hours (monitored by HPLC) at RT-40° C. Upon completion the excess of the organic solvent was removed and the residual oil was treated with aqueous acid (0.1-3 N HCl, $NH_4Cl$ (aq., saturated), 0.1-1N $H_2SO_4$, etc.). N-(2-5-hydroxy-1H-indol-3-yl)ethyl) propionamide was collected by filtration as amorphous solid, washed with water (4×250 mL) and acetonitrile (100 mL). The product was dried under the vacuum and recrystallized from hot organic solvent (ethanol, methanol, isopropanol, acetonitrile, EtOAc, THF, etc.) to yield N-(2-5-hydroxy-1H-indol-3-yl)ethyl)propionamide.

Example 17

Alternate preparation of N-(2-(5-hydroxy-1H-indol-3-yl)ethyl)icosanamide (Compound I-63)

This preparation is performed substantially as described in Example 15 except that the reaction is run under Schotten-Baumann conditions (use of a two-phase solvent system, consisting of water and an organic solvent. The base within the water phase neutralizes the acid, generated in the reaction, while the starting materials and product remain in the organic phase) in the presence of the appropriate amount of aqueous inorganic base (NaOH, $Na_2CO_3$, $NaHCO_3$, KOH, $K_2CO_3$, $KHCO_3$, $Na_3PO_4$, $K_3PO_4$) and an appropriate organic solvent not miscible with water.

Example 18

Comparison of Reaction Conditions in Preparation of N-(2-(5-hydroxy-1H-indol-3-yl)ethyl)icosanamide (Compound I-63)

Syntheses of N-(2-5-hydroxy-1H-indol-3-yl)ethyl)propionamide were performed substantially as described above except that different bases, coupling agents, and/or solvents were utilized. The table presented in FIG. 2 illustrates different combinations tested and the resulting yields and purities obtained.

As can be seen with reference to FIG. 2, solvents including DCM, DMF, THF, and combinations thereof each gave yields of at least 65%, and purities of at least 50%.

High yields were obtained with a variety of different solvents; inclusion of DMF as a solvent (whether alone or in combination) generally gave particularly high yields, particularly when HATU was used as a coupling agent and/or when DIEA was used as a base.

Higher purities (e.g., 80% or higher) were obtained with THF or DMF, or with solvent combinations in including one of these. Particularly high purities (>95%) were obtained when DMF was used, whether alone or in combination.

Example 19

Summary of Reaction Conditions Utilized in Examples 1-18

FIG. 1 presents a Table summarizing the different reaction conditions utilized to prepare compounds of formula I as set forth in Examples 1-14. FIG. 1 demonstrates that higher yields of 50% to 81% were obtained with DCM and/or pyridine.

Consideration of FIG. 1, particularly in light of FIG. 2 (corresponding to Examples 15-17), reveals, among other things, that using THF and DMF as solvents and TEA or DIEA as a base resulted in significantly higher yields and higher purities than those experiments using other solvents and/or bases.

Biological Protocols

Described below are assays that measure the biological activity of provided compounds, in particular, for their activity in: (a) the modulation of the phosphatase activity of PP2A towards non-protein substrates (e.g., pNPP); (b) in the modulation of the phosphatase activity of PP2A towards protein substrates (e.g., phosphorylase a); (c) in the modulation of the carboxyl methyltransferase activity (i.e., which is also referred to herein as the carboxyl methylating activity of the protein phosphatase 2A specific methyltransferase (MTase), wherein such activity results in PP2A methylation); and/or (d) in the modulation of carboxyl methylesterase activity (i.e., which is also referred to hereing as the carboxyl demethylating activity of the protein phosphatase specific protein methylesterase (MEase), wherein such activity results in PP2A demethylation). The data are represented as $IC_{50}$ values, where the $IC_{50}$ value is a measure of the effectiveness of a compound in inhibiting a biological or biochemical function. This quantitative measure indicates how much of a particular substance is needed to inhibit a given biological process (or component of a process, e.g. an enzyme) by half, i.e., $IC_{50}$ represents the concentration of a substance that is required for 50% inhibition. Exemplary results of provided compounds are presented in Table 2 below.

Example 20

Phosphatase Activity Using pNPP as Substrate

The present example demonstrates that compounds of the present invention modulate phosphatase activity of the un-methylated form of PP2A towards a non-protein substrate like pNPP. PP2A (10-200 nM) and pNPP (5-10 mM, Sigma) were mixed into 96-well plate (Fisher Scientific Inc.) in 50 µL of the buffer required. Reactions were performed at room temperature, and fully stopped by adding equal volume of 0.1 M EDTA. Production of p-nitrophenol (PNPP) was quantified by absorbance of reaction mixtures at 405 nm using the VMax® microplate reader (Molecular Devices). Exemplary results are presented in Table 2 below.

Example 21

Phosphatase Activity Using Phosphorylase as a Substrate

The present example demonstrates that compounds of the present invention modulate the phosphatase activity of the un-methylated PP2A towards protein substrates like phosphorylase a. $^{32}$P-labeled phosphorylase a was made by incubating phosphorylase b (Sigma), phosphorylase b kinase (Sigma) and $^{32}$P-ATP (Amersham) at 30° C. in for 1 hour. After the reaction, proteins were precipitated by 50% $(NH_4)_2SO_4$ (final concentration) twice, and collected by centrifugation. The pellet was re-dissolved and dialyzed in a buffer containing 50 mM Tris-HCl (pH 6.9) and 1 mM DTT for 2×2 L at 4° C. overnight. Phosphorylase a (phospho-phosphorylase b) crystallized during the dialysis. The dialysate was centrifuged 14,000 r.p.m at 4° C. for 30 minutes, the supernatant was removed and purified $^{32}$P-labelled phosphorylase a was re-dissolved in +50% glycerol, and stored at −20° C.

To measure PP2A's phosphatase activity, PP2A (5-20 nM) was incubated with phosphorylase a (5-10 µM) at 37° C. 10% TCA (final concentration) and was added to the reaction to precipitate proteins. Supernatant that contains free $^{32}$P-phosphate group was added into scintillation counting solution (Ecoscint, National Diagnostics), and counted by scintillation counter (LS 6000SE, Beckman). Exemplary results are presented in Table 2 below.

Example 22

Measuring PP2A Demethylation with [$^{3}$H]-SAM and Purified Proteins

The present example demonstrates that compounds of the present invention modulate the methylesterase activity (i.e., the carboxyl demethylating activity of the protein phosphatase specific protein methylesterase (ME), wherein such activity results in PP2A demethylation. Methylated PP2A was made by incubating PP2A, His-tagged MTase and [$^{3}$H]-SAM together for 1 hour at room temperature, to reach maximum methylation (>90%). The reaction mixture was loaded onto mini SourceQ column (1 mL) that was pre-equilibrated with a buffer containing 50 mM MOPS and 1 mM DTT (pH 7.2) (Buffer A). MTase and free SAM were washed out of column with 10 mL of Buffer A containing 75 mM NaCl. PP2A (methylated and unmethylated) were eluted with 1.6 mL of Buffer A containing 350 mM NaCl. Fractions (0.2 mL each) were collected and the radioactivity in each fraction was measured using the scintillation counter (LS 6000SE, Beckman). Fractions with highest radioactivity were containing purified methylated PP2A were pooled with a total volume of 0.6 mL-0.8 mL. Purified methylated PP2A (50 nM-100 nM) was incubated with MEase (5 mM-20 mM) in 20 µl-50 µl reaction at room temperature for 30 minutes. The reaction was terminated by adding TCA (2 µL-6 µL) to a final concentration of 10%. Released [$^{3}$H]-methanol in supernatants was counted with scintillation counter (LS 6000SE, Beckman). Exemplary results are presented in Table 2 below.

Example 23

Measuring PP2A Methylation in 96-Well Plate Format

The present example demonstrates that compounds of the present invention modulate the methyltransferase activity [i.e., the carboxyl methylating activity of the protein phosphatase 2A specific methyltransferase (MTase)], wherein such activity results in PP2A methylation. Purified PP2A, MTase and [$^{3}$H]-SAM, were incubated in reaction buffer at 37° C. At the end of the reaction, mixture was added onto the membranes of 96-well filter plate (Multiscreen™, Millipore). The membranes were then pre-wetted with 70% ethanol (50 µL/well) and then subsequently washed with water (2×200 µL/well). The reaction in each well was terminated and the proteins (5 µL-20 µL) were precipitated by adding 25% ice-cold TCA. The plate was kept on ice for 30 minutes to ensure completion of protein precipitation. Excess of the free SAM was then removed by washing with 5% cold TCA (50 µL/well) and 70% cold ethanol (2×100 µL/well). Membranes were air-dried, radioactivity in each well was counted by TopCount$^{NXT}$ scintillation counter (Packard) with 25 µL/well of Microsinct™ 20 (PerkinElmer). Exemplary results are presented in Table 2 below.

Example 24

The present example demonstrates exemplary in vitro PP2A activity data of certain compounds of the present invention. Compounds of formulae described herein have been tested for their activity in the inhibition of the carboxyl demethylating activity of the protein phosphatase specific protein methylesterase and/or in the inhibition of methyltransferase, and PP2A. Data are presented as $IC_{50}$ values, where the $IC_{50}$ value is a measure of the effectiveness of a compound in inhibiting a biological or biochemical function. This quantitative measure indicates how much of a particular substance is needed to inhibit a given biological process (or component of a process, e.g. an enzyme) by half. In other words, $IC_{50}$ represents the concentration of a substance that is required for 50% inhibition.

Exemplary in vitro PP2A activity data of certain compounds of the present invention are shown in Table 2, and were generated using the protocols described above. Specifically, the column in Table 2 labeled "pNPP" refers to data obtained using the protocol from Example 19. The column labeled "Phosphorylase a" refers to data obtained using the protocol from Example 20. The column labeled "ME" refers to data obtained using the protocol from Example 21. The column labeled "MT" refers to data obtained using the protocol from Example 22.

Proteins including the PP2A A subunit, PP2A C subunit, PP2A AC dimer, PPME, and PPMT are purified by methods known in the art, including described in U.S. Patent Application 2006/0171938, Xing et al. Cell. 2008, 133(1):154-63, Xing et al. *Cell.* 2006, 127(2):341-53, Chao et al. Molecular Cell. 2006, 23(4):535-46. The coenzyme [$^3$H]-SAM or tritiated S-adenosyl methionine is obtained from any commercially available source (e.g., Perkin Elmer).

Example 24a

Measuring Turnover Rate of PP2A Methyl Ester using [$^3$H]-SAM and Purified Proteins The present example demonstrates that compounds of the present invention modulate MT activity, wherein such activity results in PP2A methylation and/or ME activity, wherein such activity results in PP2A demethylation, and/or the phosphatase activity of PP2A. PP2A (100 nM), MTase (10-100 nM), MEase (10-100 nm) and [$^3$H]-SAM (0.5 mM) (total volume of reaction was 25-50 ul) were incubated at 37° C. for 30 min. Reactions were stopped by 5% SDS or acetic acid (final concentration). The lids of eppendorf tubes (1.7 ml) were removed, so the tubes could be placed into scintillation vials. The vials were kept in warm room overnight. During this time, produced [$^3$H]-methanol evaporated out of the aqueous solution and dissolved into scintillation counting solution. Radioactivity was counted by scintillation counter (LS 6000SE, Beckman).

TABLE 2

| | ACTIVITY RANGE Activity Range 1 is >100 µM Activity Range 2 is 10 µM-100 µM Activity Range 3 is <10 µM | | | |
|---|---|---|---|---|
| COMPOUND NUMBER | pNPP ($IC_{50}$) | Phosphorylase a ($IC_{50}$) | ME ($IC_{50}$) | MT ($IC_{50}$) |
| I-29 | 3 | 1 | 2 | 2 |
| I-30 | 2 | 2 | 3 | 2 |
| I-31 | 2 | 2 | 3 | 2 |
| I-32 | 2 | 2 | 3 | 3 |
| I-33 | 2 | — | 3 | 3 |
| I-35 | 2 | 1 | 3 | 3 |
| I-36 | 2 | 1 | 2 | 3 |
| I-38 | 1 | — | 1 | 1 |
| I-39 | 2 | 2 | 3 | 2 |
| I-62 | 2 | 1 | 2 | 2 |
| I-63 | 1 | 1 | 3 | 2 |
| I-64 | 1 | 2 | 3 | 3 |
| I-65 | 1 | 2 | 3 | 3 |
| I-66 | 2 | 1 | 3 | 3 |
| I-67 | 2 | 1 | 1 | — |
| I-76 | 1 | — | 1 | 1 |
| I-77 | 1 | — | 1 | 1 |
| I-78 | 1 | — | 3 | 3 |
| I-79 | 1 | — | 2 | 3 |
| I-80 | 2 | — | 3 | 3 |

As can be seen with reference to above Table 2, certain compounds of the present invention modulate the phosphatase activity of PP2A towards non-protein substrates (e.g., pNPP) in the absence of ME and MT. In certain embodiments, compounds of the present invention show $IC_{50}$ values that range between 10 µM and 300 µM. In certain embodiments, compounds of the present invention show $IC_{50}$ values that range between 3 µM and 10 µM. In certain embodiments, compounds of the present invention show $IC_{50}$ values that range between 10 µM and 100 µM. In certain embodiments, compounds of the present invention show $IC_{50}$ values that range between 100 µM and 300 µM, and higher. $IC_{50}$ values within the range between 100 µM and 300 µM suggest that activity of PP2A with respect to non-protein substrates is comparable to presence of compounds described herein, or in the absence of compounds described herein. That is, such compounds do not have a direct material effect (in the absence of ME and MT) on PP2A activity toward non-protein substrates. A direct material effect may refer to compounds having an $IC_{50}$ of below 100 µM.

As can be seen with reference to above Table 2, certain compounds of the present invention modulate the phosphatase activity of PP2A towards protein substrates (e.g., phosphorylase a) in the absence of ME and MT. In certain embodiments, compounds of the present invention show $IC_{50}$ values that range between 10 µM and 300 µM. In certain embodiments, compounds of the present invention show $IC_{50}$ values that range between 10 µM and 100 µM. In certain embodiments, compounds of the present invention show $IC_{50}$ values that range between 100 µM and 300 µM, and higher. In certain embodiments, compounds of the present invention show $IC_{50}$ values that range between 100 µM and 300 µM, and higher. $IC_{50}$ values within the range between 100 µM and 300 µM suggest that activity of PP2a with respect to protein substrates is comparable to presence of compounds described herein, or in the absence of compounds described herein. That is, such compounds do not have a direct material effect (in the absence of ME and MT) on PP2A activity toward protein substrates. A direct material effect may refer to compounds having an $IC_{50}$ of below 100 µM.

As can be seen with reference to above Table 2, certain compounds of the present invention selectively modulate the carboxyl demethylating activity of the protein phosphatase specific protein methylesterase (MEase), thereby resulting in modulation of PP2A demethylation. In certain embodiments, compounds of the present invention show $IC_{50}$ values that range between 0.5 µM and 300 µM. In certain embodiments, compounds of the present invention show $IC_{50}$ values that range between 0.5 µM and 5 µM. In certain embodiments, compounds of the present invention show $IC_{50}$ values that range between 5 µM and 10 µM. In certain embodiments, compounds of the present invention show $IC_{50}$ values that range between 10 µM and 20 µM. In certain embodiments, compounds of the present invention show $IC_{50}$ values that range between 20 µM and 50 µM. In certain embodiments, compounds of the present invention show $IC_{50}$ values that range between 50 µM and 100 µM. In certain embodiments, compounds of the present invention show $IC_{50}$ values that range between 100 µM and 300 µM, and higher. Table 2 further suggests that certain compounds of the present invention modulate the methyl esterase (i.e., the carboxyl demethylating activity of the protein phosphatase specific protein MEase). Table 2 therefore shows that certain compounds of the present invention that show $IC_{50}$ values that range between 1 µM and 10 µM are selective towards MEase.

As can be seen with reference to above Table 2, certain compounds of the present invention selectively modulate the methylating activity of MTase, thereby resulting in modulation of PP2A methylation. In certain embodiments, compounds of the present invention show $IC_{50}$ values that range between 0.5 µM and 300 µM. In certain embodiments, compounds of the present invention show $IC_{50}$ values that range between 0.5 µM and 10 µM. In certain embodiments, compounds of the present invention show $IC_{50}$ values that range between 10 µM and 100 µM. In certain embodiments, compounds of the present invention show $IC_{50}$ values that between 100 µM and 300 µM, and higher. Table 2 further suggests that certain compounds of the present invention modulate the methyltransferase (i.e., the carboxyl methylating activity of the protein phosphatase 2A specific MTase). Table 2 therefore demonstrates that compounds of the present invention that show $IC_{50}$ values that range between 0.5 µM and 10 µM are selective towards MTase.

In certain embodiments, PP2A methylation is reduced in the presence of compound(s) described herein. In certain embodiments, PP2A methylation is reduced by at least 40%, 50%, 75%, 100% in the presence of compound(s) described herein. In certain embodiments, PP2A methylation is increased in the presence of compound(s) described herein. In certain embodiments, PP2A methylation is 1.5-fold, 2-fold, 3-fold, 4-fold, and 5-fold higher in the presence of compound(s) described herein.

In certain embodiments, PP2A phosphatase activity is increased in the presence of compound(s) described herein. In certain embodiments, phosphatase activity is 1.5-fold, 2-fold, 3-fold, 4-fold, 5-fold higher in the presence of compound(s) described herein. In certain embodiments, PP2A phosphatase activity is decreased in the presence of compound(s) described herein. In certain embodiments, PP2A phosphatase activity is reduced by at least 40%, 50%, 75%, 100% in the presence of compound(s) described herein.

In some embodiments, PP2A phosphatase activity is higher in the presence of compound(s) described herein. In some embodiments, the PP2A phosphatase activity is at least 1.1-fold, 1.2-fold, 1.5-fold, 2-fold, 3-fold, 4-fold, 5-fold higher in the presence of compound(s) described herein.

In some embodiments PP2A phosphatase activity is lower in the presence of compound(s) described herein. In some embodiments, the PP2A phosphatase activity is lower by at least 40%, 50%, 75%, 100% in the presence of compound(s) described herein.

In some embodiments, activity of MT is higher in the presence of compound(s) described herein. In some embodiments, the activity of MT is at least 1.1-fold, 1.2-fold, 1.5-fold, 2-fold, 3-fold, 4-fold, 5-fold higher in the presence of compound(s) described herein.

In some embodiments activity of ME is lower in the presence of compound(s) described herein. In some embodiments, the activity of ME is lower by at least 40%, 50%, 75%, 100% in the presence of compound(s) described herein.

Example 25

Effect of Compound I-63 on Non-Fasted Glucose Levels in Ob/Ob Mice

The present example demonstrates that compounds of the present invention (eg. Compound I-63) lowers non-fasted blood glucose levels in obese mice. Mice homozygous for the obese spontaneous mutation, ($Lep^{ob}$ commonly referred to as ob or ob/ob), exhibit obesity, hyperphagia, a diabetes-like syndrome of hyperglycemia, glucose intolerance, elevated plasma insulin, subfertility, impaired wound healing and an increase in hormone production from both pituitary and adrenal glands. They are also hypometabolic and hypothermic. The obesity is characterized by an increase in both the number and the size of adipocytes. Although hyperphagia contributes to the obesity, homozygotes gain excess weight and deposit excess fat even when restricted to a diet sufficient for normal weight maintenance in lean mice. Mice heterozygous for the $Lep^{ob}$ mutation appear like wild-type and are lean.

Forty-eight (48) B6.V-$Lep^{ob}$/J mice (00632, The Jackson Laboratory, JAX$^O$ mice), homozygous for the $Lep^{ob}$ mutation and thirty six (36) controls B6.V-$Lep^{ob}$/J-lean, heterozygous for the $Lep^{ob}$ mutation were used to study the effect of SIG1012 on non-fasted glucose levels. The mice were ear notched for identification and housed in individually and positively ventilated polycarbonate cages with HEPA filtered air at a density of 3 mice per cage. Bed-o-cob corn cob bedding was used and cages were changed every two weeks. The animal room was lighted entirely with artificial fluorescent lighting, with a controlled 12 h light/dark cycle (7 am to 7 pm light). The normal temperature and relative humidity ranges in the animal rooms were 22±4° C. and 50±15%, respectively. The animal rooms were set to have 15 air exchanges per hour. Filtered tap water, acidified to a pH of 2.8 to 3.2, and LabDiet AIN-76A was provided ad libitum.

Following acclimation, mice were assigned to groups A through G according to their body weight and genotype:

A Lean heterozygotes—B6.V-$Lep^{ob}$/J-lean Mice Fed Control Diet (AIN-76A);

B Lean heterozygotes—B6.V-$Lep^{ob}$/J-lean Mice Fed "Low" Compound I-63 (AIN-76A with 0.001% Compound I-63);

C Lean heterozygotes—B6.V-$Lep^{ob}$/J-lean Mice Fed "Medium" Compound I-63 (AIN-76A with 0.1% Compound I-63);

D Obese homozygotes—B6.V-$Lep^{ob}$/J Mice Fed Control Diet (AIN-76A);

E Obese homozygotes—B6.V-$Lep^{ob}$/J Mice Fed "Low" Compound I-63 (AIN-76A with 0.001% Compound I-63);

F Obese homozygotes—B6.V-$Lep^{ob}$/J Mice Fed "Medium" Compound I-63 (AIN-76A with 0.1% Compound I-63); and G Obese homozygotes—B6.V-$Lep^{ob}$/J Mice Fed Rosiglitazone Diet (AIN-76A with 195 mg/kg Rosilitizone). Rosiglitizone is an anti-diabetic drug and lowers blood glucose levels, therefore served as positive control.

Mice from Groups A through G were maintained on the respective diet for 14 days and blood glucose levels were measured weekly. Exemplary results are depicted in FIG. 3, which demonstrates that weekly administration of Compound I-63 results in 26-30% reduction in non-fasted blood glucose levels in homozygous obese mice while the anti-diabetic control drug, Rosiglitizone results in 66% reduction in non-fasted glucose levels in homozygous obese mice. No effect was observed with Compound I-63 on non-fasted blood glucose levels in heterozygous lean mice control.

Example 26

Effect of Compound I-63 on Glucose Metabolism in Wild-Type Mice

The present example demonstrates that long-term administration of compounds of the present invention (eg. Compound I-63) significantly improves glucose tolerance. The glucose tolerance test (GTT) measures the body's ability to metabolize glucose. It is currently used to diagnose patients with prediabetes disposition and diabetes.

Twenty (20) Swiss-Webster (wild-type) mice were acclimated for 2 weeks. The mice were ear notched for identification and housed in individually and negatively ventilated polycarbonate cages with HEPA filtered air at a density of 6 mice per cage. Bed-o-cob corn cob bedding was used and cages were changed every two weeks. The animal room was lighted entirely with artificial fluorescent lighting, with a controlled 12 h light/dark cycle (7 am to 7 pm light). The normal temperature and relative humidity ranged in the animal rooms are 22±4° C. and 50±15%, respectively. The animal rooms were set to have 15 air exchanges per hour. Filtered tap water, acidified to a pH of 2.8 to 3.2. LabDiet D10001 was provided ad libitum, and leftover food was removed once per week.

Following acclimation, mice are assigned to groups according to diet.
1. Control Diet (D10001)
2. Compound I-63 ((D11000 with 0.1% I-63)

The mice were maintained on the diet for 128 days. The mice are fasted for 18 hours prior to glucose measurements. Mice were weighed and glucose dose calculated for 2 mg/kg body weight. Sterile glucose solution was prepared at concentration of 10 mg/ml in advance. Blood glucose levels were measured with the OneTouch UltraSmart electronic glucometer at time point 0 with tail vein blood. Tail snipping was used to get blood samples. Before snips, the tail end was sprayed with ethyl chloride for local anesthesia to reduce pain. Glucose at a concentration of 2 mg/kg body weight in 0.2 ml solution was injected into the peritoneal of each mouse. Blood glucose was measured at 15, 30, 45, 90 and 120 minutes after glucose injection.

Figure 4:
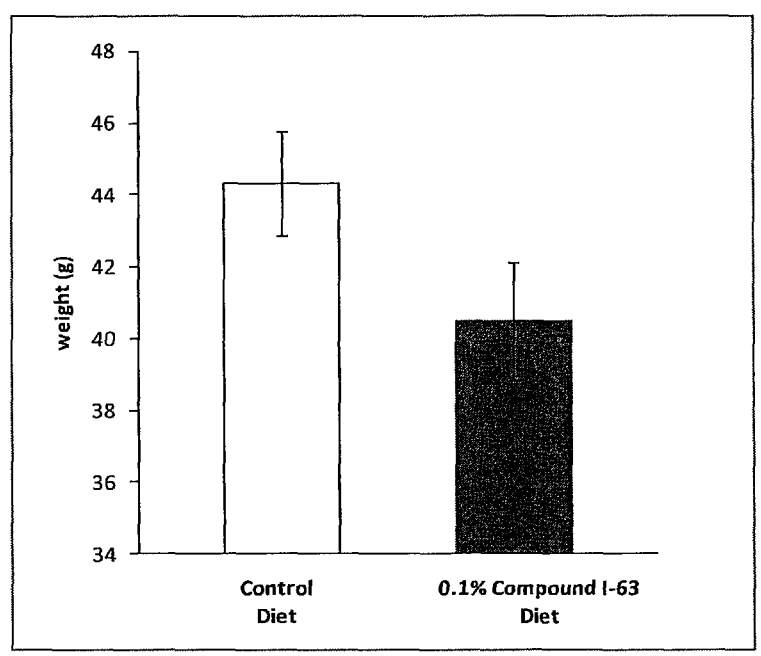
FIG. 4 depicts a bar graph demonstrating that wild-type mice treated with Compound I-63 have, on average, approximately 10% lower body weights than wild-type mice on control diet.
Figure 5:
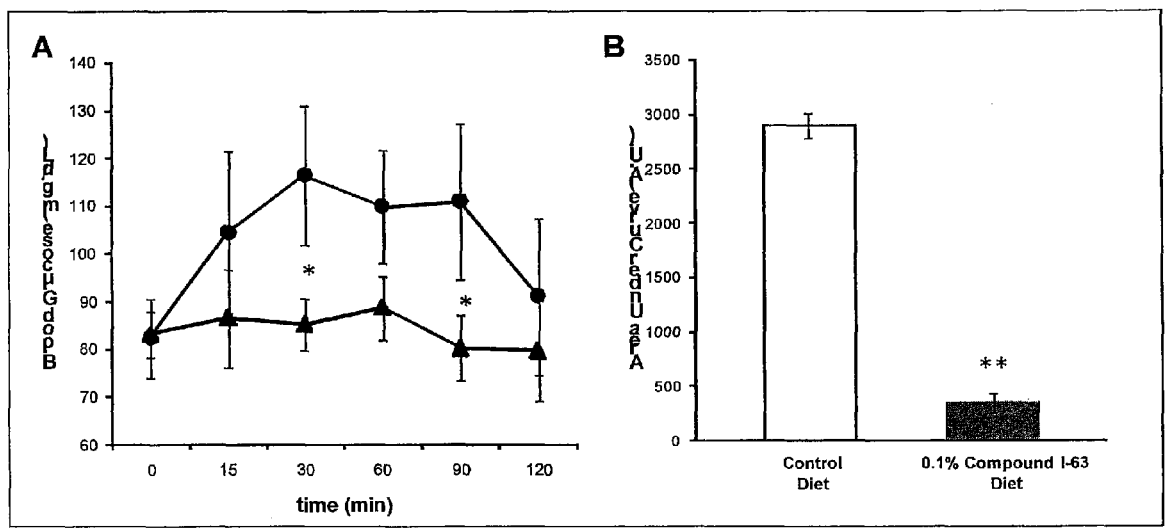
FIG. 5A depicts a graph demonstrating that wild-type mice treated with Compound I-63 show improved glucose tolerance in an intraperitoneal glucose tolerance test, with reductions in blood glucose levels at two time points ($*p<0.05$).
FIG. 5B depicts a bar graph demonstrating that incremental area under the curve of blood glucose levels in the glucose tolerance test for Compound I-63 treated mice is <10% than when mice were fed a control diet. ($***p<0.0001$).

FIG. 4 demonstrates that wild-type mice treated with Compound I-63 has <10% lower body weights than wild-type mice on control diet. FIG. 5A demonstrates that wild-type mice treated with Compound I-63 significantly maintains consistently lower glucose levels in the intraperitoneal glucose tolerance test (*p<0.05). FIG. 5B demonstrates that incremental area under blood glucose curve from basal levels after injection of glucose (20 mg/kg) in case of Compound I-63-treated mice is <10% compared to similar mice on control diet (***p<0.0001).

Example 27

Cytotoxicity of Compound I-63 in N2a Neuroblastoma Cells

Figure 6:
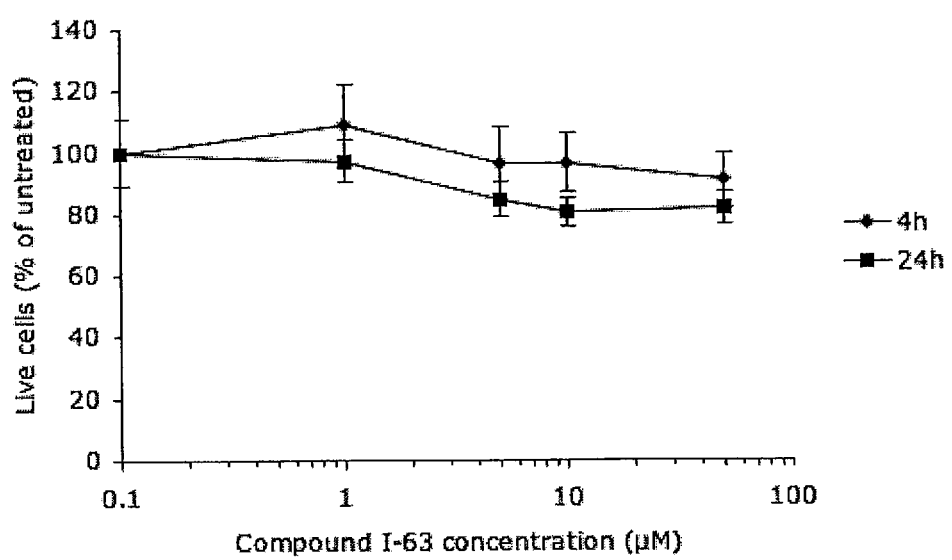
FIG. 6 depicts a graph demonstrating that cell survival is over 85% at all concentrations of compound I-63 tested, both at 4 hours and at 24 hours.

The present example demonstrates that compounds of the present invention (e.g., compound I-63) are not toxic to neuronal cells. $2 \times 10^4$ N2a cells were plated in each well of a 96-well cell culture plate containing 100 µl EMEM (Gibco), supplemented with 10% FBS (N2a growth medium), and were incubated at 37° C. for 48 hours. On the day of treatment, stock solutions of 5 mM, 1 mM, 0.5 mM and 0.1 mM of Compound I-63 in ethanol were further diluted with N2a growth medium to obtain Compound I-63-containing N2a medium with 50 µM, µM, 5 µM and 1 µM Compound I-63. The final concentration of ethanol in all media dilutions was 1%, and therefore 1% ethanol was added to the 0 µM Compound I-63 (untreated) control. The media dilutions were applied to the N2a cells (100 µl per well) and incubated at 37° C. for 4 hours or 24 hours. At the end of the treatment period, cell media was removed and 100 µl of pre-warmed phenol red-free N2a growth media was added to each well. 20 µl of the CellTiter 96® $AQ_{ueous}$ One Solution (Promega) was added to each well and the dish was incubated at 37° C. for 1-4 hours until visible reddish color develops. The dish was read at a wavelength of 490 nm using a plate reader. N2a cells were grown in 96-well dishes and were treated for 4 hours (♦) or 24 hours (■) with increasing concentrations of Compound I-63. Cell survival was assayed using the CellTiter 96® $AQ_{ueous}$ One Solution (Promega) using the manufacturer's directions. The error bars represent the standard error of the mean of three experiments. FIG. 6 demonstrates that cell survival is over 85% at all concentrations of compound I-63 tested, both at 4 hours and at 24 hours.

Example 28

Effect of Compound I-63 on Phosphorylated Tau In Vivo

Figure 7:
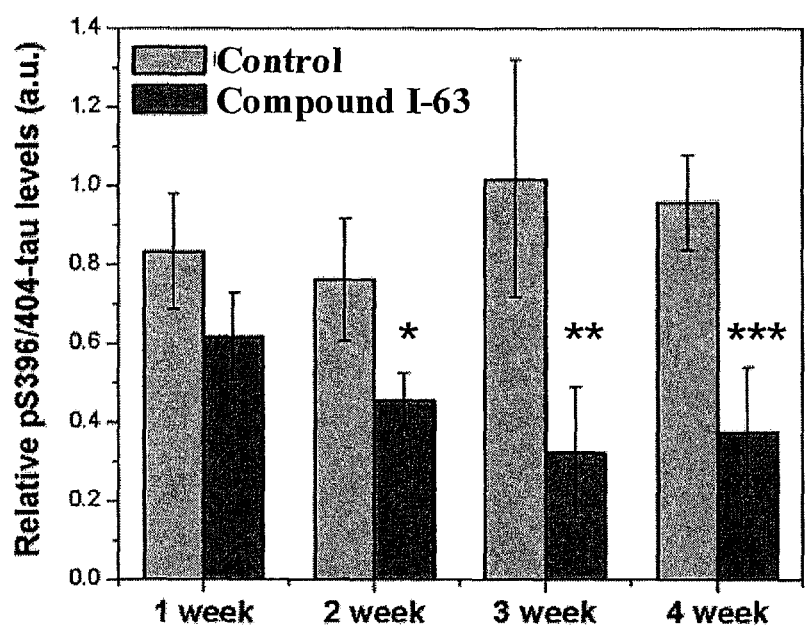
FIG. 7 depicts a bar graph demonstrating that when compound I-63 is administered at a 0.1% dosage level (% by weight in feed), there is a <40% reduction ($p<0.05$) in phosphorylation of tau, after two weeks of administration; and when compound I-63 is administered at a 0.1% dosage level, there is >50% and at least ~70% reduction in phosphorylation of tau, after three and four weeks of administration, when compared to a control.

The present example demonstrates that compounds of the present invention (e.g., compound I-63) lowers phosphorylated Tau in young, wild-type mice. Swiss Webster mice (9-12 weeks old) were fed ad libitum, either standard rodent chow (Control), or rodent chow formulated with 0.1 g Compound I-63 per 100 g chow (0.1% Compound I-63); water was changed weekly. Mice were housed at 23° C., on a 12 hour light and dark cycle, with 6 mice per cage. At weekly intervals up to 4 weeks, three and six mice from the Control and 0.1% Compound I-63 groups respectively were sacrificed by cervical dislocation, brains removed, snap-frozen in liquid nitrogen, and were stored at −80° C. Brains were homogenized in 350 µl of buffer containing 20 mM MOPS-Na, pH 7.2, 1 mM EDTA/DTT, 0.5 mg/L of aprotinin, leupeptin and pepstatin, 100 nM okadaic acid, and clarified by centrifugation (14,000 rpm, 10 min, 4° C.). Supernatant protein concentrations were measured by the Bradford method, 4 volumes of the supernatant and 1 volume of 5×SDS sample buffer were mixed and boiled for 2 minutes. 40 µg of the boiled homogenate were loaded on 12% polyacrylamide gels, and transferred to nitrocellulose membranes. Membranes are blocked in 5% BSA+TBST for 1 hour at room temperature, and incubated overnight at 4° C. with the following primary antibodies at the indicated dilutions: PHF1 mAb (recognizes phospho-Serine 396/404) at 1:2000, Tau-5 (Millipore; pan-tau mAb) at 1:10,000, and anti-GAPDH (Sigma mAb; used as loading control) at 1:50,000. Protein bands were detected with the ECL Plus reagent (GE Healthcare) and blots were exposed to Kodak XOmat film. Densitometric analyses were performed with ImageJ software. For relative phospho-tau levels of the Compound I-63-treated animals, the ratio of GAPDH-normalized phospho-tau to GAPDH-normalized total tau was further normalized to the corresponding ratios for the control group of mice. Error bars represent the standard error of the means. FIG. 7 depicts a bar graph demonstrating that when compound I-63 is administered at a 0.1% dosage level (% by weight in feed), there is a <40% reduction (p<0.05) in phosphorylation of tau at the serine and threonine residues whose phosphorylation has been associated with neurodegeneration and senile demensia, after two weeks of administration; and when compound I-63 is administered at a 0.1% dosage level, there is >50% and at least 70% reduction in phosphorylation of tau at the serine and threonine residues whose phosphorylation has been associated with neurodegeneration and senile demensia, after three and four weeks of administration, when compared to a control.

Example 29

Effect of Compound I-63 and Compound I-62 on Phosphorylated Tau In Vivo

Figure 8:
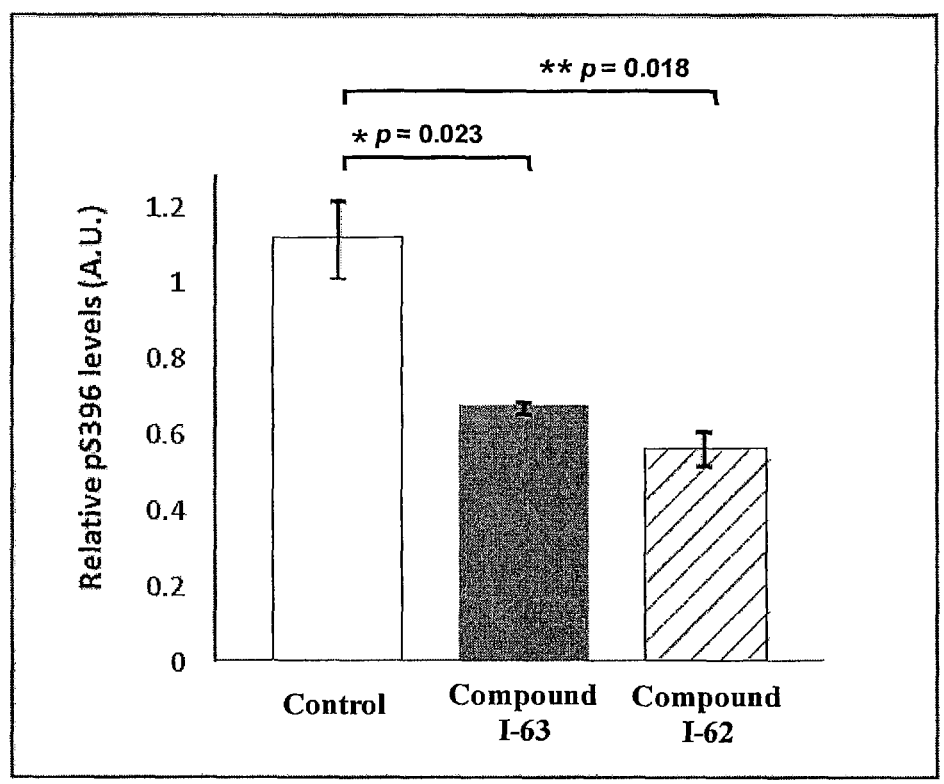
FIG. 8 depicts a bar graph demonstrating that both compound I-62 and compound I-63 are similarly effective in lowering phosphorylated tau levels in the brain by 40% following four weeks of administration, when compared to a control.

The present example demonstrates that compounds of the present invention (e.g., Compounds I-62 and I-63) lowers phosphorylated Tau in young, wild-type mice following four weeks of administration. Swiss Webster mice (9-12 weeks old) were fed ad libitum, either standard rodent chow (Control), or rodent chow formulated with 0.1 g Compound I-63 per 100 g chow (0.1% Compound I-63) or 0.1 g Compound I-62 per 100 g chow (0.1% Compound I-62); water was changed weekly. Mice were housed at 23° C., on a 12 hour light and dark cycle, with 6 mice per cage. At 4 weeks, six mice from the Control, 0.1% Compound I-63 and 0.1% Compound I-62 groups were sacrificed by cervical dislocation, brains removed, snap-frozen in liquid nitrogen, and stored at −80° C. Brains were homogenized in 350 µl of buffer containing 20 mM MOPS-Na, pH 7.2, 1 mM EDTA/DTT, 0.5 mg/L of aprotinin, leupeptin and pepstatin, 100 nM okadaic acid, and clarified by centrifugation (14000 rpm, 10 min, 4° C.). Supernatant protein concentrations were measured by the Bradford method, 4 volumes of the supernatant and 1 volume of 5×SDS sample buffer were mixed and boiled for 2 minutes. Boiled homogenate (20 µg) were loaded on 12% polyacrylamide gels, and transferred to nitrocellulose membranes. Membranes were blocked in 5% BSA+TBST for 1 hour at room temperature, and incubated overnight at 4° C. with the following primary antibodies at the indicated dilutions: pS396 (Signalway) that recognizes phospho-Serine 396 at 1:1000; Tau-5 (Millipore; pan-tau mAb) at 1:500, and anti-GAPDH (Sigma mAb; used as loading control) at 1:50000. Protein bands were detected with the ECL Plus reagent (GE Healthcare) and blots scanned on a Molecular Dynamics Storm Imager. Densitometric analyses were performed with ImageQuant software. For relative phospho-tau levels of the Compound I-63-treated and Compound I-62-treated animals, the ratio of GAPDH-normalized phospho-tau to GAPDH-normalized total tau was further normalized to the corresponding ratios for the control group of mice. Error bars represent the standard error of the means. FIG. 8 depicts a bar graph demonstrating that both compound I-62 and compound I-63 are similarly effective in lowering phosphorylated tau levels in the brain by 40% following four weeks of administration, when compared to a control.

Example 30

Effect of Compound I-63 on Motor Functions of JNPL3 Transgenic Mice Motor Tests Methods The present example demonstrates that compounds of the present invention (e.g, Compound I-63) has protective effects towards progressive motor deficits in JNPL3 transgenic mice. The JNPL3 transgenic mouse line that carries the transgene for the human P301L mutation of the microtubule-associated protein tau gene (MAPT) was used in this experiment (Lewis et al., 2000). 9-12 weeks old homozygous JNPL3 males (Taconic Farms, Hudson, N.Y.) were housed under standard conditions (temperature 22±2° C.; relative humidity 50±10%; 12 h light/12 h dark cycle) and allowed to acclimatize for 2 weeks. Following acclimatization, two groups of animals (6 animals per group) are changed to control diet (Research Diets; New Brunswick, N.J.) or purified 0.1% Compound I-63 formulated diet. The composite neuroscore (NS) was used as the scoring system to measure the following tasks: (1) forelimb flexion response during suspension by the tail, (2) righting and postural reflexes, and (3) prehensile traction test (Yoshiyama et al., 2005; Korenova et al., 2009). The neurological and motor examination included the basic reflex response by special attention to the assessment of the hind-limb escape extension reflex, the righting and postural reflexes and the prehensile traction test where the animal is allowed to grasp with its forepaws a horizontal cotton string (1 mm in diameter) suspended 70 cm above a padded surface. The scoring conditions were graded as follows:

Tail Suspension Test:
0—Animal displayed standard escape response
1—Animal did not exhibit full escape or inward trend with leg response
2—Animal maintained forelimbs in scissored, clasped or dystonic position Postural and Righting Reflex:
0—Animal could right when placed supine
1—Animal righting slowed (>1 s)
2—Animal did not exhibit any righting reflex Prehensile Traction Test:
0—Animal could complete test with at least 3 paws and tail within 2 min
1—Animal could hold on to string without falling within 2 min
2—Animal fell before 2 min without completion
3—Animal was unable to perform test Each animal was scored using a scaling system ranging from 0-12 (normal), 13-20 (mild or early), 21-23 (moderate) and 24-30 (severe) to reflect serious impairment of neuromuscular functionality and muscular weakness. The total score was averaged and compared between groups since 7 months in diet.

Figure 9:
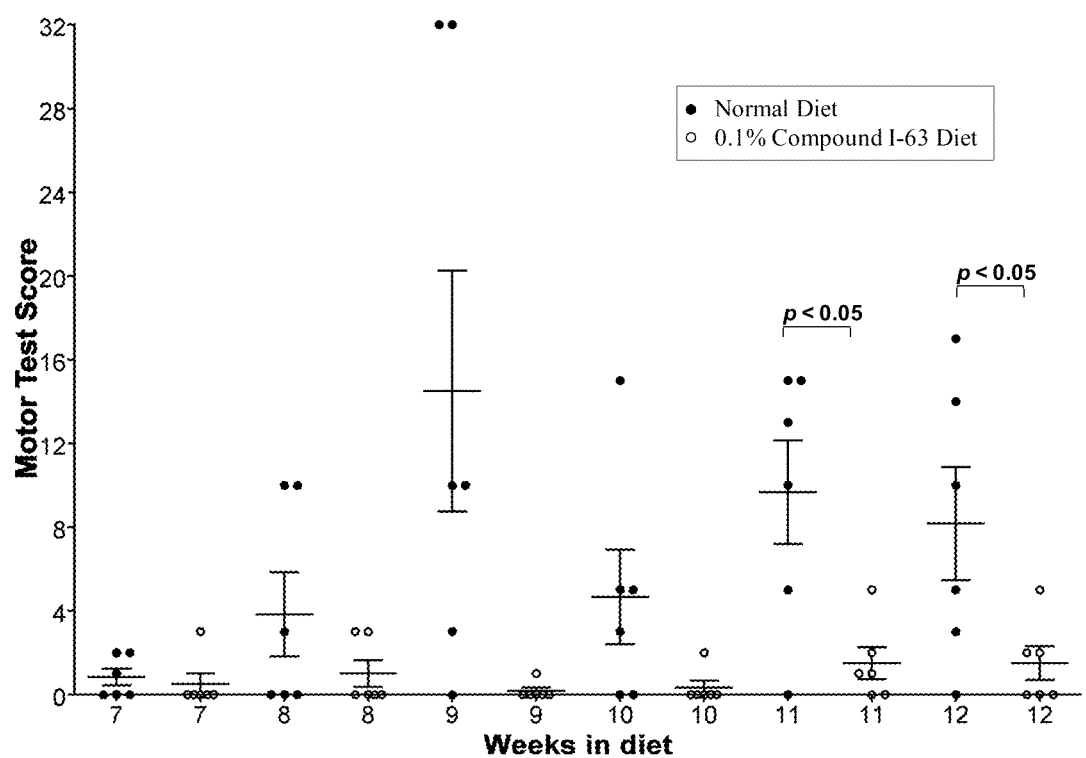
FIG. 9 depicts a graph demonstrating that administration of 0.1% of Compound I-63 after ten weeks resulted in protection of JNPL3 transgenic mice from developing motor dysfunction; and that mean motor test scores for mice on Compound I-63 diet were 75% less than motor test scores of mice on control diet after eleven and twelve weeks of administration of Compound I-63 ($p<0.05$).

Motor test scores vs. weeks of mice fed control diet (closed circles) and 0.1% Compound I-63 formulated diet (open circles). FIG. 9 demonstrates that administration of 0.1% of Compound I-63 after ten weeks resulted in protection of JNPL3 transgenic mice from developing motor dysfunction; and that mean motor test scores for mice on Compound I-63 diet were 75% less than motor test scores of mice on control diet after eleven and twelve weeks of administration of Compound I-63 ($p<0.05$). A reduction in motor scores represents a reduction in impairment of neuromuscular functionality and muscular weakness.

Example 31

Effect of PP2A on Alpha-Synuclein Phosphorylation

Dephosphorylation Assay of Human α Synuclein by PP2A and PP1.

Figure 10:
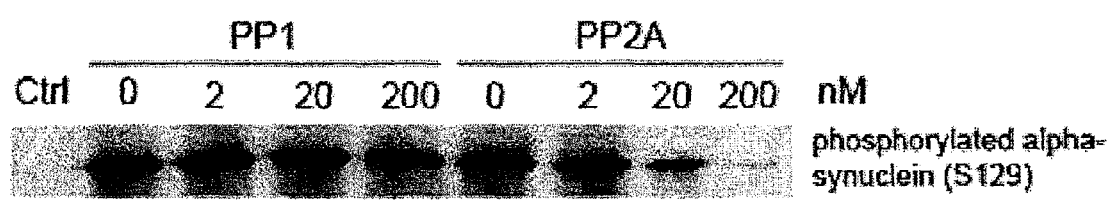
FIG. 10 depicts a Western blot demonstrating that phosphorylated α synuclein can be dephosphorylated by PP2A in a concentration dependent manner whereas this effect is not observed with PP1; and specifically, at 200 nM concentration, PP2A dephosphorylates more than 95% of the serine 129 phosphorylated alpha synuclein.

The present example provides a method for PP2A or PP1 dephosphorylation of human alpha-synuclein which is phosphorylated at Ser129, and demonstrates that PP2A (unmethylated AC dimer) but not PP1 can dephosphorylate alpha-synuclein phosphorylated at Ser129 under the in-vitro experimental conditions described below. PP2A or PP1 (serial dilutions of 200 nM, 100 nM, 50 nM, 25 nM, 12 nM, and 0 nM as a negative control) were incubated with serine 129 phosphorylated alpha-synuclein in MOPS buffer. The reactions were stopped by adding 5×SDS sample buffer. Levels of phosphorylated-alpha-synuclein were assessed by western blotting using an anti-phospho-Ser 129 antibody. FIG. 10 demonstrates that phosphorylated alpha-synuclein can be dephosphorylated by PP2A in a concentration dependent manner whereas this effect is not observed with PP1. Specifically, at 200 nM concentration, PP2A dephosphorylates more than 95% of the serine 129 phosphorylated alpha-synuclein.

Example 32

Effect of PP2A Methylation on Alpha-Synuclein Phosphorylation

Figure 11:
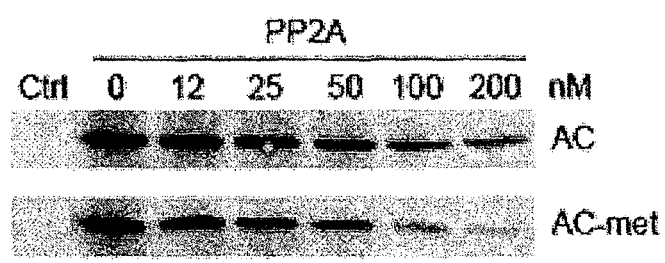
FIG. 11 depicts a Western blot demonstrating that methylation increases PP2A dephosphorylation activity towards alpha-synuclein.
Figure 12:
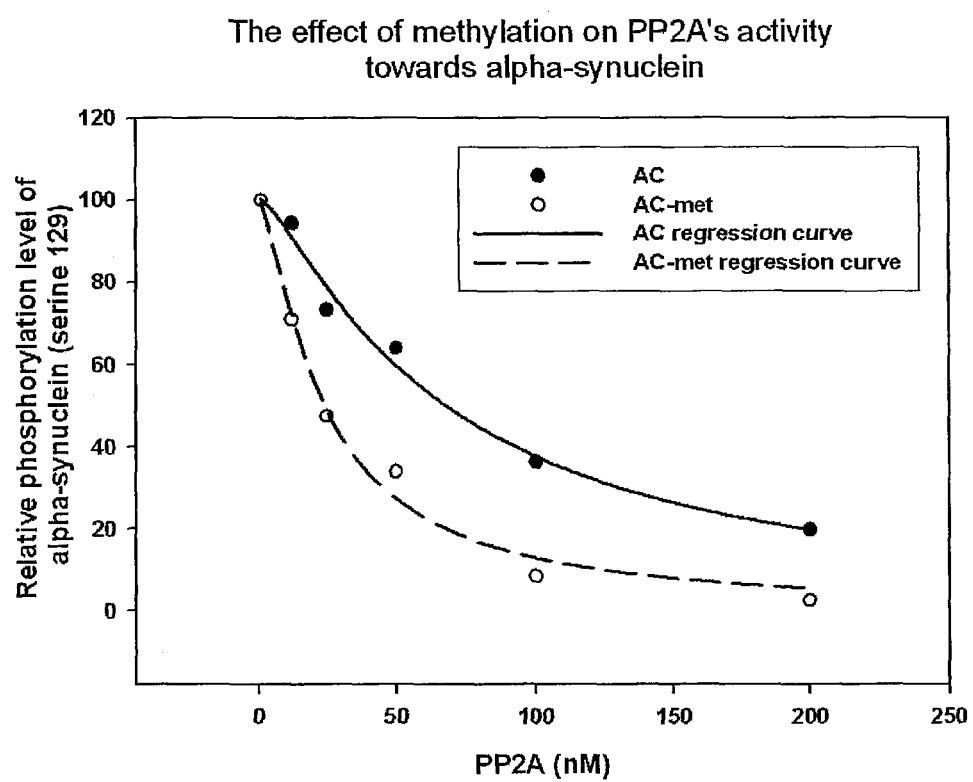
FIG. 12 depicts a graph demonstrating that methylation increases PP2A dephosphorylation activity towards alpha-synuclein; and specifically, methylation reduces the $EC_{50}$ value of PP2A AC dimer from ~60 nM to ~20 nM.

The present example demonstrates that methylation of PP2A increases its dephosphorylation activity or phosphatase activity towards alpha-synuclein phosphorylated at Ser129. Concentrated samples of the methylated and unmethylated AC dimer of PP2A were each serially diluted to final concentrations of 200 nM, 100 nM, 50 nM, 25 nM, and 12 nM. A buffer sample (with 0 nM PP2A) was used as the negative control. The dephosphorylation assay and western blotting were performed as described above in Example 31 Western blots were scanned on a Storm Scanner (Molecular Dynamics) and band intensities quantified with Image Quant software. The relative phosphorylation levels were calculated with the following formula: Relative phosphorylation level (%)=Signal of Sample/Signal of Negative Control*100%. Regression curves of relative phosphorylation levels as a function of PP2A concentration were plotted, and the $EC_{50}$ values for methylated and unmethylated PP2A were estimated using the SigmaPlot program. The $EC_{50}$ is a measure of phosphatase activity or dephosphorylation activity of PP2A toward phosphorylated alpha-synuclein. Specifically, it is the concentration of the AC dimer required to achieve 50% dephosphorylation of phosphorylated alpha-synuclein. Exemplary results are depicted in FIG. 11 and FIG. 12, which demonstrate that methylation increases PP2A dephosphorylation activity towards alpha-synuclein. Specifically, methylation reduces the $EC_{50}$ value of PP2A AC dimer from ~60 nM to ~20 nM.

Example 33

Effect of Compound I-63 on Alpha-Synuclein Phosphorylation

The present example provides a method for identifying a compound which is capable of modulating the phosphatase activity of PP2A towards alpha synuclein. PP2A is incubated with serial dilutions of the compound (to yield final concentrations of 100 µM, 10 µM, 1 µM, 0.1 µM, and 0 µM as negative control) in a solution containing MOPS buffer for 10 min-30 min. Following incubation, the substrate (serine 129 phosphorylated a synuclein) is added to the reaction, and the reaction is allowed to continue as described in Example 31. The effect of the compound is based on the dephosphorylation-dependent $EC_{50}$ value of the reaction with the compound, compared to the control reaction without the compound sample.

Example 34

Effect of Compound I-63 on MPTP-induced Neurotoxicity in MPTP Mouse Model of Parkinson's Disease MPTP (1-methyl-4-phenyl-1,2,3,6-tetrahydropyridine) is routinely used as a chemical agent that induces Parkinson's disease-like neurodegeneration in cellular and animal models. Both Parkinson's Disease and MPTP-induced neurotoxicity are associated with a number of different biomarkers including reduction of tyrosine hydroxylase levels and activity. Tyrosine hydroxylase is a key enzyme in the dopamine biosynthesis pathway as it is involved in the conversion of tyrosine to dopamine. Tyrosine hydroxylase activity is regulated by its phosphorylation status and PP2A is known to be involved in this regulation.

The present example demonstrates that compounds of the present invention have a protective effect towards toxin-induced neurodegeneration. C57BL/6J mice, aged 2-3 months were fed ad libitum, either standard rodent chow (Control), or rodent chow formulated with 0.1 g Compound I-63, or 0.01 g Compound I-63 per 100 g chow (0.1% and 0.01% Compound I-63, respectively); water was changed weekly. Mice were housed at 23° C., on a 12 hour light and dark cycle, with 6 mice per cage. After 2 weeks, 8-12 mice each from the Control, 0.1% Compound I-63 and 0.01% Compound I-63 groups were injected with either saline, or 10 mg/kg MTPT i.e., four times, every 2 hours, on the same day. Mice were then maintained on their respective feeds for another week, at which point they were sacrificed by cervical dislocation and brains dissected for biochemical analyses.

Figure 13:
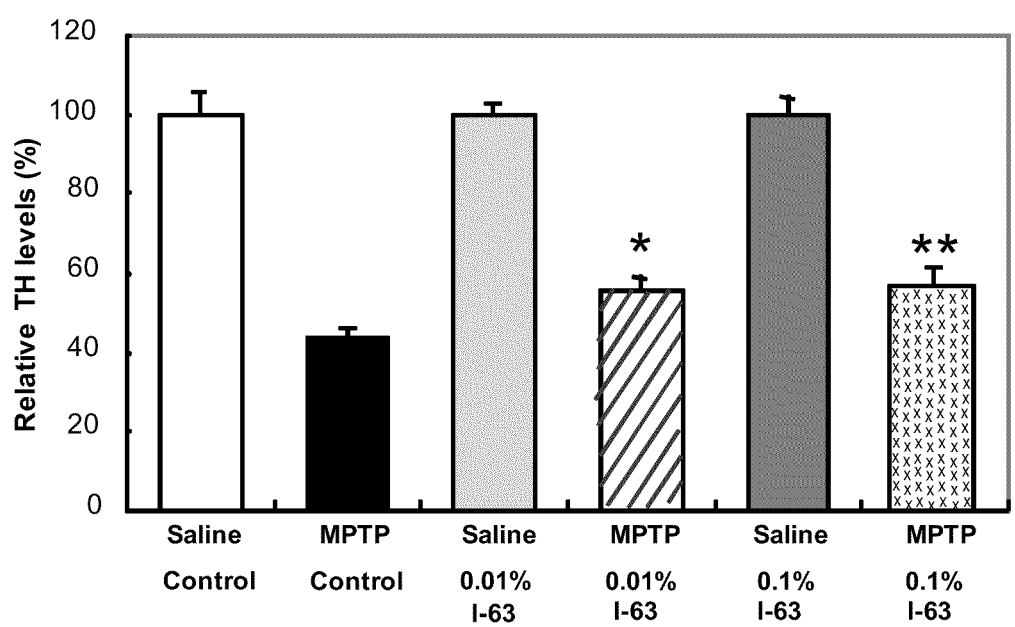
FIG. 13 depicts a bar graph demonstrating that mice fed 0.01% and 0.1% Compound I-63 diets were protected against acute MPTP-induced neurotoxicity, which was evidenced by rescuing ($p<0.05$) of the tyrosine hydroxylase defect by approximately 20%.

Striatal tyrosine hydroxylase (TH) content was measured by ELISA as follows. Ninety-six well microtiter plates (Thermo Labsystems) were incubated overnight at 4° C. with monoclonal anti-TH antibody (1:500; Calbiochem) in 8 mM sodium phosphate, 2 mM potassium phosphate, and 0.14 M sodium chloride, pH 7.4 (PBS). Wells were washed four times with PBS and then blocked for 1 hour using 5% (w/v) Carnation (Nestlé) nonfat dry milk in PBS. Striatal tissue samples were homogenized by sonication in PBS-0.5% Triton X-100 (PBST) with 0.25% (w/v) SDS. Purified TH protein (Cell 2 Cell, San Clemente, Calif.) was used to establish a standard curve. Samples and standards were incubated for 1 hour at room temperature, washed four times with PBST, and then incubated for 1 hour with both polyclonal anti-TH (1:500; Calbiochem) and polyclonal anti-rabbit horseradish peroxidase (HRP) (1:3000; Amersham Biosciences) in blocking solution. After washing four times with PBST, wells were incubated with Amplex Red (Molecular Probes) HRP substrate. The reaction product was measured fluorometrically within the linear range of detection (excitation:emission ratio of 530:580 nm). Controls included omission of primary or secondary TH antibody. Data were expressed as percent TH levels in MPTP-treated mice relative to saline-injected mice. Multiple comparisons were made using one-way ANOVA followed by the Newman-Keuls multiple range test. Administration of MPTP to mice on control diets significantly reduced tyrosine hydroxylase levels by 60%. Mice on 0.01% and 0.1% Compound I-63 diets were protected against acute MPTP-induced neurotoxicity, evidenced as a significant (p<0.05) rescuing of the tyrosine hydroxylase defect by approximately 20%. Results are depicted in FIG. 13 which demonstrate that compounds of the present invention are useful to ameliorate symptoms associated with Parkinson's Disease.

Example 35

Effect of Compound I-63 on Locomotor Tests in Alpha-Synuclein Over-Expressing Mice Transgenic mice over-expressing the full length human alpha-synuclein have been described previously, and are excellent models for sensorimotor tests that are sensitive to alterations in the nigrostriatal dopaminergic system [Fleming, S. M. et. al., *J. Neurosci.* 24, 9434-40, (2004)]. The present example demonstrates that administration of Compound I-63 to alpha-synuclein transgenic mice for 3 months, results in a significant improvement in locomotor activity as measured by the open-field and rota-rod tests.

Thy1-alpha-synuclein transgenic mice (9-12 weeks old) and age-matched wild type mice were housed in clear plastic cages in a temperature-, and humidity-controlled environment with a 12 hour-light/dark cycle (light switched on at 7 a.m.), and were maintained on an ad libitum diet of lab chow and water. The animal feeds used were either normal (Control) or formulated with Compound I-63 at 0.01% and 0.1%. Behavioral testing was carried out monthly, for three months, for each group of mice (n=9 to 13).

Locomotor activity was assessed in an open field paradigm by a Digiscan activity monitor utilizing a grid of infrared beams that record the location and path of the animal (horizontal activity) as well as the number of rearing movements (vertical activity). Mice were first placed in the same environment as that of the testing chamber 30 min. prior to testing. Each mouse was then placed in the middle of an open field chamber (42×42 cm acrylic animal cages, Accuscan Instruments) and locomotion was recorded for 10 min. The infrared light beam sensors were connected to a computer that recorded animal position every millisecond. AccuScan VersaMax software was used to record the total number of movements, the distance traveled, the time spent moving and the total number of infrared beam breaks. The total number of squares crossed by each mouse was recorded and average horizontal and vertical activities was determined for each group of mice.

Motor coordination and motor learning were measured by rota-rod tests. The Mice were placed on top of a speed-controlled rotating cylinder (diameter: 4.5 cm) with a coarse surface for a firm grip. Mice were individually tested three times with the cylinder rotating at a speed of 5 rpm, accelerating at 0.2 rpm/second, to a final speed of 40 rpm. A cut-off time of 3 min and an inter-trial interval of 60 min were used. The time spent on the rotating cylinder without falling down was measured. The significance of differences in activity at 3 months between treated and control groups was measured by a student's t-test.

Figure 14:
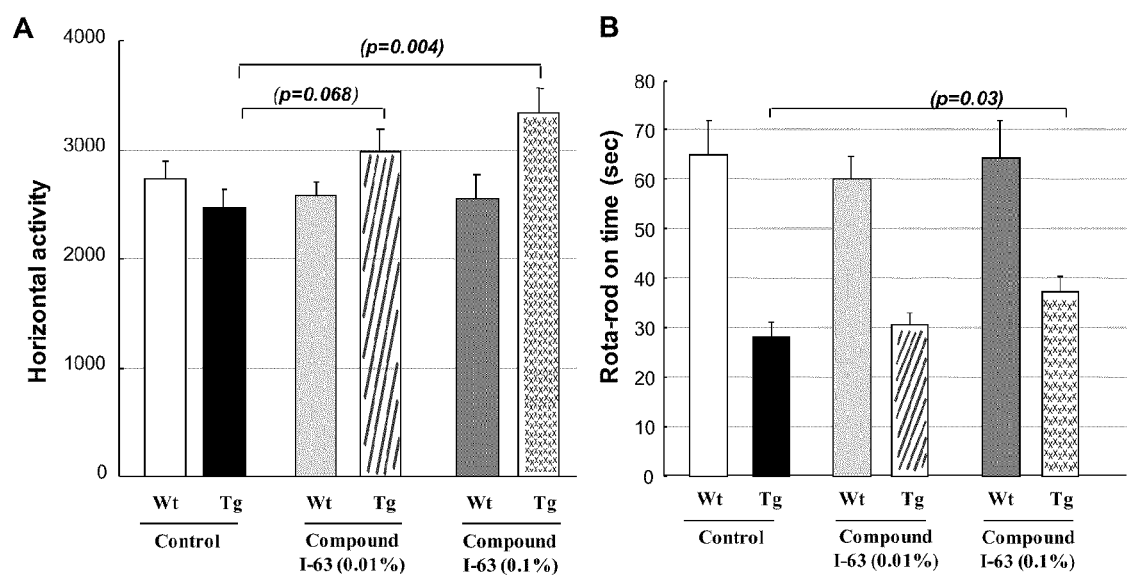
FIG. 14A depicts a bar graph demonstrating that alpha-synuclein transgenic mice treated with 0.1% Compound I-63 have an average 30% increase ($p=0.004$) in horizontal activity.
FIG. 14B depicts a bar graph demonstrating that alpha-synuclein transgenic mice treated with 0.1% Compound I-63 have an average 25% increase ($p=0.03$) in Rota-rod on time.

In the present example, alpha-synuclein transgenic mice on a diet of 0.1% Compound I-63 showed increases in horizontal activity (p=0.004; FIG. 14A), and in Rota-rod on-time (p=0.03; FIG. 14B). Transgenic mice on a diet of Compound I-63 showed an increase in horizontal activity at a dosage of 0.01% (p=0.068) and at a dosage of 0.1% (p=0.004) (FIG. 14A) in comparison to wild-type mice on the same diet, which indicates that Compound I-63 has protective effects specific to alpha-synuclein-induced alterations in locomotor activity.

Example 36

Acetonitrile-Ethanol Extraction of Compounds from Coffee Wax

Forty-eight grams of coffee wax (Amsyn, Inc., Alemark Chemicals) was dispensed in 100 ml of acetonitrile and heated at 60° C. on a rotovap. The soluble phase was separated from the insoluble solid phase. This extraction was repeated three times. The three soluble phases were combined, cooled at 4° C. up to 16 hours and filtered. The precipitate collected from the above filtration was redissolved in 200 ml of hot acetonitrile at 60° C., cooled at 4° C. up to 16 hours, and filtered. The solid phase was redissolved with 100 ml of hot ethanol at 70° C., cooled at room temperature and incubated for 16 hours. The precipitate included a mixture of crude compound I-63 and I-62 to yield 4.4 grams. The obtained sample contained high levels of compounds described herein. Levels of compound I-63 were estimated between 4% (wt/wt) (as measured by HPLC) to 14% (wt/wt) (as measured by LC/MS) and 17-20% (wt/wt) (as measured by MS/MS). Analysis by MS/MS showed that the remaining compounds in the sample were I-62, an analog of compound I-63. HPLC methods were performed using an Agilent 1200 HPLC. LC/MS and MS/MS methods were performed using an Agilent 6410 Triple Quadrupole mass spectrometer with Agilent 1200 HPLC.

Example 37

Hexane-Ethyl Acetate Extraction of Compounds from Coffee Wax

Ten grams of coffee wax (Amsyn Inc., Alemark Chemicals) were completely dissolved in 150 ml of ethyl acetate by heating at 50° C. on a rotorvapor. The mixture was subsequently cooled at room temperature for 1 hour and filtered. The solid precipitate was discarded. The filtrate was evaporated to dryness and the precipitate was dissolved in 200 ml of hexane at 50° C. and filtered. The purity of compound I-63 and I-62 in the solid phase was approximately 70%. The purity of compound I-63 and I-62 in the liquid phase was 15-40%. The majority of compound I-63 and I-62 was in the liquid phase. Further extraction of the solid phase with ethyl acetate can remove a substantial amount of caffeine. Further extraction of the liquid phase to obtain more I-62 and I-63 is achieved by evaporation and/or concentration, precipitation with another solvent, recycling the liquid phase back to treat more coffee wax.

Example 38

Preparation of PO Formulation D @6.67 mpk

Compound I-63 (11.0 mg) was mixed with Tween 80 (1375 µL) and heated using a heat gun with constant mixing until clear. PEG400 (1375 µL) was added to the solution and again mixed until clear. When PBS (2750 µL) was added, the solution would not clear despite mixing and heating. Additional Tween 80 (1375 µL) and PEG400 (1375 µL) were added to rescue the solution, which cleared after extensive mixing with heat. PBS (2750 µL) was added make up the 25:25:50 PEG400:Tween 80:PBS ratio of solvents.

Example 39

Preparation of PO Formulation K @ 33.3 mpk

Compound I-63 (247.5 mg) was mixed with ethyl oleate (500.8 mg), Solutol HS-15 (5000.3 mg), and ethanol (2.8 mL of denatured SDA-3A containing 95% SDA-3A (100:5 ethanol:methanol) and 5% isopropanol) to generate Formulation C. In a separate vial, compound I-63 (30.3 mg) was dissolved Tween 80 (3 mL) with heat and vortexing until clear. To this solution was added PEG400 (3 mL), and the mixture was again mixed until clear with light heating. Separately, compound I-63 (1 mL of Formulation C as described above) was mixed with phosphate buffered saline (5 mL) and vortexed thoroughly. These two solutions were mixed to yield a final solution containing 0.5% of compound I-63 in 25% Tween 80, 25% PEG400, and 50% PBS containing ethanol, solutol, and ethyl oleate.

The following example further illustrates an oral composition containing a compound of Formula I, Ia, Ib, Ic, Id, Ie, If, Ig and/or Ih.

Example 40

| INGREDIENTS | AMOUNT (wt %) |
|---|---|
| Compound I-63 | 0.5-3.0% |
| Ethyl Oleate | 0-1% |
| Solutol-HS15 | 0-7% |
| SDA-3A alcohol | 0-5% |
| Isopropanol | 0-1% |
| Tween-80 (Polysorbate 80) | 20-30% |
| PEG-400 | 20-30% |
| PBS | 40-43% |
| pH | 4.0-9.0 |

EQUIVALENTS

Those skilled in the art will recognize, or be able to ascertain using no more than routine experimentation, that while the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the, group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any targeting moiety, any disease, disorder, and/or condition, any linking agent, any method of administration, any therapeutic application, etc.) can be excluded from any one or more claims, for any reason, whether or not related to the existence of prior art.

Publications discussed above and throughout the text are provided solely for their disclosure prior to the filing date of the present application. Nothing herein is to be construed as an admission that the inventors are not entitled to antedate such disclosure by virtue of prior disclosure.

We claim:

1. A method for reducing the severity of symptoms in a subject suffering from a neurodegenerative disease or disorder, the method comprising administering to the subject a therapeutic amount of a pharmaceutical composition, wherein the pharmaceutical composition comprises at least 8.0 mg of a composition consisting essentially of an at least 80% or above pure or synthetic compound selected from the group consisting of:

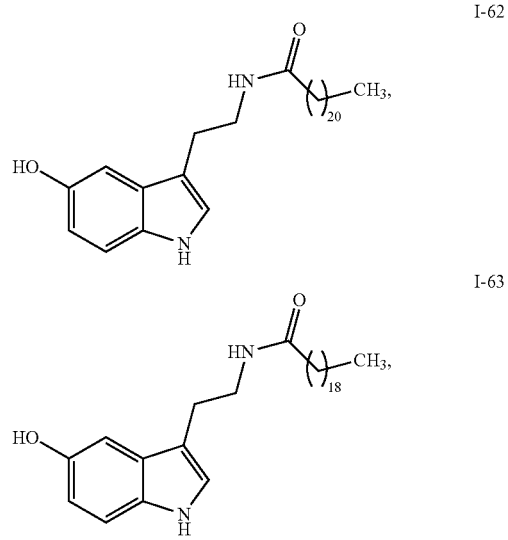

or a mixture of compounds I-62 and I-63,
wherein the pharmaceutical composition is further characterized by:
the therapeutic amount being effective to modulate phosphatase activity of protein phosphatase 2A (PP2A) in nerve cells,
containing less than 10% of caffeine, caffeic acid, and chlorogenic acid; and
the neurodegenerative disease is characterized by:

(1) abnormal methylation of protein phosphatase 2A (PP2A) and hyperphosphorylation of tau; or
(2) abnormal methylation of protein phosphatase 2A (PP2A) and abnormal phosphorylation of alpha-synuclein; or
(3) abnormal protein phosphatase 2A (PP2A) activity; hyperphosphorylation of tau, and abnormal phosphorylation of alpha-synuclein;
or a combination thereof;
wherein I-62 and I-63 are the only compounds in the composition that modulate PP2A activity in nerve cells.

2. The method according to claim 1, wherein the neurodegenerative disease is a tauopathy.

3. The method according to claim 2, wherein the tauopathy is selected from the group consisting of Alzheimer's disease, neurodegeneration in adult cases of Down's syndrome, Dementia puglistica, Pick's disease, Guam parkinsonism dementia complex, Fronto-temporal dementa, Cortico-Basal Degeneration, Pallido-Pontal-Nigral Degeneration, Progressive Nuclear Palsy and Parkinsonism of Chromosome 17 (FTDP-17), and a combination thereof.

4. The method according to claim 2, wherein the tauopathy is Alzheimer's disease.

5. The method according to claim 1, wherein the neurodegenerative disease is a synucleopathy.

6. The method according to claim 5, wherein the synucleopathy is selected from the group consisting of Parkinson's disease, Dementia with Lewy bodies, Multiple System Atrophy, and a combination thereof.

7. The method according to claim 5, wherein the synucleopathy is Parkinson's disease.

8. The method according to claim 1, wherein modulation of the phosphatase activity of protein phosphatase 2A (PP2A) results in a changed pattern of phosphorylation of substrate Tau compared to a control.

9. The method according to claim 1, wherein modulation of the phosphatase activity of protein phosphatase 2A (PP2A) results in a changed pattern of phosphorylation of substrate alpha-synuclein compared to a control.

10. The method according to claim 1, wherein the therapeutic amount is at least 12.0 mg per day.

11. The method according to claim 1, wherein the therapeutic amount is at least 20.0 mg per day.

12. The method according to claim 1, wherein the therapeutic amount is at least 50.0 mg.

13. The method according to claim 1, wherein the therapeutic amount is at least 100.0 mg.

* * * * *